US011352673B2

(12) United States Patent
Gomis et al.

(10) Patent No.: US 11,352,673 B2
(45) Date of Patent: *Jun. 7, 2022

(54) METHOD FOR THE DIAGNOSIS, PROGNOSIS AND TREATMENT OF LUNG CANCER METASTASIS

(71) Applicants: Fundació Institut de Recerca Biomèdica (IRB Barcelona), Barcelona (ES); Institució Catalana de Recerca i Estudi Avançats, Barcelona (ES)

(72) Inventors: Roger Gomis, Barcelona (ES); Evarist Planet, Barcelona (ES)

(73) Assignees: Fundacio Institut de Recerca Biomedica (IRB Barcelona); Institucio Catalana de Recerca i Estudis Avancats

( * ) Notice: Subject to any disclaimer, the term of this patent is extended or adjusted under 35 U.S.C. 154(b) by 351 days.

This patent is subject to a terminal disclaimer.

(21) Appl. No.: 15/984,629

(22) Filed: May 21, 2018

(65) Prior Publication Data
US 2019/0119757 A1  Apr. 25, 2019

Related U.S. Application Data

(62) Division of application No. 14/405,724, filed as application No. PCT/IB2013/001859 on Jun. 6, 2013, now Pat. No. 10,006,091.

(60) Provisional application No. 61/656,372, filed on Jun. 6, 2012.

(51) Int. Cl.
*C12Q 1/6886* (2018.01)
*A61K 47/54* (2017.01)
*G01N 33/574* (2006.01)
*C07K 16/28* (2006.01)

(52) U.S. Cl.
CPC .......... *C12Q 1/6886* (2013.01); *A61K 47/548* (2017.08); *C07K 16/2875* (2013.01); *G01N 33/57423* (2013.01); *C12Q 2600/106* (2013.01); *C12Q 2600/112* (2013.01); *C12Q 2600/118* (2013.01); *C12Q 2600/156* (2013.01); *C12Q 2600/158* (2013.01); *G01N 2333/82* (2013.01); *G01N 2800/50* (2013.01); *G01N 2800/52* (2013.01)

(58) Field of Classification Search
CPC ......................... G01N 33/50; G01N 33/57423
See application file for complete search history.

(56) References Cited

U.S. PATENT DOCUMENTS

| 5,176,996 | A | 1/1993 | Hogan et al. |
| 5,256,775 | A | 10/1993 | Froehler |
| 5,264,564 | A | 11/1993 | Matteucci |
| 6,274,338 | B1 | 8/2001 | Glimcher et al. |
| 6,287,813 | B1 | 9/2001 | Fussenegger et al. |
| 6,740,522 | B2 | 5/2004 | Anderson et al. |
| 7,097,834 | B1 | 8/2006 | Boyle |
| 7,214,781 | B2 | 5/2007 | Mitsuhashi et al. |
| 7,364,736 | B2 | 4/2008 | Boyle et al. |
| 7,411,050 | B2 | 8/2008 | Anderson |
| 9,134,237 | B2 | 9/2015 | Connelly et al. |
| 9,702,878 | B2 | 7/2017 | Gomis et al. |
| 10,006,091 | B2 | 6/2018 | Gomis et al. |
| 10,047,398 | B2 | 8/2018 | Gomis et al. |
| 10,114,022 | B2 | 10/2018 | Gomis et al. |
| 10,119,171 | B2 | 11/2018 | Gomis et al. |
| 10,793,642 | B2 | 10/2020 | Gomis et al. |
| 10,866,241 | B2 | 12/2020 | Gomis et al. |
| 11,041,213 | B2 | 6/2021 | Gomis et al. |
| 11,041,861 | B2 | 6/2021 | Gomis et al. |
| 2004/0132086 | A1 | 7/2004 | Horwitz et al. |
| 2008/0219996 | A1 | 9/2008 | Kalebic et al. |
| 2009/0029378 | A1 | 1/2009 | Connelly et al. |
| 2009/0048117 | A1 | 2/2009 | Glimcher et al. |
| 2009/0220955 | A1 | 9/2009 | Verrant |
| 2010/0215588 | A1 | 8/2010 | Skaliter et al. |
| 2011/0269637 | A1 | 11/2011 | Broet et al. |
| 2014/0057796 | A1* | 2/2014 | Gomis ............ G01N 33/57415 506/9 |
| 2014/0105918 | A1 | 4/2014 | Gomis et al. |
| 2014/0162887 | A1 | 6/2014 | Martin et al. |
| 2014/0314792 | A1 | 10/2014 | Gomis et al. |

(Continued)

FOREIGN PATENT DOCUMENTS

| CN | 1471587 | A | 1/2004 |
| EP | 1961825 | A1 | 8/2008 |
| EP | 2650682 | A1 | 10/2013 |
| WO | WO-8604920 | A1 | 8/1986 |
| WO | WO-8809810 | A1 | 12/1988 |

(Continued)

OTHER PUBLICATIONS

Abbott Molecular, "Vysis LSI IGH/MAF Dual Color Dual Fusion Probe," accessed at http://abbottmolecular.com/us/products/analyte-specific-reagent/fish/vysis-lsi-igh-maf-dual-color-dual-fusion-probe.html, accessed on Oct. 16, 2014, 2 pages.

Abnova, "MAF FISH Probe," accessed at http://abnova.com/products/products_detail.asp?sCatalog_id=FA0375, accessed on Oct. 16, 2014, 2 pages.

(Continued)

*Primary Examiner* — Peter J Reddig
(74) *Attorney, Agent, or Firm* — Sterne, Kessler, Goldstein and Fox P.L.L.C.

(57) ABSTRACT

The present invention relates to a method for the diagnosis or the prognosis of metastasis in lung cancer which comprises determining if the c-MAF gene is amplified in a primary tumor sample. Likewise, the invention also relates to a method for the diagnosis or the prognosis of metastasis in lung cancer, as well as to a method for determining the tendency to develop bone metastasis with respect to metastasis in other organs, which comprise determining the c-MAF gene expression level. Finally, the invention relates to the use of a c-MAF inhibitor as therapeutic target for treating the lung cancer.

15 Claims, 3 Drawing Sheets

Figure 1:
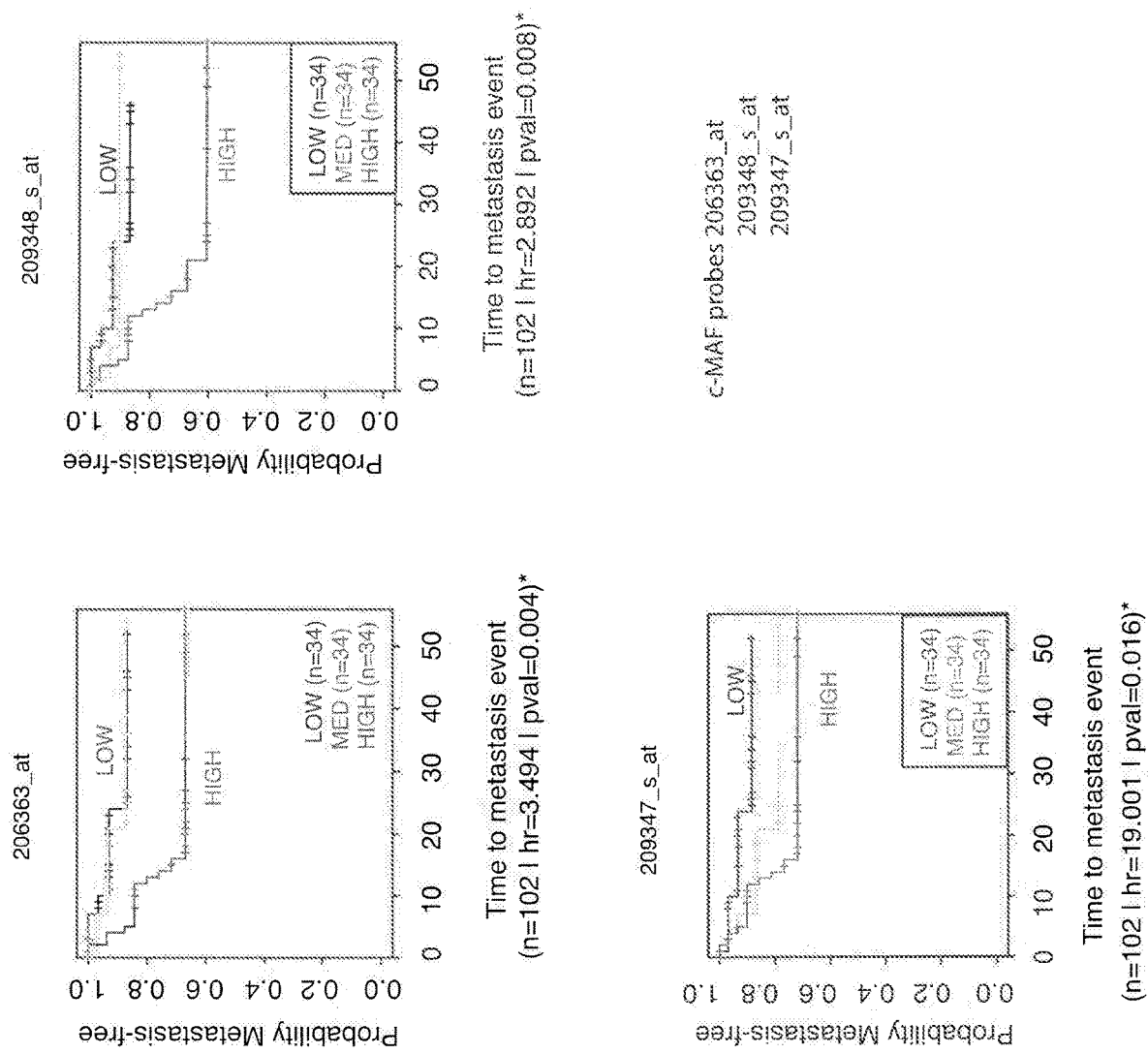

Specification includes a Sequence Listing.

(56) References Cited

U.S. PATENT DOCUMENTS

| | | |
|---|---|---|
| 2015/0152506 A1 | 6/2015 | Gomis et al. |
| 2015/0293100 A1 | 10/2015 | Gomis et al. |
| 2015/0362495 A1 | 12/2015 | Gomis et al. |
| 2016/0032399 A1 | 2/2016 | Gomis et al. |
| 2016/0032400 A1 | 2/2016 | Gomis et al. |
| 2016/0040247 A1 | 2/2016 | Gomis et al. |
| 2017/0002357 A1 | 1/2017 | Gomis et al. |
| 2017/0101683 A1 | 4/2017 | Gomis et al. |
| 2017/0121777 A1 | 5/2017 | Gomis et al. |
| 2017/0369589 A1 | 12/2017 | Gomis et al. |
| 2017/0370935 A1 | 12/2017 | Gomis et al. |
| 2019/0169693 A1 | 6/2019 | Gomis et al. |
| 2019/0242898 A1 | 8/2019 | Gomis et al. |
| 2019/0256922 A1 | 8/2019 | Gomis et al. |
| 2019/0269707 A1 | 9/2019 | Gregory et al. |
| 2019/0309299 A1 | 10/2019 | Gomis et al. |
| 2021/0137952 A1 | 5/2021 | Gregory et al. |
| 2021/0190784 A1 | 6/2021 | Gomis et al. |

FOREIGN PATENT DOCUMENTS

| | | | |
|---|---|---|---|
| WO | WO-8910134 A1 | 11/1989 | |
| WO | WO-9738117 A1 | 10/1997 | |
| WO | WO-0055126 A2 | 9/2000 | |
| WO | WO-0149288 A1 | 7/2001 | |
| WO | WO-03020278 A1 | 3/2003 | |
| WO | WO-03020721 A1 | 3/2003 | |
| WO | WO-03059249 A2 | 7/2003 | |
| WO | WO-2004000843 A1 | 12/2003 | |
| WO | WO-2004014888 A1 | 2/2004 | |
| WO | WO-2005026322 A2 | 3/2005 | |
| WO | WO-2005046731 A1 | 5/2005 | |
| WO | WO-2005063252 A1 | 7/2005 | |
| WO | WO-2005086891 A2 | 9/2005 | |
| WO | WO-2006012221 A2 | 2/2006 | |
| WO | WO-2006135436 A2 | 12/2006 | |
| WO | WO-2007038397 A2 | 4/2007 | |
| WO | WO-2007069090 A2 | 6/2007 | |
| WO | WO-2008098351 A1 | 8/2008 | |
| WO | WO-2008104543 A2 | 9/2008 | |
| WO | WO-2008142164 A2 | 11/2008 | |
| WO | WO-2009049410 A1 | 4/2009 | |
| WO | WO-2009146546 A1 | 12/2009 | |
| WO | WO-2012045905 A2 * | 4/2012 | ........... C07K 16/241 |
| WO | WO-2013153458 A2 | 10/2013 | |
| WO | WO-2013182912 A2 | 12/2013 | |
| WO | WO-2014057357 A2 | 4/2014 | |
| WO | WO-2014140896 A2 | 9/2014 | |
| WO | WO-2014140933 A2 | 9/2014 | |
| WO | WO-2014184679 A2 | 11/2014 | |
| WO | WO-2015052583 A2 | 4/2015 | |
| WO | WO-2015193737 A1 | 6/2015 | |
| WO | WO-2016092524 A1 | 6/2016 | |
| WO | WO-2017203468 A1 | 11/2017 | |
| WO | WO-2019102380 A1 | 5/2019 | |

OTHER PUBLICATIONS

Afinitor.com, "Afinitor (everolimus) tablets," accessed at http://www.afinitor.com/index.jsp?usertrack.filter_applied=true&Novald=4029462064338207963, accessed on Oct. 16, 2014, 5 pages.

Agilent Technologies, "Probes for Chromosome 16," accessed at http://genomics.agilent.com/productSearch.jsp?chr=16&start=79483700&end=79754340&_requestid=78075, accessed on Oct. 16, 2014, 3 pages.

Andrews, N.C., et al., "The ubiquitous subunit of erythroid transcription factor NF-E2 is a small basic-leucine zipper protein related to the v-maf oncogene," Proc Natl Acad Sci USA 90:11488-11492, National Academy of Sciences, United States (1993).

ARUP Laboratories, "Multiple Myeloma (MM) by FISH: Detection of Prognostically Significant Genomic Aberrations in Multiple Myeloma (MM) by Fluorescence in situ Hybridization (FISH)," accessed at http://aruplab.com, accessed on Oct. 16, 2014, 2 pages.

Baselga, J., et al., "Everolimus in postmenopausal hormone-receptor-positive advanced breast cancer," N Engl J Med 366(6):520-529, Massachusetts Medical Society, United States (Feb. 2012).

Bellahcéne, A., et al., "Expression of bone sialoprotein in human lung cancer," Calcif Tissue Int 61(3):183-188, Springer Verlag, United States (1997).

CGI Italia, "IGH/MAF Two Color, Two Fusion Translocation Probe," accessed at http://cancergeneticsitalia.com/dna-fish-probe/ighmaf/, accessed on Oct. 16, 2014, 1 page.

Chitale, D., et al., "An Integrated Genomic Analysis of Lung Cancer Reveals Loss of DUSP4 in EGFR-mutant Tumors," Oncogene 28(31):2773-2783, Nature Publishing Group, England (2009).

Choi, M., et al., "Genetic diagnosis by whole exome capture and massively parallel DNA sequencing," Proc Natl Acad Sci USA 106(45):19096-19101, National Academy of Sciences, United States (2009).

Christopherson, K.S., et al., "Ecdysteroid-dependent Regulation of Genes in Mammalian Cells by a Drosophila Ecdysone Receptor and Chimeric Transactivators," Proceedings of the National Academy of Sciences of the United States of America 89(14):6314-6318, National Academy of Sciences, United States (1992).

Creative Bioarray, "IGF/MAF Translation, Dual Fusion Probe," accessed at http://www.creative-bioarray.com/IGH-MAF-Translocation,-Dual-Fusion-Probe-FHPC-066-item-4707.htm, accessed on May 21, 2015, 2 pages.

Cytocell, "Oncology and Constitutional FISH Probe Catalogue 2012/2013," accessed at http://zentech.be/uploads/docs/products_info/prenatalogy/cytocell%202012-2013%20catalogue%5B3%5D.pdf, accessed on Oct. 16, 2014, 134 pages.

Zon, G., et al., "Oligonucleotide Analogues as Potential Chemotherapeutic Agents," Pharmaceutical Research 5(9):539-549, Kluwer Academic/Plenum Publishers, United States (Sep. 1988).

Co-pending U.S. Appl. No. 16/142,168, inventor Gomis, et al. (Not Published).

Office Action dated Feb. 9, 2017, in U.S. Appl. No. 14/405,724, inventor Gomis, Roger., et al., § 371(c) filing date May 26, 2015, 20 pages.

Dako, "SureFISH Probes," accessed at http://www.dako.com/us/ar42/psg42806000/baseproducts_surefish.htm?setCountry=true&purl=ar42/psg42806000/baseproducts_surefish.htm?undefined&submit=Accept%20country, accessed on Oct. 16, 2014, 2 pages.

Dannhardt, G. and Kiefer, W., "Cyclooygenase Inhibitors—Current Status and Future Prospects," European Journal of Medicinal Chemistry 36(2):109-126,Editions Scientifiques et Medicales Elsevier SAS, France (2001).

Demarest, J.F., et al., "Update on Aplaviroc: An HIV Entry Inhibitor Targeting CCR5," Retrovirology 2(Suppl 1):S13, BioMed Central, England (2005).

Dhesy-Thind, S., et al., "Use of Adjuvant Bisphosphonates and Other Bone-Modifying Agents in Breast Cancer: A Cancer Care Ontario and American Society of Clinical Oncology Clinical Practice Guideline," J Clin Oncol 35, American Society of Clinical Oncology, United States, 22 pages (published online before print Mar. 6, 2017).

Egholm, M., et al., "PNA Hybridizes to Complementary Oligonucleotides Obeying the Watson-crick Hydrogen-bonding Rules," Nature 365(6446):566-568, Nature Publishing Group, England (1993).

Ettenberg, S.A., et al., "BHQ880, A Novel Anti-DKK1 Neutralizing Antibody, Inhibits Tumor-Induced Osteolytic Bone Disease," Proceedings of the American Association for Cancer Resaerch 49:947, Abstract 3987,American Association for Cancer Research, United States (2008).

Eychene, A., et al., "A NewMAFia in Cancer," Nature Reviews Cancer 8(9):683-693, Nature Publishing Group, England (2008).

Fujiwara, K.T., et al., "Two New Members of the maf Oncogene Family, mafK and mafF, Encode Nuclear b-Zip Proteins Lacking Putative Trans-Activator Domain," Oncogene 8(9):2371-2380, Nature Publishing Group, England (1993).

Gabr, A.G., et al., "Erlotinib Prevents Experimental Metastases of Human Small Cell Lung Cancer Cells with No Epidermal Growth Factor Receptor Expression," Clinical & Experimental Metastasis 29(3):207-216, Kluwer Academic Publishers, Netherlands (Mar. 2012).

(56) References Cited

OTHER PUBLICATIONS

GenBank Database, NCBI Reference Sequence NG_016440, accessed on Jun. 20, 2013, accessed at http://www.ncbi.nlm.nih.gov/nuccore/NG_016440, 5 pages.
GenBank Database, NCBI Reference Sequence NM_005360.4, accessed on Oct. 16, 2014, accessed at http://www.ncbi.nlm.nih.gov/nuccore/NM_005360.4, 6 pages.
GenBank Database, NCBI Reference Sequence NM_001031804.2, accessed on Jun. 20, 2013, accessed at http://www.ncbi.nlm.nih.gov/nuccore/NM_001031804.2, 6 pages.
GenBank Database, NCBI Reference Sequence NT_010498.15, accessed on Oct. 16, 2014, accessed at http://www.ncbi.nlm.nih.gov/nuccore/NT_010498.15, 6 pages.
GenBank Database, NCBI Reference Sequence NT_010542.15, accessed on Oct. 16, 2014, accessed at http://www.ncbi.nlm.nih.gov/nuccore/NT_010542.15, 3 pages.
GenPept Database, NCBI Reference Sequence NP_005351.2, accessed on Apr. 3, 2015, accessed at http://www.ncbi.nlm.nih.gov/protein/NP_005351.2, 4 pages.
GenPept Database, NCBI Reference Sequence NP_001026974.1, accessed on Apr. 3, 2015, accessed at http://www.ncbi.nlm.nih.gov/protein/NP_001026974, 4 pages.
GenPept Database, UniProtKB/Swiss-Prot: O75444.2, accessed on Apr. 3, 2015, accessed at http://www.ncbi.nlm.nih.gov/protein/o75444, 6 pages.
Gentleman, R.C., et al., "Bioconductor: Open Software Development for Computational Biology and Bioinformatics," Genome Biology 5(10):R80, 16 pages, BioMed Central Ltd, England (2004).
Genycell Biotech, "FISH Mieloma Multiple," accessed at http://google.com/url?sa=t&rct=j&q=&esrc=s&source=web&cd=1&ved=CCQQFjAA&url=http%3A%2F%2Fwww.genycell.es%2Fimages%2Fproductos%2Fbrochures%2Flphmie6_86.ppt&ei=MhFYUOi3GKWH0QGIt4DoDw&usg=AFQjCNEqQMbT8vQGjJbi9riEf3IVgoFTFQ&sig2=V5IS8juEMVHBI8Mv2Xx_Ww, accessed on Oct. 16, 2014, 1 page.
Glas, A.S., et al., "The diagnostic odds ratio: a single indicator of test performance," *J Clin Epidemiol* 56(11):1129-1135, Elsevier Inc., England (2003).
Gossen, M. and Bujard, H., "Tight Control of Gene Expression in Mammalian Cells by Tetracycline-responsive Promoters," Proceedings of the National Academy of Sciences of the United States of America 89(12):5547-5551, National Academy of Sciences, United States (1992).
Gossen, M., et al., "Transcriptional Activation by Tetracyclines in Mammalian Cells," Science 268(5218):1766-1769, American Association for the Advancement of Science, United States (Jun. 1995).
Helene, C., "The Anti-gene Strategy: Control of Gene Expression by Triplex-forming-oligonucleotides," Anti-cancer Drug Design 6(6):569-584, Oxford University Press, United States (1991).
Henry, D.H., et al., "Randomized, Double-Blind Study of Denosumab Versus Zoledronic Acid in the Treatment of Bone Metastases in Patients with Advanced Cancer (Excluding Breast and Prostate Cancer) or Multiple Myeloma," Journal of Clinical Onocology 29(9):1125-1132, American Society of Clinical Oncology, United States (Mar. 2011).
Igarashi, K., et al., "Activity and Expression of Murine Small Maf Family Protein MafK," The Journal of Biological Chemistry 270(13):7615-7624, The American Society for Biochemistry and Molecular Biology, Inc., United States (1995).
International Preliminary Report on Patentability and Written Opinion for International Application No. PCT/IB2013/001859, The International Bureau of WIPO, Geneva, Switzerland, dated Dec. 9, 2014, 10 pages.
International Search Report for Application No. PCT/IB2013/001859, dated Dec. 3, 2013, 6 pages.
Kataoka, K., et al., "Small Maf Proteins Heterodimerize with Fos and May Act as Competitive Repressors of the NF-E2 Transcription Factor," Molecular and Cellular Biology 15(4):2180-2190, American Society for Microbiology, United States (1995).
Kataoka, K., et al., "Transactivation Activity of Maf Nuclear Oncoprotein is Modulated by Jun, Fos and Small Maf Proteins," Oncogene 12:53-62, Stockton Press, England (1996).
Kaykas, A. and Moon, R.T., "A plasmid-based system for expressing small interfering RNA libraries in mammalian cells," BMC Cell Biology 5:16:1-11, BioMed Central Ltd., England (2004).
Kohler, G. and Milstein, C., "Continuous Cultures of Fused Cells Secreting Antibody of Predefined Specificity," Nature 256(5517):495-497, Macmillan Journals Ltd., England (Aug. 1975).
Kuritzkes, D.R., "HIV-1 Entry Inhibitors: An Overview," Current Opinion in HIV and AIDS 4(2):82-87, Lippincott Williams & Wilkins, United States (2009).
Lee, N.S., et al., "Expression of small interfering RNAs targeted against HIV-1 rev transcripts in human cells," Nature Biotechnology 20(5):500-505, Nature American Publishing, United States (2002).
Leica Biosystems, "Kreatech™ Fish Probes," accessed at http://leicabiosystems.com/ihc-ish/kreatech-fish-probes/, accessed on Oct. 16, 2014, 2 pages.
Lemaitre, M., et al., "Specific Antiviral Activity of a Poly (L-Lysine)-Conjugated Oligodeoxyribonucleotide Sequence Complementary to Vesicular Stomatitis Virus N Protein mRNA Initiation Site," Proceedings of the National Academy of Sciences 84(3):648-652, National Academy of Science, United States (Feb. 1987).
Letsinger, R.L., et al., "Cholesteryl-conjugated Oligonucleotides: Synthesis, Properties, and activity as Inhibitors of Replication of Human Immunodeficiency Virus in Cell Culture," Proceedings of the National Academy of Sciences USA 86(17):6553-6556, National Academy of Science, United States (Sep. 1989).
Lindgren, M., et al., "Cell-penetrating Peptides," Trends in Pharmacological Sciences 21(3):99-103, Elsevier, England (2000).
Lundberg, M., et al., "Cell Surface Adherence and Endocytosis of Protein Transduction Domains," Molecular Therapy 8(1):143-150, Academic Press, United States (2003).
Maisano, R., et al., "Novel Therapeutic Approaches to Cancer Patients with Bone Metastasis," Critical Reviews in Oncology/Hematology 40(3):239-250, Elsevier Science Ireland Ltd., Ireland (2001).
MetaSystems, "24XCyte," http://metasystems-international.com/index.php?option=com_joodb&view=article&joobase=5*id=12%3Ad-5029-100-og<emid=272, accessed on Oct. 16, 2014, 2 pages.
Mystakidou, K., et al., "Randomized, Open Label, Prospective Study on the Effect of Zoledronic Acid on the Prevention of Bone Metastases in Patients with Recurrent Solid Tumors That Did Not Present with Bone Metastases at Baseline," Medical Oncology 22(2):195-201, Humana Press Inc., United States (2005).
Ng, P.C. and Kirkness, E.F., "Whole genome sequencing," *Methods Mol Biol* 628:215-226, Springer Science+Business Media, LLC, Netherlands (2010).
Nguyen, D.X. and Massague, J., "Genetic Determinants of Cancer Metastasis," Nature Reviews Genetics 8(5):341-352, Nature Publishing Group, England (2007).
Nguyen, D.X., et al., "Metastasis: From Dissemination to Organ-Specific Colonization," Nature Reviews Cancer 9(4):274-284, Macmillan Publishers Limited, England (2009).
No, D., et al., "Ecdysone-inducible Gene Expression in Mammalian Cells and Transgenic Mice," Proceedings of the National Academy of Sciences USA 93(8):3346-3351, National Academy of Sciences, United States (Apr. 1996).
Pageau, S.C., "Denosumab," Monoclonal Antibodies 1(3):210-215, Landes Bioscience, United States (2009).
Paik, S., et al., "A Multigene Assay to Predict Recurrence of Tamoxifen-Treated, Node-Negative Breast Cancer," The New England Journal of Medicine 351(27):2817-2826, Massachusetts Medical Society, United States (2004).
Perry-O'Keefe, H., et al., "Peptide Nucleic Acid Pre-gel Hybridization: an Alternative to Southern Hybridization," Proceedings of the National Academy of Sciences of the United States of America 93(25):14670-14675, National Academy of Sciences, United States (1996).
Rivera, V.M., et al., "A Humanized System for Pharmacologic Control of Gene Expression," Nature Medicine 2(9):1028-1032, Nature Publishing Company, United States (Sep. 1996).

(56) References Cited

OTHER PUBLICATIONS

Rossi, F.M. and Blau, H.M., "Recent Advances in Inducible Gene Expression Systems," Current Opinion in Biotechnology 9(5):451-456, Elsevier, England (1998).
Rossi, J.J., "Practical Ribozymes. Making Ribozymes Work in Cells," Current Biology 4(5):469-471, Elsevier, Netherlands (May 1994).
Rotstein, D.M., et al., "Spiropiperidine CCR5 Antagonists," Bioorganic and Medicinal Chemistry Letters 19(18):5401-5406, Elsevier Ltd., England (2009).
Schwarze, S.R. and Dowdy, S.F., "In Vivo Protein Transduction: Intracellular Delivery of Biologically Active Proteins, Compounds and DNA," Trends in Pharmacological Sciences 21(2):45-48, Elsevier, England (2000).
Sen, B. and Johnson, F.M., "Regulation of SRC Family Kinases in Human Cancers," Journal of Signal Transduction 2011 (865819):1-14, Hindawi Publishing Corporation, United States (Apr. 2011).
Snyder, E.L. and Dowdy, S.F., "Cell Penetrating Peptides in Drug Delivery," Pharmaceutical Research 21(3):389-393, Kluwer Academic/Plenum Publishers, United States (2004).
Stein, C.A. and Cohen, J.S., "Oligodeoxynucleotides as Inhibitors of Gene Expression: a Review," Cancer Research 48(10):2659-2668, American Association for Cancer Research, United States (1988).
Suhr, S.T., et al., "High Level Transactivation by a Modified Bombyx Ecdysone Receptor in Mammalian Cells Without Exogenous Retinoid X Receptor," Proceedings of the National Academy of Sciences of the United States of America 95(14):7999-8004, National Academy of Sciences, United States (1998).
Swennenhuis, J.F., et al., "Construction of Repeat-Free Fluorescence in situ Hybridization Probes," Nucleic Acids Research 40(3):e20:1-8, Oxford University Press, England (Feb. 2012).
Templeton, S.N., "Liposomal Delivery of Nucleic Acids in Vivo," DNA and Cell Biology 21(12):857-867, Mary Ann Liebert, United States (2002).
Théry, C., et al., "Isolation and characterization of exosomes from cell culture supernatants and biological fluids," *Curr Protoc Cell Biol Chapter* 3:3.22.1-3.22.29, John Wiley & Sons, Inc., United States (2006).
Tran, N., et al., "Expressing functional siRNAs in mammalian cells using convergent transcription," BMC Biotechnology 3:21:1-9, BioMed Central Ltd., England (2003).
Van Der Krol, A.R., et al., "Modulation of Eukaryotic Gene Expression by Complementary RNA or DNA Sequences," Biotechniques 6(10):958-976, Informa Healthcare, United States (Nov. 1988).
Velasco-Velazquez, M., et al., "CCR5 Antagonist Blocks Metastasis of Basal Breast Cancer Cells," Cancer Research 72(15):3839-3850, American Association for Cancer Research, United States (Aug. 2012).
Wang, J., et al., "Stable and controllable RNA interference: Investigating the physiological function of glutathionylated actin," Proceedings of the National Academy of Sciences of USA 100(9):5103-5106, National Academy of Sciences, United States (2003).
Zaug, A.J., et al., "A Labile Phosphodiester Bond at the Ligation Junction in a Circular Intervening Sequence RNA," Science 224(4649):574-578, American Association for the Advancement of Science, United States (1984).
Zeiss, "Fish Probes: XL Haematology," accessed at https://microshop.zeiss.com/?440675675dedc6&1=en&p=uk&f=r&i=5000&o=&h=25&n=1&sd=000000-528-231-uk, accessed on Oct. 16, 2014, 3 pages.
Zhang, X.H-F., et al., "Latent Bone Metastasis in Breast Cancer Tied to Src-Dependent Survival Signals," Cancer Cell 16(1):67-78, Cell Press, United States (2009).
Zheng, L., et al., "An approach to genomewide screens of expressed small interfering RNAs in mammalian cells," Proceedings of the National Academy of Sciences of USA 101(1):135-140, National Academy of Sciences, United States (2004).
Zhou, H., et al., "Updates of mTOR Inhibitors," Anticancer Agents in Medicinal Chemistry 10(7):571-581, Bentham Science Publishers, Netherlands (2010).
Zometa®, "About Zometa® (zoledronic acid) 4 mg/5 mL Injection," accessed at http://www.us.zometa.com/index.jsp?usertrack.filter_applied=true&Novald=29353769344676433633, accessed on Apr. 3, 2015, 2 pages.
Chames, P., et al., "Therapeutic antibodies: successes, limitations and hopes for the future," British Journal of Pharmacology 157:220-233, Wiley Blackwell, United States (2009).
Gura, T., et al., "Systems for Identifying New Drugs are Often Faulty," Science 278(5340):1041-1042, American Association for the Advancement of Science, United States (1997).
Kaiser, J., "First Pass at Cancer Genome Reveals Complex Landscape," Science 313(5792):1370, American Association for the Advancement of Science, United States (2006).
Silva, S.C., et al., "Bone-targeted agents in the treatment of lung cancer," Ther Adv Med Oncol 7(4): 219-228, Sage Journals, United States (2015).
Office Action dated Sep. 20, 2017, in U.S. Appl. No. 14/405,724, inventor Gomis, Roger., et al., § 371(c) filed May 26, 2015, 11 pages.
Co-pending Application, U.S. Appl. No. 15/944,499, inventors Gomis, R., et al., filed Apr. 3, 2018 (Not Published).
Co-pending Application, U.S. Appl. No. 15/944,510, inventors Gomis R., et al., filed Apr. 3, 2018 (Not Published).
Co-pending Application, U.S. Appl. No. 15/955,790, Inventors Gomis, R., et al., filed Apr. 18, 2018 (Not Published).
Co-pending U.S. Appl. No. 16/303,945, inventor Gomis, et al., filing to be assigned (Not Published).
Co-pending U.S. Appl. No. 16/028,530, inventor Gomis, et al., filed Jul. 6, 2018 (Not Published).
Co-pending U.S. Appl. No. 16/134,449, filed Sep. 18, 2018 (Not Published).
European Search Report for EP Application No. 18206025, Munich, Germany, dated Jan. 16, 2019.
Suominen, M.I., et al., "Alpharadin Inhibits Osteoclast Differentiation in Vitro and Progression of Established Breast Cancer Bone Metastases in Vivo," Abstract No. 2664, Pharmatest, Bayer HealthCare Pharmaceuticals, Poster presented at the 102nd Annual Meeting of the American Association for Cancer Research, Apr. 2-6, 2011, Orlando, Florida, USA, 2 pages.
Drake, M. T., et al., "Bisphosphonates: Mechanism of Action and Role in Clinical Practice," *Mayo Clinic Proceedings* 83(9):1032-1045, Elsevier on behalf of the Mayo Clinic, United States (2008).
Co-pending Application, U.S. Appl. No. 17/241,571, inventors Gomis, R., et al., filed Apr. 27, 2021 (Not Yet Published).
Co-pending Application, U.S. Appl. No. 17/339,024, inventor Gomis, R., filed Jun. 4, 2021 (Not Yet Published).
Co-pending Application, U.S. Appl. No. 17/353,013, inventors Gomis, R., et al., filed Jun. 21, 2021 (Not Yet Published).

* cited by examiner

METHOD FOR THE DIAGNOSIS, PROGNOSIS AND TREATMENT OF LUNG CANCER METASTASIS

CROSS-REFERENCE TO RELATED APPLICATIONS

This application is a divisional of U.S. application Ser. No. 14/405,724, issued as U.S. Pat. No. 10,006,091, which is the National Stage of International Application Number PCT/IB2013/001859, filed Jun. 6, 2013, which claims the benefit of U.S. Provisional Patent Application Ser. No. 61/656,372, filed on Jun. 6, 2012, and incorporated herein by reference in their entirety.

REFERENCE TO SEQUENCE LISTING

The content of the electronically submitted sequence listing ("3190_0020002_SL", 48,430 bytes, created on May 16, 2018) filed with the application is incorporated herein by reference in its entirety.

BACKGROUND OF THE INVENTION

Field of the Invention

The present invention relates to the diagnosis or the prognosis of metastasis, in particular bone metastasis, in lung cancer based on determining if the c-MAF gene is amplified in a primary tumor sample. Likewise, the invention also relates to a method for the diagnosis or the prognosis of metastasis in lung cancer, in particular/bone metastasis, as well as to a method for designing a customized therapy in a subject with lung cancer, which comprises determining the c-MAF gene expression level. Finally, the invention relates to the use of a c-MAF inhibitor as therapeutic target for the treatment of lung cancer metastasis, in particular bone metastasis.

Background Art

Metastasis, a complex process caused by elaborate interactions between tumor cells and the surrounding normal tissues in different vital organs, accounts for 90 percent of all cancer deaths in patients with solid tumors. The molecular and cellular mechanisms that lead primary tumors to form metastases must be understood in order to better address this major life-threatening problem. The identification of metastasis genes and mechanisms is essential for understanding the basic biology of this lethal condition and its implications for clinical practice. Previous work provided a sense of the complexity of the metastasis process, but it failed to explain how and why metastasis occurs, what mechanisms make metastasis a tissue-specific process, what events allow dormant metastases to become active and lethal many years after removal of a primary tumor, and what metastasis-mediating genes would eventually constitute worthy diagnostic markers and therapeutic targets.

Lung Bone-Specific Metastasis

Lung cancer is a disease characterized by uncontrolled cell growth in tissues of the lung. If left untreated, this growth can spread beyond the lung in a process called metastasis into nearby tissue and, eventually, into other parts of the body. Most cancers that start in lung, known as primary lung cancers, are carcinomas that derive from epithelial cells. Worldwide, lung cancer is the most common cause of cancer-related death in men and women, and is responsible for 1.3 million deaths annually, as of 2004. The most common symptoms are shortness of breath, coughing (including coughing up blood), and weight loss.

Lung cancers consist of four major types of lung cancer and multiple minor or rare forms. For clinico-pathological reasons they are often divided into the broad categories of small-cell lung cancer (SCLC), also called oat cell cancer, and non-small-cell lung cancer (NSCLC). NSCLC is further divided into three major types, squamous, cell carcinoma (SCC), adenocarcinoma and large cell carcinomas. Because large cell carcinomas might represent poorly or undifferentiated forms of the other types of cancers, it is a vaguely defined entity, and criteria for diagnosis vary widely. The most common cause of lung cancer is long-term exposure to tobacco smoke. Nonsmokers account for 15% of lung cancer cases, and these cases are often attributed to a combination of genetic factors, radon gas, asbestos, and air pollution including secondhand smoke.

Similar to many other cancers, lung cancer is initiated by activation of oncogenes or inactivation of tumor suppressor genes. Oncogenes are genes that are believed to make people more susceptible to cancer. Proto-oncogenes are believed to turn into oncogenes when exposed to particular carcinogens. Mutations in the K-ras proto-oncogene are responsible for 10-30% of lung adenocarcinomas. The epidermal growth factor receptor (EGFR) regulates cell proliferation, apoptosis, angiogenesis, and tumor invasion. Mutations and amplification of EGFR are common in non-small-cell lung cancer and provide the basis for treatment with EGFR-inhibitors. Her2/neu is affected less frequently. Chromosomal damage can lead to loss of heterozygosity. This can cause inactivation of tumor suppressor genes. Damage to chromosomes 3p, 5q, 13q, and 17p are particularly common in small-cell lung carcinoma. The p53 tumor suppressor gene, located on chromosome 17p, is affected in 60-75% of cases. Other genes that are often mutated or amplified are c-MET, NKX2-1, LKB1, PIK3CA, and BRAF.

Several genetic polymorphisms are associated with lung cancer. These include polymorphisms in genes coding for interleukin-1, cytochrome P450, apoptosis promoters such as caspase-8, and DNA repair molecules such as XRCC1. People with these polymorphisms are more likely to develop lung cancer after exposure to carcinogens.

Classification

Lung cancers are classified according to histological type. This classification has important implications for clinical management and prognosis of the disease. The vast majority of lung cancers are carcinomas—malignancies that arise from epithelial cells. The two most prevalent histological types of lung carcinoma, categorized by the size and appearance of the malignant cells seen by a histopathologist under a microscope, are non-small-cell and small-cell lung carcinoma. The non-small-cell type is the most prevalent by far.

Cancer found outside of the lung may be determined to have arisen within the lung, as lung cancers that metastasize, i.e. spread, often retain a cell marker profile that allow a pathologist to say, with a good deal of certainty, that the tumor arose from the lung, i.e. is a primary lung cancer. Primary lung cancers of adenocarcinoma histology typically have nuclear immunostaining with TTF-1.

Non-Small-Cell Lung Carcinoma

The non-small-cell lung carcinomas (NSCLC) are grouped together because their prognosis and management are similar. There are three main sub-types: squamous cell lung carcinoma; adenocarcinoma; and large-cell lung carcinoma.

Accounting for 25% of lung cancers, squamous cell lung carcinoma usually starts near a central bronchus. A hollow cavity and associated necrosis are commonly found at the center of the tumor. Well-differentiated squamous cell lung cancers often grow more slowly than other cancer types.

Adenocarcinoma accounts for 40% of non-small-cell lung cancers. It usually originates in peripheral lung tissue. Most cases of adenocarcinoma are associated with smoking; however, among people who have never-smoked ("never-smokers"), adenocarcinoma is the most common form of lung cancer. A subtype of adenocarcinoma, the bronchioloalveolar carcinoma, is more common in female never-smokers, and may have different responses to treatment.

Small-Cell Lung Carcinoma

Small-cell lung carcinoma (SCLC) is less common. It was formerly referred to as "oat-cell" carcinoma. Most cases arise in the larger airways (primary and secondary bronchi) and grow rapidly, becoming quite large. The small cells contain dense neurosecretory granules (vesicles containing neuroendocrinehormones), which give this tumor an endocrine/paraneoplastic syndrome association. While initially more sensitive to chemotherapy and radiation, it is often metastatic at presentation, and ultimately carries a worse prognosis. Small-cell lung cancers have long been dichotomously staged into limited and extensive stage disease. This type of lung cancer is strongly associated with smoking.

Prognosis

Prognostic factors in non-small-cell lung cancer include presence or absence of pulmonary symptoms, tumor size, cell type (histology), degree of spread (stage) and metastases to multiple lymph nodes, and vascular invasion. For patients with inoperable disease, prognosis is adversely affected by poor performance status and weight loss of more than 10%. Prognostic factors in small-cell lung cancer include performance status, gender, stage of disease, and involvement of the central nervous system or liver at the time of diagnosis.

For non-small-cell lung carcinoma (NSCLC), prognosis is generally poor. Following complete surgical resection of stage IA disease, five-year survival is 61%. With stage IB disease, five-year survival is 57%. The five-year survival rate of patients with stage IV NSCLC is about 1%.

For small-cell lung carcinoma, prognosis is also generally poor. The overall five-year survival for patients with SCLC is about 5%. Patients with extensive-stage SCLC have an average five-year survival rate of less than 1%. The median survival time for limited-stage disease is 20 months, with a five-year survival rate of 20%.

According to data provided by the National Cancer Institute, the median age at diagnosis of lung cancer in the United States is 70 years, and the median age at death is 72 years. In the US, people with medical insurance are more likely to have a better outcome.

Metastasis

Primary lung cancers themselves most commonly metastasize to the adrenal glands, liver, brain, and bone.

Skeletal metastasis occurs in advanced-stage lung cancer and they confer a high level of morbidity. At first diagnosis of bone metastasis disease therapeutic intervention will usually involve systemic chemotherapy, radiotherapy and bisphophonates, which are mostly palliative options with the intention of reducing pain.

In healthy skeletal bone, an equal balance of new bone matrix formation and old bone matrix resorption is achieved via coordinated activity of bone-degrading osteoclasts and bone-forming osteoblasts. During metastasis bone disease, the normal balance of bone resorption and formation is disrupted by the homotypic and heterotypic cell-cell interactions that occur between invading tumor cells, osteoblasts and ostoclasts. Most patients with secondary bone tumors—including those associated with lung cancer present with osteolytic lesions. Therefore, most treatment strategies in current use or under evaluation in metastasis bone disease have been designed to protect the bone matrix from increased, bone degrading activity of osteoclasts. Bone metastasis osteolytic lesions of the lung are a common feature with those of the breast, as opposed to prostate cancer. In the latter, an additional complication present in castration-resistant prostate cancer and metastasis bone disease are osteosclerotic lesions—also known as bone-forming or osteoblastic lesions—or a combination of both, osteolytic and osteosclerotic lesions—also referred to as mixed lesions. Osteosclerotic lesions are typified by bone deposits with multiple layers of poorly organized type-I collagen fibrils that have a woven appearance and reduced mechanical strength. Based on the common phenotypic features of lung and breast cancer bone metastasis is likely that the process underlines similar molecular mechanisms.

Lung cancer cells preserve, among each subtype, genome-aberration-induced transcriptional changes with high fidelity. The resulting dominant genes will reveal molecular events that predict the metastatic outcome despite the existence of substantial genomic, transcriptional, translational, and biological heterogeneity in the overall system. However, it is unknown whether the developmental history of a cancer would result in different or common mediators of site-specific metastasis. Predisposing factors related to the cell of origin may engender different rate-limiting barriers during metastasic progression. The present patent aims to set the stage for a detailed new prognostic factor to predict metastasis to the bone and their potential value as a therapeutic target.

The fact that most of the patients with solid tumor cancer die after metastasis means that it is crucial to understand the molecular and cellular mechanisms allowing a tumor to metastasize. Recent publications have demonstrated how the metastasis is caused by means of complex yet little known mechanisms and also how the different metastatic cell types have a tropism towards specific organs. These tissue specific metastatic cells have a series of acquired functions allowing them to colonize specific organs.

However, there are no genetic markers, in the state of the art, which allow the diagnosis and/or the prognosis of whether a patient who suffers a specific lung cancer, such as NSCLC lung cancer, will or will not suffer metastasis, thus a suitable therapy being able to be applied to the subject suffering said cancer. Therefore, there is the need of identifying new markers which allow diagnosing the presence of metastasis in subjects suffering lung cancer and/or predicting the probability of a subject suffering lung cancer to develop metastasis, in particular bone metastasis. The identification of new prognosis factors will serve as a guide in selecting the most suitable treatments.

Identification of markers that predict bone metastasis would provide a preventive therapeutic opportunity by imposing restrictions to the spreading and colonization of bone metastatic tissue by lung cells and delay or transform a lethal condition. The inventors identified c-MAF and 16q22-24 genomic gain, as a bona fide associated lung cancer bone metastasis gene and genomic alteration, in a preferred embodiment osteolytic prostate bone metastasis.

BRIEF SUMMARY OF THE INVENTION

The present inventors have determined that identifying the balance of signals that affect disseminated lung cancer cell metastasis, in particular bone metastasis, would provide valuable information to establish the prognosis of, and for preventive therapeutic intervention against, the disease. The inventors identified MAF and the 16q22-24 genomic gain as playing a role in driving lung-to-bone metastasis lesions, in particular osteolytic bone metastasis.

The present inventors have identified c-MAF as a marker associated with a greater tendency of lung cancer to cause metastasis and, particularly, bone metastasis. MAF overexpression appears to be due to an amplification of the locus 16q22-q24 in which the c-MAF gene is located.

c-MAF expression levels were studied in two patient cohorts. The first cohort contained the expression profiles and the clinical notes of primary tumors from patients with lung cancer. The second patient cohort was in the form of a tissue microarray composed of lung primary tumor biopsies, including 9 tumors that developed metastasis to the bone, 16 tumors that developed metastasis to other sites except bone and had a minimum clinical follow up of 5 years and 49 lung primary tumors that never developed metastasis with a minimum clinical follow up of 5 years, the c-MAF gene (mRNA) and protein expression in tumor cells and biopsy correlates positively with different clinical parameters, included the recurrence, metastasis, bone metastasis and overall survival being observed. Furthermore, these studies showed the role of c-MAF as marker for prognosis and as a target gene in lung cancer metastasis, particularly bone metastasis. Likewise, the inventors have associated the amplification of the locus 16q22-q24, including the c-MAF gene, with the presence of metastasis, in particular bone metastasis, in subjects with lung cancer.

Thus, in a first aspect, the invention relates to an vitro method for the diagnosis of metastasis in a subject with lung cancer and/or the prognosis of the tendency to develop metastasis, in particular bone metastasis, in a subject with lung cancer, which comprises:
  (i) quantifying the c-MAF gene expression level or 16q22-24 copy number gain in a tumor sample of said subject; and
  (ii) comparing the expression level or copies previously obtained with the expression level of said gene in a control sample;
wherein if the expression level of said gene is increased or genomic region amplified with respect to the expression level of said gene in the control sample, then said subject has a positive diagnosis for metastasis or a greater tendency to develop metastasis, in particular bone metastasis.

In a second aspect, the invention relates to an in vitro method for designing a customized therapy for a subject with lung cancer, which comprises:
  (i) quantifying the c-MAF gene expression level or 16q22-24 copy number gain in a tumor sample of said subject; and
  (ii) comparing the expression level previously obtained with the expression level of said gene in a control sample;
wherein if the expression level is increased or 16q22-24 copy number gained with respect to the expression level of said gene in the control sample, then said subject is susceptible to receive a therapy aiming to prevent an/or treat the metastasis. In a particular aspect of this method, the subject is then administered at least one therapy that prevents, inhibits and/or treats the bone metastasis. If the expression level is not increased or 16q22-24 copy number is not gained with respect to said reference value, then said subject is not susceptible to receive a therapy aiming to prevent, inhibit and/or treat the bone metastasis. In a particular aspect of this method, the subject is then not administered at least one therapy that prevents, inhibits and/or treats the bone metastasis. In some aspects, the reference value is the c-MAF gene expression level in a sample of lung cancer from a subject who has not suffered metastasis. In some aspects, the lung cancer, is SCL. In some embodiments, the lung cancer is NSCLC. In some aspects, the lung cancer is lung adenocarcinoma.

In a third aspect, the invention relates to an in vitro method for designing a customized therapy for a subject with lung cancer with bone metastasis, which comprises:
  (i) quantifying the c-MAF gene expression level or 16q22-24 copy number gain in a bone metastatic tumor sample of said subject; and
  (ii) comparing the expression level obtained in step (i) with the expression level of said gene in a control sample;
wherein if the c-MAF gene expression level or 16q22-24 copy number gain is increased with respect to the expression level of said gene in the control sample, then said subject is susceptible to receive a therapy aiming to prevent the bone degradation. In a particular aspect of this method, the subject is then administered at least one therapy that prevents, inhibits and/or treats the bone metastasis. If the c-MAF gene expression level is not increased or 16q22-24 copy number is not gained with respect to said reference value, then said subject is not susceptible to receive a therapy for preventing the bone degradation. In a particular aspect of this method, the subject is then not administered at least one therapy that prevents, inhibits and/or treats the bone metastasis.

In a fourth aspect, the invention relates to an in vitro method for the diagnosis of metastasis in a subject with lung cancer and/or for the prognosis of the tendency to develop metastasis in a subject with lung cancer which comprises determining if the c-MAF gene is amplified or translocated in a tumor tissue sample of said subject; wherein if said gene is amplified with respect to a control sample, then said subject has a positive diagnosis for metastasis or a greater tendency to develop metastasis. In a particular aspect of this method, the subject is then administered at least one therapy that prevents or inhibits the bone metastasis. In a particular aspect of this method, if the c-MAF gene is not amplified or translocated in a tumor tissue sample of said subject, the subject is then not administered at least one therapy that prevents, inhibits and/or treats the bone metastasis. In a particular aspect, an above average expression level of the c-MAF is indicative of an increased risk of bone metastasis and this risk is proportional to the levels of c-MAF expression. In a particular aspect, if the expression level of the c-MAF is above the average plus one standard deviation with respect to the average level, then it can be concluded that said subject has a greater tendency to develop early bone metastasis.

In another aspect, the invention relates to an in vitro method for predicting the clinical outcome of a patient suffering lung cancer, which comprises determining if the c-MAF gene is amplified in a sample of said subject relative to a reference gene copy number wherein an amplification of the c-MAF gene with respect to said reference gene copy number is indicative of a poor clinical outcome. In a particular aspect of this method, the subject is then administered at least one therapy that prevents, inhibits and/or treats the bone metastasis. If such amplification is not observed then the subject is then not administered at least one therapy that prevents, inhibits and/or treats the bone metastasis. In another embodiment of the seventh aspect, the invention relates to an in vitro method for predicting the clinical outcome of a patient suffering lung cancer which comprises determining if the c-MAF gene is translocated in a sample of said subject wherein a translocation of the c-MAF gene (e.g. t(14,16)) is indicative of a poor clinical outcome. In some embodiments, the invention relates to designing a customized therapy for patients with the amplification or translocation of c-MAF. In some embodiments, the customized therapy is at least one therapeutic drug that prevents, inhibits and/or treats the bone metastasis.

In a fifth aspect, the invention relates to the use of a c-MAF inhibitory agent in the preparation of a medicinal product for treating and/or preventing lung cancer metastasis, in particular bone metastasis. In another aspect, the invention relates to a c-MAF inhibitory agent for use in the prevention of bone metastasis from lung cancer. In some aspects, the invention relates to a a c-MAF inhibitory agent for use in avoiding or preventing bone degradation.

In another aspect, the invention relates to the use of an agent capable of avoiding or preventing bone degradation in the preparation of a medicinal product for the treatment of bone metastasis in a subject suffering lung cancer and having elevated c-MAF levels or 16q22-24 copy number gain in a metastatic tumor tissue sample with respect to a control sample.

In another aspect, the invention relates to a kit for predicting bone metastasis of a lung cancer in a subject suffering from said cancer, the kit comprising: a) means for quantifying the expression level of c-MAF in a sample of said subject; and b) means for comparing the quantified level of expression of c-MAF in said sample to a reference c-MAF expression level. The invention also relates to the use of such kit to predict bone metastasis of a lung cancer in a subject suffering from said cancer. In one embodiment, the subject is then administered or not administered at least one therapy that prevents, inhibits and/or treats the bone metastasis biased on the results of using the kit.

In another aspect, the invention relates to a kit for predicting bone metastasis of a lung cancer in a subject suffering from said cancer, the kit comprising: a) means for quantifying the amplification of c-MAF gene, 16q23 or 16q22-24 locus amplification or translocation in a sample of said subject; and b) means for comparing the amplified level of c-MAF gene, 16q23 or 16q22-24 locus amplification or translocation in said sample to a reference. In another aspect, the invention relates to a kit for predicting the clinical outcome of a subject suffering from bone metastasis from a lung cancer, the kit comprising: a) means for quantifying the expression level of c-MAF or the 16q23 or 16q22-24 locus amplification or translocation in a sample of said subject; and b) means for comparing the quantified expression level of c-MAF or the 16q23 or 16q22-24 locus amplification or translocation in said sample to a reference c-MAF expression level or 16q23 or 16q22-24 locus. The invention also relates to the use of such kit to predict the clinical outcome of a subject suffering from bone metastasis from a lung cancer. In one embodiment, the subject is then administered or not administered at least one therapy that prevents, inhibits and/or treats the bone metastasis based on the results of using the kit.

In another aspect, the invention relates to a kit for determining a therapy for a subject suffering from lung cancer, the kit comprising: a) means for quantifying the expression level of c-MAF or the 16q23 or 16q22-24 locus amplification or translocation in a sample of said subject; b) means for comparing, the quantified expression level of c-MAF in said sample to a reference c-MAF expression level or 16q23 or 16q22-24 locus; and c) means for determining a therapy for preventing and/or reducing bone metastasis in said subject based on the comparison of the quantified expression level to the reference expression level. The invention also relates to the use of such kit to determine a therapy for a subject suffering from lung cancer. In one embodiment, the subject is then administered or not administered at least one therapy that prevents, inhibits and/or treats the bone metastasis based on the results of using the kit.

In another aspect, the invention relates to a kit comprising: i) a reagent for quantifying the expression level of c-MAF or the 16q23 or 16q22-24 locus amplification or translocation in a sample of a subject suffering from lung cancer, and ii) one or more c-MAF gene expression level or the 16q23 or 16q22-24 locus amplification or translocation indices that have been predetermined to/correlate with the risk of bone metastasis. The invention also relates to the use of such kit to predict bone metastasis of a lung cancer in a subject suffering from said cancer. In one embodiment, the subject is then administered or not administered at least one therapy that prevents, inhibits and/or treats the bone metastasis based on the results of using the kit.

In another aspect, the invention relates to an in vitro method for typing a sample of a subject suffering from lung cancer, the method comprising:
a) providing a sample from said subject;
b) quantifying the expression level of c-MAF or the 16q23 or 16q22-24 locus amplification or translocation in said sample;
c) typing said sample by comparing the quantified expression level of c-MAF or the 16q23 or 16q22-24 locus amplification or translocation to a predetermined reference level of c-MAF expression or 16q23 or 16q22-24 locus number of copies;

wherein said typing provides prognostic information related to the risk of bone metastasis in said subject. In one embodiment, the subject is administered or not administered at least one therapeutic agent based on the prognostic information provided by the typing.

In another aspect, the invention relates to a method for preventing or reducing the risk of bone metastasis in a subject suffering from lung cancer, said method comprising administering to said subject an agent that prevents or reduces bone metastasis, wherein said agent is administered in accordance with a treatment regimen determined from quantifying the expression level of c-MAF or the 16q23 or 16q22-24 locus amplification or translocation in said subject.

In another aspect, the invention relates to a method of classifying a subject suffering from lung cancer into a cohort, the method comprising: a) determining the expression level of c-MAF or the 16q23 or 16q22-24 locus amplification or translocation in a sample of said subject; b) comparing the expression level of c-MAF in said sample to a predetermined reference level of c-MAF expression or a normal genome; and c) classifying said subject into a cohort based on said expression level of c-MAF or the 16q23 or 16q22-24 locus amplification or translocation in the sample. In one embodiment, the method is used to identify patients predicted to have an earlier manifestation of symptoms of bone metastasis. In a particular aspect, the cohort is used for conducting a clinical trial.

BRIEF DESCRIPTION OF THE DRAWINGS/FIGURES

FIG. 1: Gene expression of c-MAF in lung primary tumors correlates significantly with metastasis as its observed in kaplan meier plot and is highlighted by the HR and the p-value obtained.

Figure 2:
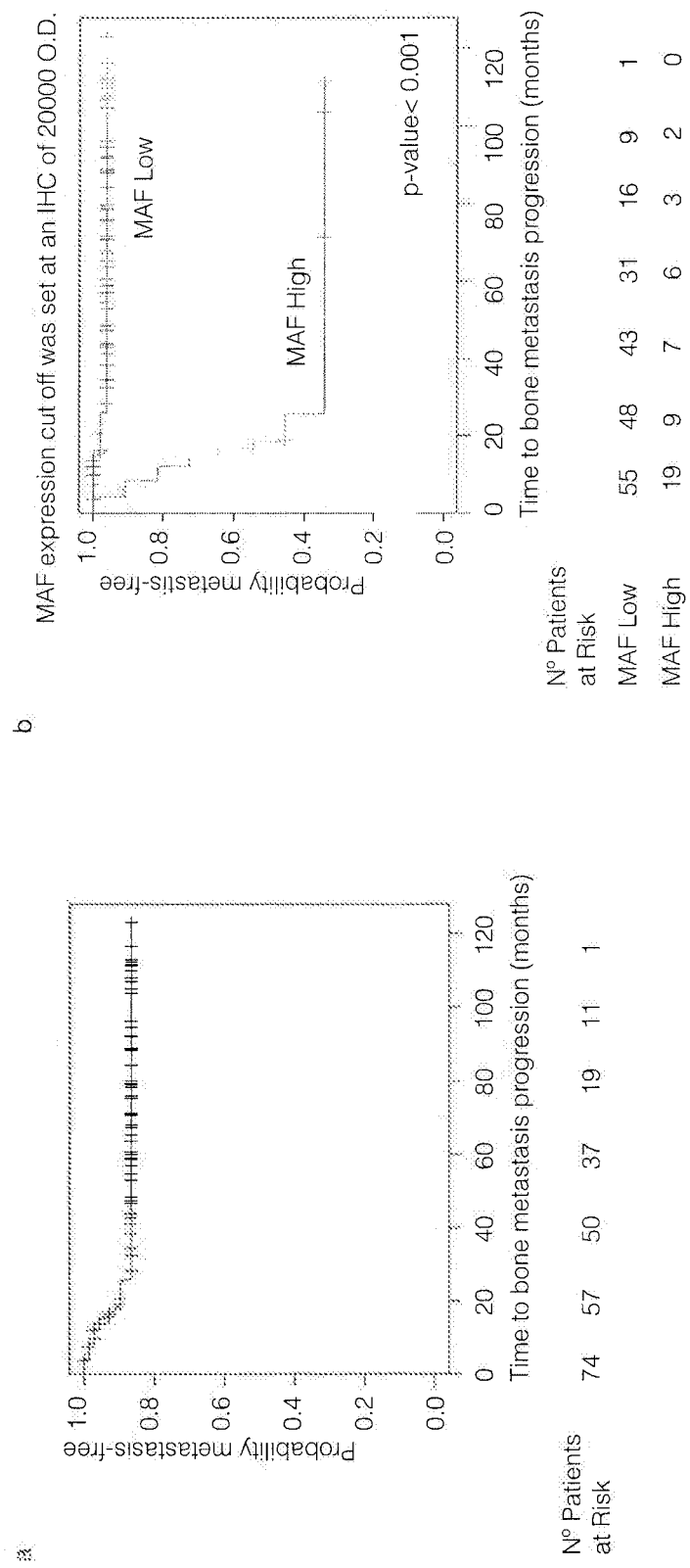

FIG. 2: a) Kaplan-Meier plot depicting the probability of bone metastasis free survival at any time in the overall population of lung cancer patients post primary tumor resection. b) Kaplan-Meier plot depicting the probability of bone metastasis free survival at any time in lung cancer primary tumor biopsies according to c-MAF high or low protein expression categories measured by immunohistochemistry (IHC). The c-MAF expression cut of (20,000 Optical Density, O.D., Units) was selected based on a receiving operating curve (ROC curve) as per standard methods (Area under the curve, AUC, is 0.80).

Figure 3:
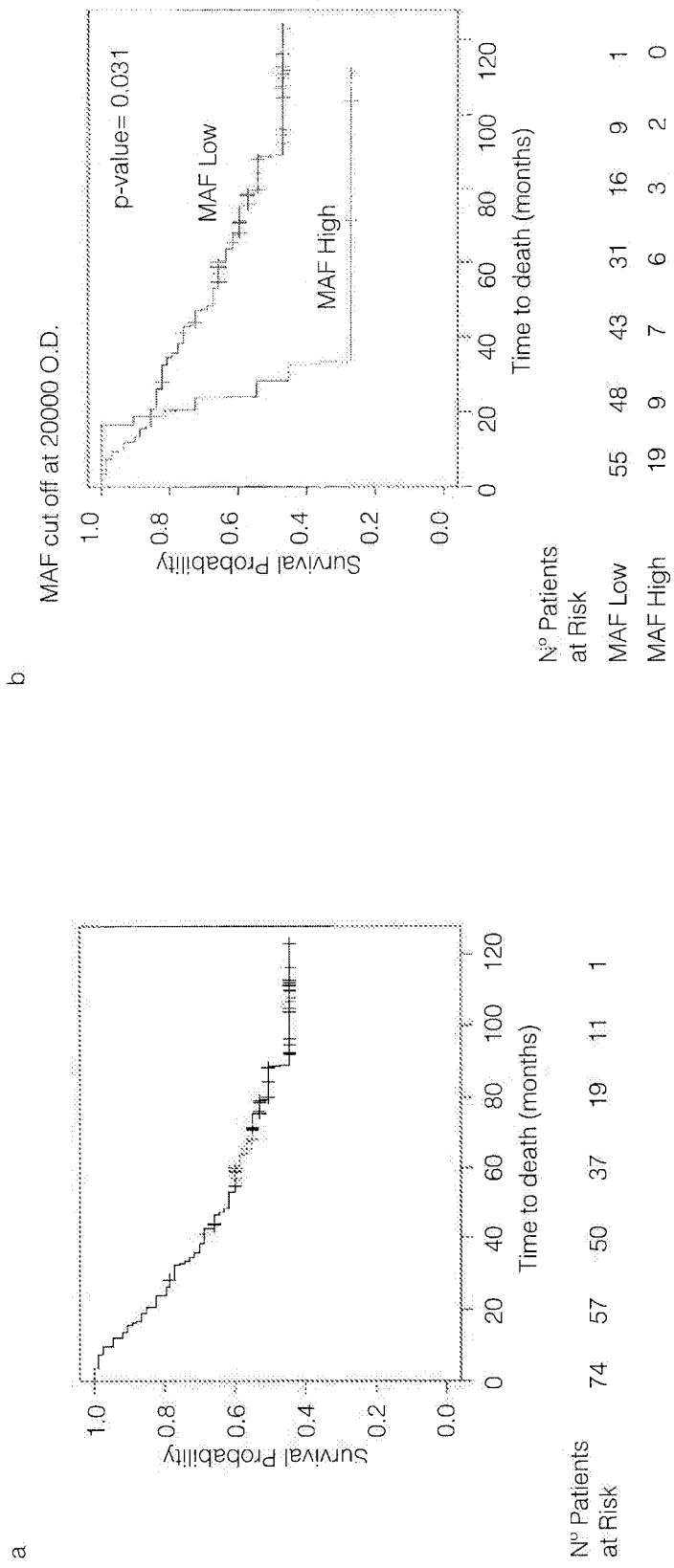

FIG. 3: a) Kaplan-Meier plot depicting the probability of survival in the overall population of lung cancer patients from the time of primary tumor resection. b) Kaplan-Meier plot depicting the probability of survival in lung cancer primary according to c-MAF high or low protein expression categories. The c-MAF expression cut of (20,000 Optical Density, O.D., Units) was selected based on a receiving operating curve (ROC curve) based on bone metastasis at any time as per standard methods.

DETAILED DESCRIPTION OF THE INVENTION

Methods for the Diagnosis and Prognosis of Lung Cancer Metastasis Based on c-MAF Expression Levels The inventors have identified that the c-MAF gene and protein is overexpressed in lung cancer metastasis, and that the c-MAF expression levels in primary lung tumors are correlated to different clinical parameters of lung cancer, particularly with recurrence and metastasis probability. Thus, c-MAF overexpression is correlated with the onset of lung tumor metastasis in bone. Therefore, c-MAB can be used as a marker, for the diagnosis and/or prognosis of metastasis, in particular bone metastasis, in a subject with lung cancer.

Thus in one aspect, the invention relates to an in vitro method for the diagnosis of metastasis in a subject with lung dancer and/or for the prognosis of the tendency to develop metastasis in a subject with lung cancer (hereinafter first method of the invention) which comprises
    (i) quantifying the c-MAF gene expression level in a tumor sample (e.g., lung tumor tissue, circulating lung tumor cell, circulating lung tumor DNA) from said subject and
    (ii) comparing the expression level previously obtained with the expression level of said gene in a control sample,
wherein if the expression levels of said gene are increased with respect to the expression levels of said gene in the control sample, then said subject has a positive diagnosis for metastasis or a greater tendency to develop metastasis, in a preferred site bone metastasis.

The c-MAF gene (v-maf musculoaponeurotic fibrosarcoma oncogene homologue (avian) also known as MAF or MGC71685) is a transcription factor containing a leucine zipper which acts like a homodimer or a heterodimer. Depending on the DNA binding site, the encoded protein can be a transcriptional activator or repressor. The DNA sequence encoding c-MAF is described in the NCBI database under accession number NG_016440 (SEQ ID NO: 1). The coding sequence of c-MAF is set forth in SEQ ID NO: 13. Two messenger RNA are transcribed from said DNA sequence, each of the which will give rise to one of the two c-MAF protein isoforms, the α isoform and the β isoform. The complementary DNA sequences for each of said isoforms are described, respectively, in the NCBI database under accession numbers NM_005360.4 (SEQ ID NO: 2) and NM_001031804.2 (SEQ ID NO: 3).

In the context of the present invention, "metastasis" is understood as the propagation of a cancer from the organ where it started to a different organ. It generally occurs through the blood or lymphatic system. When the cancer cells spread and form a new tumor, the latter is called a secondary or metastatic tumor. The cancer cells forming the secondary tumor are like those of the original tumor. If a lung, cancer, for example, spreads (metastasizes) to the bone, the secondary tumor is formed of malignant lung cancer cells. The disease in the bone is metastatic lung cancer and not bone cancer. In a particular embodiment of the method of the invention, the metastasis is lung cancer which has spread (metastasized) to the bone.

In the present invention, "diagnosis of metastasis in a subject with lung cancer" is understood as identifying a disease (metastasis) by means of studying its signs, i.e., in the context of the present invention by means of increased c-MAF gene expression levels (i.e., overexpression) in the lung cancer tumor-tissue with respect to a control sample.

In the present invention "prognosis of the tendency to develop metastasis in a subject with lung cancer" is understood as knowing based on the signs if the lung cancer that said subject has will metastasize in the future. In the context of the present invention, the sign is c-MAF gene overexpression in tumor tissue.

The method of the invention comprises in a first step quantifying the c-MAF gene expression level in a tumor tissue sample from a subject.

In a preferred embodiment, the first method of the invention comprises quantifying only the c-MAF gene expression level as a single marker, i.e., the method does not involve determining the expression level of any additional marker.

As used herein, the term "subject" or "patient" refers to all animals classified as mammals and includes but is not limited to domestic and farm animals, primates and humans, for example, human beings, non-human primates, cows, horses, pigs, sheep, goats, dogs, cats, or rodents. Preferably, the subject is a human man or woman of any age or race.

The terms "poor" or "good", as used herein to refer to a clinical outcome, mean that the subject will show a favourable or unfavourable outcome. As will be understood by those skilled in the art, such an assessment of the probability, although preferred to be, may not be correct for 100% of the subjects to be diagnosed. The term, however, requires that a statistically significant portion of subjects can be identified as having a predisposition for a given outcome. Whether a portion is statistically significant can be determined readily by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least about 50%, at least about 60%, at least about 70%, at least about 80%, at least about 90% at least about 95%. The p-values are, preferably, 0.05, 0.01, 0.005, or 0.0001 or less. More preferably, at least about 60 percent, at least about 70 percent, at least about 80 percent or at least about 90 percent of the subjects of a population can be properly identified by the method of the present invention.

In the present invention "tumor sample" is understood as the sample (e.g., tumor tissue, circulating tumor cell, circulating tumor DNA) originating from the primary lung cancer tumor. Said sample can be obtained by conventional methods, for example biopsy, using methods well known by the persons skilled in related medical techniques. The methods for obtaining a biopsy sample include splitting a tumor into large pieces, or microdissection, or other cell separating methods known in the art. The tumor cells can additionally be obtained by means of cytology through aspiration with a small gauge needle. To simplify sample preservation and handling, samples can be fixed in formalin and soaked in paraffin or first frozen and then soaked in a tissue freezing medium such as OCT compound by means of immersion in a highly cryogenic medium which allows rapid freezing.

As understood by the person skilled in the art, the gene expression revels can be quantified by measuring the messenger RNA levels of said gene or of the protein encoded by said gene.

For this purpose, the biological sample can be treated to physically or mechanically break up the tissue or cell structure, releasing the intracellular, components into an aqueous or organic solution for preparing nucleic acids. The nucleic acids are extracted by means of commercially available methods known by the person skilled in the art (Sambroock, J., et al., "Molecular cloning: a Laboratory Manual", 3rd ed., Cold Spring Harbor Laboratory Press, N.Y., Vol. 1-3)

Thus, the c-MAF gene expression level can be quantified from the RNA resulting from the transcription of said gene (messenger RNA or mRNA) or, alternatively, from the complementary DNA (cDNA) of said gene. Therefore, in a particular embodiment of the invention, the quantification of the c-MAF gene expression levels comprises the quantification of the messenger RNA of the c-MAF gene or a fragment of said mRNA, complementary DNA of the c-MAF gene or a fragment of said cDNA or the mixtures thereof.

Virtually any conventional method can be used within the scope of the invention for detecting and quantifying the mRNA levels encoded by the c-MAF gene or of the corresponding cDNA thereof. By way of non-limiting illustration, the mRNA levels encoded by said gene can be quantified using conventional methods, for example, methods comprising mRNA amplification and the quantification of said mRNA amplification product, such as electrophoresis and staining, or alternatively, by Southern blot and using suitable probes, Northern blot and using specific probes of the mRNA of the gene of interest (c-MAF) or of the corresponding cDNA thereof, mapping with S1 nuclease, RT-PCR, hybridization, micro arrays, etc., preferably by means of real time quantitative PCR using a suitable marker. Likewise, the cDNA levels corresponding to said mRNA encoded by the c-MAF gene can also be quantified by means of using conventional techniques; in this case, the method of the invention includes a step for synthesizing the corresponding cDNA by means of reverse transcription (RT) of the corresponding mRNA followed by the amplification and quantification of said cDNA amplification product. Conventional methods for quantifying expression levels can be found, for example, in Sambrook et al., 2001. (cited ad supra).

In a particular embodiment, the c-MAF gene expression levels are quantified by means of quantitative polymerase chain reaction (PCR) or a DNA or RNA array.

In addition, the c-MAF gene expression level can also be quantified by means of quantifying the expression levels of the protein encoded by said gene, i.e., the c-MAF protein (c-MAF) [NCBI, accession number O75444], or any functionally equivalent variant of the c-MAF protein. There are two c-MAF protein isoforms, the α isoform (NCBI, NP_005351.2) made up of 403 amino acids (SEQ ID NO: 4) and the β isoform (NP_001026974.1) made up of 373 amino acids (SEQ ID NO: 5). The c-MAF gene expression level can be quantified by means of quantifying the expression levels of any of the c-MAF protein isoforms. Thus, in a particular embodiment, the quantification of the levels of the protein encoded by the c-MAF gene comprises the quantification of the c-MAF protein.

In the context of the present invention, "functionally equivalent variant of the c-MAF protein" is understood as (i) variants of the c-MAF protein (SEQ ID NO: 4 or SEQ ID NO: 5) in which one or more of the amino acid residues are substituted by a conserved or non-conserved amino acid residue (preferably a conserved amino acid residue), wherein such substituted amino acid residue may or may not be one encoded by the genetic code, or (ii) variants comprising an insertion or a deletion of one or more amino acids and having the same function as the c-MAF protein, i.e., to act as a DNA binding transcription factor. Variants of the c-MAF protein can be identified using methods based on the capacity of c-MAF for promoting in vitro cell proliferation as shown in international-patent application WO2605/046731 (hereby incorporated by reference in its entirety), based on the capacity of the so-called inhibitor for blocking the transcription capacity of a reporter gene under the control of cyclin D2 promoter or of a promoter containing the c-MAF responsive region (MARE or c-MAF responsive element) in cells expressing c-MAF as described in WO2008098351 (hereby incorporated by reference in its entirety), or based on the capacity of the so-called inhibitor for blocking reporter gene expression under the control of the IL-4 promoter in response to the stimulation with PMA/ionomycin in cells expressing NFATc2 and c-MAF as described in US2009048117A (hereby incorporated by referenced its entirety).

The variants according to the invention preferably have sequences similarity with the amino acid sequence of any of the c-MAF protein isoforms (SEQ ID NO: 4 or SEQ ID NO: 5) of at least 50%, at least 60%, at least 70%, at least 80%, at least 90%, at least 91%, at least 92%, at least 93%, at least 94%, at least 95%, at least 96%, at least 97%, at least 98% or at least 99%. The degree of similarity between the variants and the specific c-MAF protein sequences defined previously is determined using algorithms and computer processes which are widely known by the persons skilled in the art. The similarity between two amino acid sequences is preferably determined using the BLASTP algorithm [BLAST Manual, Altschul, S., et al., NCBI NLM NIH Bethesda, Md. 20894, Altschul, S., et al., J. Mol. Biol. 215: 403-410 (1990)].

The c-MAF protein expression level can be quantified by any conventional method which allows detecting and quantifying said protein in a sample from a subject. By way of non-limiting illustration, said protein levels can be quantified, for example, by using antibodies with c-MAF binding capacity (or a fragment thereof containing an antigenic determinant) and the subsequent quantification of the complexes formed. The antibodies used in these assays may or may not be labeled. Illustrative examples of markers that can be used include radioactive isotopes, enzymes, fluorophores, chemiluminescence reagents, enzyme substrates or cofactors, enzyme inhibitors; particles, dyes, etc. There is a wide range of known assays that can be used in the present invention which use unlabeled antibodies (primary antibody) and labeled antibodies (secondary antibody); these techniques include Western-blot or Western transfer, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of protein microarrays or biochips including specific antibodies, or assays based on colloidal precipitation in formats such as dipsticks. Other ways for detecting and quantifying said c-MAF protein include affinity chromatography techniques, ligand binding assays, etc. When an immunological method is used, any antibody or reagent that is known to bind to the c-MAF protein with a high affinity can be used for detecting the amount thereof. Nevertheless, the use of an antibody, for example, polyclonal sera, supernatants of hybridomas or monoclonal antibodies, antibody fragments, Fv, Fab, Fab' and F(ab')2, scFv, humanized diabodies, triabodies, tetrabodies, nanobodies, alphabodies, stapled peptides, cyclopeptides and antibodies. There are commercial anti-c-MAF protein antibodies on the market which can be used in the context of the present invention, such as for example antibodies ab427, ab55502, ab55502, ab72584, ab76817, ab77071 (Abcam plc, 330 Science Park, Cambridge CB4 0FL, United Kingdom), the O75444 monoclonal antibody (Mouse Anti-Human MAF Azide free Monoclonal antibody, Unconjugated, Clone 6b8) of AbD Serotec, etc. There are many commercial companies offering anti-c-MAF antibodies, such as Abnoya Corporation, Bethyl Laboratories, Santa Cruz Biotechnology, Bioworld Technology, GeneTex, etc.

In a particular embodiment, the c-MAF protein levels are quantified means of western blot, immunohistochemistry, ELISA of a protein array.

In another particular, embodiment, the c-MAF protein levels are quantified from exosomes or circulating DNA. Exosomes are 40-100 nm membrane vesicles secreted by most cell types in vivo and in vitro. Exosomes form in a particular population of endosomes, called multivesicular bodies (MVBs) by inward budding into the lumen of the compartment. Upon fusion of MVBs with the plasma membrane, these internal vesicles are secreted. Exosomes can be isolated from diverse cell lines or body fluids by several methods well known in the art (Théry C. et al., *Curr Protoc Cell Biol.* 2006 April; Chapter 3 Unit 3.22) (the entire contents of which are incorporated by reference herein). Several commercial kits are available for the isolation of exosomes such as ExoQuick™ or ExoTest™.

The first method of the invention comprises in a second step comparing the c-MAF gene expression level obtained in the tumor sample (including but not limited to a primary tumor biopsy, circulating tumor cells and circulating tumor DNA) from the subject with the expression level of said gene in a control sample.

Once the c-MAF gene expression level in a tumor tissue sample, a circulating tumor cell or circulating tumor DNA from a subject with lung cancer has been measured and compared with the control sample, if the expression level of said gene are increased with respect to its expression level in the control sample, then it can be concluded that said subject has a positive diagnosis for metastasis or a greater tendency to develop metastasis.

The determination of the c-MAF gene expression level must be correlated with values of a control sample or reference sample. Depending on the type of tumor to be analyzed, the exact nature of the control sample may vary. Thus, in the event that a diagnosis is to be evaluated, then the reference sample is a tumor tissue sample from a subject with lung cancer that has not metastasized or that corresponds to the median value of the c-MAF gene expression levels measured in a tumor tissue collection in biopsy samples from subjects with lung cancer which have not metastasized.

Said reference sample is typically obtained by combining equal amounts of samples from a subject population. Generally, the typical reference samples will be obtained from subjects who are clinically well documented and in whom the absence of metastasis is well characterized. In such samples, the normal concentrations (reference concentration) of the biomarker (c-MAF gene) can be determined, for example by providing the mean concentration over the reference population. Various considerations are taken into account when determining the reference concentration of the marker. Among such considerations are the age, weight, sex, general physical condition of the patient and the like. For example, equal amounts of a group of at least 2, at least 10, at least 100 to preferably more than 1000 subjects, preferably classified according to the foregoing considerations, for example according to various age categories, are taken as the reference group. The sample collection from which the reference level is derived will preferably be formed by subjects suffering from the same type of cancer as the patient object of the study (e.g., lung cancer). Similarly, the reference value within a cohort of patients can be established using a receiving operating curve (ROC) and measuring the area under the curve for all sensitivity and specificity pairs to determine which pair provides the best values and to which reference value corresponds.

Once this median or reference value has been established, the level of this marker expressed in tumor tissues from patients with this median value can be compared and thus be assigned to the "increased" expression level. Due to the variability among subjects (for example, aspects referring to age, race, etc.) it is very difficult (if not virtually impossible) to established absolute reference, values of c-MAF expression. Thus, in particular embodiments the reference values for "increased" or "reduced" expression of the c-MAF expression are determined by calculating the percentiles by conventional means which involves performing assays in one or several samples isolated from subjects whose disease is well documented by any of the methods mentioned above the c-MAF expression levels. The "reduced" levels of c-MAF can then preferably be assigned to samples wherein the c-MAF expression levels are equal to or lower than $50^{th}$ percentile in the normal population including, for example, expression levels equal to or lower than the $60^{th}$ percentile in the normal population, equal to or lower than the $70^{th}$ percentile in the normal population, equal to or lower than the $80^{th}$ percentile in the normal population, equal to or lower than the $90^{th}$ percentile in the normal population, and equal to or lower than the $95^{th}$ percentile in the normal population. The "increased" c-MAF gene expression levels can then preferably be assigned to samples wherein the c-MAF gene expression levels are equal to or greater than the $50^{th}$ percentile in the normal population including, for example, expression levels equal to or greater than the $60^{th}$ percentile in the normal population, equal to or greater than the $70^{th}$ percentile in the normal population, equal to or greater than the $80^{th}$ percentile in the normal population, equal to or greater than the $90^{th}$ percentile in the normal population, and equal to or greater than the $95^{th}$ percentile in the normal population.

In the present invention "increased expression levels" is understood as the expression level when it refers to the levels of the c-MAF gene greater than those in a reference sample or control sample. Particularly, a sample can be considered to have high c-MAF expression levels when the expression levels in the reference sample are at least 1.1 times, 1.5 times, 5 times, 10 times, 20 times, 30 times, 40 times, 50 times, 60 times, 70 times, 80 times, 90 times, 100 times or even more with respect to the sample isolated from the patient.

In the context of the present invention, it is understood that "a subject has a positive diagnosis for metastasis" when the lung cancer suffered by said subject has metastasized to other organs of the body, in a particular embodiment, to the bone.

In a yet more preferred embodiment, the metastasis to bone is an osteolytic bone metastasis. As used herein, the expression "osteolytic bone metastasis" refers to a type of metastasis in which bone resorption (progressive loss of the bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

On the other hand, it is understood in the present invention that "a subject has a greater tendency to develop metastasis" when the probabilities that the lung cancer suffered by the subject will metastasize in the future are high.

The person skilled in the art will understand that the prediction of the tendency for a primary lung tumor to metastasize is not intended to be correct for all the subjects to be identified (i.e., for 100% of the subjects). Nevertheless, the term requires enabling the identification of a statistically significant part of the subjects (for example, a cohort in a cohort study). Whether a part is statistically significant can be determined in a simple manner by the person skilled in the art using various well known statistical evaluation tools, for example, the determination of confidence intervals, determination of p values, Student's T test Mann-Whitney test, etc. Details are provided in Dowdy and Wearden, Statistics for Research, John Wiley and Sons, New York 1983. The preferred confidence intervals are at least 90%, at least 95%, at least 97%, at least 98% or at least 99%. The p values are preferably 0.1, 0.05, 0.01, 0.005 or 0.0001. More preferably, at least 60%, at least 70%, at least 80% or at least 90% of the subjects of a population can be suitably identified by the method of the present invention.

As used herein, "agent for avoiding or preventing bone degradation" refers to any molecule capable of preventing, inhibiting, treating, reducing, or stopping bone degradation either by stimulating the osteoblast proliferation or inhibiting the osteoclast proliferation or fixing the bone structure.

As used herein, a "c-MAF inhibitory agent" refers to any molecule capable of completely or partially inhibiting the c-MAF gene expression, both by preventing the expression product of said gene from being produced (interrupting the c-MAF gene transcription and/or blocking the translation of the mRNA coming from the c-MAF gene expression) and by directly inhibiting the c-MAF protein activity, c-MAF gene expression inhibitors can be identified using methods based on the capacity, of the so-called inhibitor to block the capacity of c-MAF to promote the in vitro cell proliferation, such as shown in the international patent application WO2005/046731 (the entire contents of which are hereby incorporated by reference), based on the capacity of the so-called inhibitor to block the transcription capacity of a reporter gene under the control of thecyclin D2 promoter or of a prompter containing the c-MAF response region (MARE or c-MAF responsive element) in cells which express c-MAF such as described in WO2008098351 (the entire contents of which are hereby incorporated by reference) or based on the capacity of the so-called inhibitor to block the expression of a reporter gene under the control of the IL-4 promoter in response to the stimulation with PMA/ionomycin in cells which express NFATc2 and c-MAF such as described in US2009048117A (the entire contents of which is hereby incorporated by reference).

As used herein, Mammalian target of rapamycin (mTOR) or "mTor" refers to those proteins that correspond to EC 2.7.11.1 mTor enzymes are serine/threonine protein kinases and regulate cell proliferation, cell motility, cell growth, cell survival, and transcription.

As used herein, an "mTor inhibitor" refers to any molecule capable of completely or partially inhibiting the mTor gene expression, both by preventing the expression product of said gene from being produced (interrupting the mTor gene transcription and/or blocking the translation of the mRNA coming from the mTor gene expression) and by directly inhibiting the mTor protein activity. mTor inhibitors, include inhibitors that have one or more targets in addition to inhibition of mTor activity.

As used herein, "Src" refers to those proteins that correspond to EC 2.7.10.2. Src is a non-receptor tyrosine kinase and a proto-oncogene. Src may play a role in cell growth and embryonic development.

As used herein, a "Src inhibitor" refers to any molecule capable of completely or partially inhibiting the Src gene expression, both by preventing the expression product of said gene from being produced (interrupting the Src gene transcription and/or blocking the translation the mRNA coming from the Src gene expression) and by directly inhibiting the Src protein activity.

As used herein, "Prostaglandin-endoperoxide synthase 2"; "cyclooxygenase-2" or "COX-2" refers to those proteins that correspond to EC 1.14.99.1. COX-2 is responsible for converting arachidonic acid to prostaglandin endoperoxide H2.

As used herein, a "COX-2 inhibitor" refers to any molecule capable of completely or partially inhibiting the COX-2 gene expression, both by preventing the expression product of said gene from being produced (interrupting the COX-2 gene transcription and/or blocking the translation of the mRNA coming from the COX-2 gene expression) and by directly inhibiting the COX-2 protein activity.

As used herein "outcome" or "clinical outcome" refers to the resulting course of disease and/or disease progression and can be characterized for example by recurrence, period of time until recurrence, metastasis, period of time until metastasis, number of metastases, number of sites of metastasis and/or death due to disease. For example a good clinical outcome includes cure, prevention of recurrence, prevention of metastasis and/or survival within a fixed period of time (without recurrence), and a poor clinical outcome includes disease progression, metastasis and/or death within a fixed period of time.

"Predicting", as used herein, refers to the determination of the likelihood that the subject suffering lung cancer will develop metastasis to a distant organ. As used herein, "good prognosis" indicates that the subject is expected (e.g. predicted) to survive and/or have no, or is at low risk of having, recurrence or distant metastases within a set time period. The term "low" is a relative term and, in the context of this application, refers to the risk of the "low" expression group with respect to a clinical outcome (recurrence, distant metastases, etc.). A "low" risk can be considered as a risk lower than the average risk for an heterogeneous cancer patient population. In the study of Paik et al. (2004), an overall "low" risk of recurrence was considered to be lower than 15 percent. The risk will also vary in function of the time period. The time period can be, for example, five years, ten years, fifteen years or even twenty years after initial diagnosis of cancer or after the prognosis was made.

As used herein, "poor prognosis" indicates that the subject is expected e.g. predicted to not survive and/or to have, or is at high risk of having, recurrence or distant metastases within a set time period. The term "high" is a relative term and, in the context of this application, refers to the risk of the "high" expression group With respect to a clinical outcome (recurrence, distant metastases, etc.). A "high" risk can be considered as a risk higher than the average risk for a heterogeneous cancer patient population. In the study of Paik et al. (2004), an overall "high" risk of recurrence was considered to be higher than 15 percent. The risk will also vary in function of the time period. The time period can be, for example, five years, ten years, fifteen years or even twenty years of initial diagnosis of cancer or after the prognosis was made.

"Reference value", as used herein, refers to a laboratory value used as a reference for values/data obtained by laboratory examinations of patients or samples collected from patients. The reference value or reference level can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from a population of subjects of the chronological age matched group, or based on a pool of samples including or excluding the sample to be tested.

The term "treatment", as used herein, refers to any type of therapy, which aims at terminating, preventing, ameliorating or reducing the susceptibility to a clinical condition as described herein. In a preferred embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder, or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad senseto refer to at least a reduction in the magnitude of a parameter, such as inflammation, pain, or immune deficiency.

As used herein, "sample" or "biological sample" means biological material isolated from a subject. The biological sample may contain any biological material suitable for determining the expression level of the c-MAF gene. The sample can be isolated from any suitable biological tissue or fluid such as, for example, tumor tissue, blood, blood plasma, serum, urine or cerebral spinal fluid (CSF).

As used herein, the term "expression level" of a gene as used herein refers to the measurable quantity of gene product produced by the gene in a sample of the subject, wherein the gene product can be a transcriptional product or a translational product. Accordingly, the expression level can pertain to a nucleic acid gene product such as mRNA or cDNA or a polypeptide gene product. The expression level is derived from a subject's sample and/or a reference sample or samples, and can for example be detected de novo or correspond to a previous determination. The expression level can be determined or measured, for example, using microarray methods, PCR methods (such as qPCR), and/or antibody based methods, as is known to a person of skill in the art.

As used herein, the term "gene copy number" refers to the copy number of a nucleic acid molecule in a cell. The gene copy number includes the gene copy number in the genomic (chromosomal) DNA of a cell. In a normal cell (non-tumoral cell), the gene copy number is normally two copies (one copy in each member of the chromosome pair). The gene copy number sometimes includes half of the gene copy number taken from samples of a cell population.

"Increased expression level" is understood as the expression level when it refers to the levels of the c-MAF gene greater than those in a reference sample or control sample. This increased levels can be caused without excluding other mechanisms by a gene or 16q23 or 16q22-24 chromosomal locus amplification or translocation. Particularly, a sample can be considered to have high c-MAF expression level when the expression level in the sample isolated from the patient is at least about 1.1 times, 1.2 times, 1.3 times, 1.4 times, 1.5 times, 2 times, 3 times, 4 times, 5 times, 10 times, 20 times, 30 times, 40 times, 50 times, 60 times, 70 times, 80 times, 90 times, 100 times or even more with respect to the reference or control.

"Probe", as used herein, refers to an oligonucleotide sequence that is complementary to a specific nucleic acid sequence of interest. In some embodiments, the probes may be specific to regions of chromosomes which are known to undergo translocations. In some embodiments, the probes have a specific label or tag. In some embodiments, the tag is a fluorophore. In some embodiments, the probe is a DNA in situ hybridization probe whose labeling is based on the stable coordinative binding of platinum to nucleic acids and proteins. In some embodiments, the probe is described in U.S. patent application Ser. No. 12/067,532 and U.S. patent application Ser. No. 12/181,399, which are incorporated herein by reference in their entirety, or as described in Swennenhuis et al. "Construction of repeat-free fluorescence in situ hybridization probes" Nucleic Acids Research 40(3): e20 (2012).

"Tag" or "label", as used herein, refers to any physical molecule which is directly or indirectly associated with a probe, allowing the probe or the location of the probed to be visualized, marked, or otherwise captured.

"Translocation", as used herein, refers to the exchange of chromosomal material in unequal or equal amounts between chromosomes. In some cases, the translocation is on the same chromosome. In some cases, the translocation is between different chromosomes. Translocations occur at a high frequency in many types, of cancer, including breast cancer and leukemia. Translocations can be either primary reciprocal translocations or the more complex secondary translocations. There are several primary translocations that involve the immunoglobin heavy chain (IgH) locus that are believed to constitute the initiating event in many cancers.

(Eychène, A., Rocques, N., and Puoponnot, C., A new MAFia in cancer. 2008. Nature Reviews: Cancer. 8:683-693.)

"Polyploid" or "polyploidy", as used herein, indicates that the cell contains more than two copies of a gene, of interest. In some instances, the gene of interest is MAF. In some embodiments, polyploidy is associated with an accumulation of expression of the gene of interest. In some embodiments, polyploidy is 32 associated with genomic instability. In some embodiments, the genomic instability may lead to chromosome translocations.

"Whole genome sequencing", as used herein, is a process by which the entire genome of an organism is sequenced at a single time. See, e.g., Ng., P. C. and Kirkness, E. F., Whole Genome Sequencing. 2010. Methods in Molecular Biology. 628:215-226.

"Exome sequencing", as used herein, is a process by which the entire coding region of the DNA of an organism is sequenced. In exome sequencing, the mRNA is sequenced. The untranslated regions of the genome are not included in exome sequencing. See, e.g., Choi, M. et al., Genetic diagnosis by whole exome capture and massively parallel DNA sequencing. 2009. PNAS. 106(45): 19096-19101.

"Tumor tissue sample" is understood as the tissue sample originating from the lung cancer tumor, including but hot limited to circulating tumor cells and circulating tumor DNA. Said sample can be obtained by conventional methods, for example biopsy, using methods well known by the persons skilled in related medical techniques.

"Osteolytic bone, metastasis" refers to a type of metastasis in which bone resorption (progressive loss of the bone density) is produced in the proximity of the metastasis resulting from the stimulation of the osteoclast activity by the tumor cells and is characterized by severe pain, pathological fractures, hypercalcemia, spinal cord compression and other syndromes resulting from nerve compression.

Method for Designing Customized Therapy of the Invention in Patients with Lung Tumors As is known in the state of the art, the treatment to be administered to a subject suffering from cancer depends on whether the latter is a malignant tumor, i.e., whether it has high probabilities of undergoing metastasis, or whether the latter is a benign tumor. In the first assumption, the treatment of choice is a systemic treatment such as chemotherapy and in the second assumption, the treatment of choice is a localized treatment such as radiotherapy.

Therefore, as described in the present invention, given that the c-MAF gene overexpression in lung cancer cells is related to the presence of metastasis, the c-MAF gene expression levels allow making decisions in terms of the most suitable therapy for the subject suffering said cancer.

Thus, in another aspect the invention relates to an in vitro method for designing a customized therapy for a subject with lung cancer, which comprises
  (i) quantifying the c-MAF gene expression level in a tumor sample of said subject and
  (ii) comparing the expression level previously obtained with the expression level of said gene in a control sample,
wherein if the expression levels are increased with respect to the expression levels of said gene in the control sample, then said subject is susceptible to receive a therapy aiming to prevent and/or treat the metastasis. In a particular aspect of the invention, the subject is then administered at least one therapy that prevents, inhibits and/or treats the bone metastasis.

wherein if the c-MAF gene expression level is not increased with respect to said reference value, then said subject is not susceptible to receive a therapy for preventing the bone degradation. In a particular aspect of this method, the subject is then not administered at least one therapy that prevents, inhibits and/or treats the bone metastasis.

In a particular embodiment, the metastasis is a bone metastasis. In a more preferred embodiment, the bone metastasis is osteolytic metastasis.

The terms and expressions "subject", "lung cancer", "tumor sample", "metastasis", "determination of expression levels", "c-MAF gene", "increased expression levels" and "control sample" have been described in detail in relation to the first method of the invention and are equally applicable to the second and third method of the invention.

The second method of the invention comprises in a first step quantifying the c-MAF gene expression level in a tumor sample in a subject suffering from lung cancer.

In a preferred embodiment, the second method of the invention comprises quantifying only the c-MAF gene expression level as a single marker, i.e., the method does not involve determining the expression level of any additional marker.

In the case of the second method of the invention the sample is a primary tumor tissue sample of the subject. In a second step, the c-MAF gene expression level obtained in the tumor sample of the subject is compared with the expression level of said gene in a control sample. The determination of the c-MAF gene expression levels must be related to values of a control sample or reference sample. Depending on the type of tumor to be analyzed, the exact nature of the control sample may vary. Thus preferably the reference sample is a tumor tissue sample of subject with lung cancer that has not metastasized or that correspond to the median value of the c-MAF gene expression levels measured in a tumor tissue collection in biopsy samples of subjects with lung cancer which has not metastasized.

In yet another embodiment, an expression level of c-MAF which is above the average indicates increased risk of bone metastasis, the risk being proportional to the levels of c-MAF expression. Thus, the risk of bone metastasis in a subject suffering lung cancer is dose-dependent.

Once the c-MAF gene expression levels in the sample have been measured and compared with the control sample, levels of said gene are increased with respect to their expression levels in the control sample, then it can be concluded that said subject is susceptible to receiving therapy aiming to prevent (if the subject has yet to undergo metastasis) and/or treat metastasis (if the subject has already experienced metastasis). If such increased expression is not observed then the subject is not administered at least one therapy that prevents, inhibits and/or treats the bone metastasis.

When the cancer has metastasized, systemic treatments including but not limited to chemotherapy, hormone treatment, immunotherapy, or a combination thereof are used. Additionally, radiotherapy and/or surgery can be used. The choice of treatment generally depends on the type of primary cancer, the size, the location of the metastasis, the age, the general health of the patient and the types of treatments used previously.

The systemic treatments are those that reach the entire body:
  Chemotherapy is the use of medicaments to destroy cancer cells. The medicaments are generally administered through oral or intravenous route. Sometimes, chemotherapy is used together with radiation treatment.

Suitable chemotherapeutic treatments for lung cancer include, without limitation, anthracyclines (doxorubicin, epirubicin, pegylated liposomal doxorubicin), Taxanes (paclitaxel, docetaxel, albumin nano-particle bound paclitaxel), 5-fluorpuracil (continuous infusion 5-FU, capecitabine), Vinca alkaloids (vinorelbine, vinblastine), Gemcitabine, Platinum salts (cisplatin, carboplatin), cyclophosphamide, Etoposide and combinations of one or more of the above such as Cyclophosphamide/anthracycline+/−5-fluorouracil regimens (such as doxorubicin/cyclophosphamide (AC), epirubicin/cyclophosphamide, (EC) cyclophosphamide/epirubicin/5-fluorouracil (CEF), cyclophosphamide/doxorubicin/5-fluorouracil (CAF), 5-fluorouracil/epirubicin/cyclophosphamide (FEC)), cyclophosphamide/metothrexate/5-fluorouracil (CMF), anthracyclines/taxanes (such as doxorubicin/paclitaxel or doxorubicin/docetaxel), Docetaxel/capecitabine, Gemcitabine/paclitaxel, Taxane/platinum regimens (such as paclitaxel/carboplatin or docetaxel/carboplatin).

Hormone therapy is based on the fact that some hormones promote cancer growth. For example, estrogen in women produced by the ovaries sometimes promotes the breast cancer growth. There are several ways for stopping the production of these hormones. A way is to remove the organs producing them: the ovaries in the case of women, the testicles in the case of the men. More frequently, medicaments to prevent these organs from producing the hormones or to prevent the hormones from acting on the cancer cells can be used.

Immunotherapy is a treatment that aids the immune system itself of the patient to combat cancer. There are several types of immunotherapy which are used to treat metastasis patients. These include but are not limited to cytokines, monoclonal antibodies and antitumor vaccines.

In another aspect, the treatment is Alpharadin (radium-223 dichloride). Alpharadin uses alpha radiation from radium-223 decay to kill cancer cells. Radium-223 naturally self-targets to bone metastases by virtue of its properties as a calcium-mimic. Alpha radiation has a very short range of 2-10 cells (when compared to current radiation therapy which is based on beta or gamma radiation), and therefore, causes less damage to surrounding healthy tissues (particularly bone marrow). With similar properties to calcium, radium-223 is drawn to places where calcium is used to build bone in the body, including the site of faster, abnormal bone growth—such as that seen in the skeletal metastases of men with advanced, castration-resistant prostate cancer. Radium-223, after injection, is carried in the bloodstream to sites of abnormal bone growth. The place where a cancer starts in the body is known as the primary tumor. Some of these cells may break away and be carried in the bloodstream to another part of the body. The canter cells may then settle in that part of the body and form a new tumor. If this happens it is called a secondary cancer or a metastasis. Most patients with late stage prostate cancer suffer the maximum burden of disease in their bones. The aim with radium-223 is to selectively target this secondary cancer. Any radium-223 not taken-up in the bones is quickly routed to the gut and excreted.

In another aspect, the treatment is an mTor inhibitor. In some aspects, the mTor inhibitor is a dual mTor/PI3kinase inhibitor. In some aspects, the mTor inhibitor is used to prevent or inhibit metastasis. In some aspects the mTor inhibitor is selected from the group consisting of: ABI009 (sirolimus), rapamycin (sirolimus), Abraxane (paclitaxel), Absorb (everolimus), Afinitor (everolimus), Afinitor with Gleevec, AS703026 (pimasertib), Axxess (umirolimus), AZD2014, BEZ235, Biofreedom (umirolimus), BioMatrix (umirolimus), BioMatrix flex (umirolimus), CC115, CC223, Combo Bio-engineered Sirolimus Eluting Stent ORBUS-NEICH (sirolimus), Curaxin CBLC102 (mepacrine), DE109 (sirolimus), DS3078, Endeavor DES (zotarolimus), Endeavor Resolute (zotarolimus), Femara (letrozole), Hocena (antroquinoriol), INK128 Inspiron (sirolimus), IPI504 (retaspimycin hydrochloride), KRN951 (tivozanib), ME344, MGA031 (teplizumab), MiStent SES (sirolimus), MKC1, Nobori (umirolimus), OSI027, OVI123 (cordycepin), Palomid 529, PF04691502, Promus Element (everolimus), PWT33597, Rapamune (sirolimus), Resolute DES (zotarolimus), RG7422, SAR245409, SF1126, SGN75 (vorsetuzumab mafodotin), Synergy (everolimus), Taltorvic (ridaforolimus), Tarceva (erlotinib), Torisel (temsirolimus), Xience Prime (everolimus), Xience V (everolimus), Zomaxx (zotarolimus), Zortress (everolimus), Zotarolimus Eluting Peripheral Stent MEDTRONIC (zotarolimus), AP23841, AP24170, ARmTOR26, BN107, BN108, Canstatin GENZYME (canstatin), CU906, EC0371, EC0565, KI1004, LOR220, NV128, Rapamycin ONCOIMMUNE (sirolimus), SB2602, Sirolimus PNP SAMYANG BIOPHARMACEUTICALS (sirolimus), TOP216, VLI27, VS5584, WYE125132, XL388, Advacan (everolimus); AZD8055, Cypher Select Plus Sirolimus eluting Coronary Stent (sirolimuis), Cypher Sirolimus eluting coronary stent (sirolimus), Drug Coated Balloon (sirolimus), E-Magic Plus (sirolimus), Emtor (sirolimus), Esprit (everolimus), Evertor (everolimus), HBF0079, LCP-Siro (sirolimus), Limus CLARIS (sirolimus), mTOR Inhibitor CELLZOME, Nevo Sirolimus eluting Coronary Stent (sirolimus), nPT-mTOR, Rapacan (sirolimus), Renacept (sirolimus), ReZolve (sirolimus), Rocas (sirolimus), SF1126, Sirolim (sirolimus), Sirolimus NORTH CHINA (sirolimus), Sirolimus RANBAXY (sirolimus), Sirolimus WATSON (sirolimus) Siropan (sirolimus), Sirova (sirolimus), Supralimus (sirolimus), Supralimus-Core (sirolimus), Tacrolimus WATSON (tacrolimus), TAFA93; Temsirolimus ACCORD (temsirolimus), Temsirolimus SANDOZ (temsirolimus), TOP216, Xience Prime (everolimus), Xience V (everolimus). In a specific aspect the mTor inhibitor is Afinitor (everolimus) (http://www.afinitor.com/index.jsp?usertrack.filter_applied=true&NovaID= 40294620643 38207963; last accessed Nov. 28, 2012). In anther aspect, everolimus is combined with an aromatase inhibitor. (See. e.g., Baselga, J., el al., Everolimus in Postmenopausal Hormone-Receptor Positive Advanced Breast Cancer. 2012. *N. Engl. J. Med.* 366(6): 520-529, which is herein incorporated by reference). In another aspect, mTor inhibitors can be identified through methods known in the art. (See, e.g., Zhou, H. et al., Updates of mTor inhibitors. 2010. *Anticancer Agents Med. Chem.* 10(7): 571-81, which is herein incorporated by reference). In some aspects, the mTor inhibitor is used to treat or prevent or inhibit metastasis in a patient with advanced lung cancer. In some aspects, the mTor inhibitor is used in combination with a second treatment. In some aspects, the second treatment is any treatment described herein.

In another aspect, the treatment is a Src kinase inhibitor. In some aspects, the Src inhibitor is used to prevent or inhibit metastasis: In some aspects, the Src kinase inhibitor is selected from the group: AZD0530 (saracatinib), Bosulif (bosutinib), ENMD981693, KD020, KX01, Sprycel (dasatinib), Yervoy (ipilimumab), AP23464, AP23485, AP23588, AZD0424, c-Src Kinase Inhibitor KISSEI, CU201, KX2361, SKS927, SRN004, SUNK706, TG100435, TG100948, AP23451, Dasatinib HETERO (dasatinib), Dasatinib VALEANT (dasatinib), Fontrax (dasatinib), Src Kinase Inhibitor KINEX, VX680, (tozasertib lactate), XL228, and SUNK706. In some embodiments, the Src kinase inhibitor is dasatinib. In another aspect, Src kinase inhibitors can be identified through methods known in the art (See, e.g., Sen, B. and Johnson, F. M. Regulation of Src Family Kinases in Human Cancers. 2011. *J. Signal Transduction.* 2011: 14 pages, which is herein incorporated by reference). In some aspects, the Src kinase inhibitor is used to treat or prevent or inhibit metastasis in a patient that is positive for the SRC-responsive signature (SRS). In some aspects, the patient is SRS+ and ER−. (See. e.g., Zhang, C H-F, et al. Latent Bone Metastasis in Breast Cancer Tied to Src-Dependent survival signals. 2009. *Cancer Cell.* 16:67-78, which is herein incorporated by reference.) In some aspects, the Src kinase inhibitor is used to treat or prevent or inhibit metastasis in a patient with advanced lung cancer. In some aspects, the Src kinase inhibitor is used in combination with a second treatment. In some aspects, the second treatment is any treatment described herein.

In another aspect, the treatment is a COX-2 inhibitor. In some aspects, the COX-2 inhibitor is used to prevent or inhibit metastasis. In some aspects, the COX-2 inhibitor is selected from the group: ABT963, Acetaminophen ER JOHNSON (acetaminophen); Acular X (ketorolac tromethamine), BAY1019036 (aspirin), BAY987111 (diphenhydramine, naproxen sodium), BAY11902 (piroxicam), BCIBUCH001 (ibuprofen), Capoxigem (apricoxib), CS502, CS670 (pelubiprofen), Diclofenac HPBCD (diclofenac), Diractin (ketoprofen), GW406381, HCT1026 (nitroilurbiprofen), Hyanalgese-D (diclofenac), HydrocoDex (acetaminophen, dextromethorphan, hydrocodone), Ibuprofen Sodium PFIZER (ibuprofen sodium), Ibuprofen with Acetaminophen PFIZER (acetaminophen, ibuprofen), Impracor (ketoprofen), IP880 (diclofenac); IP940 (indomethacin), ISV205 (diclofenac Sodium), JNS013 (acetaminophen, tramadol hydrochloride), Ketoprofen TDS (ketoprofen), LTNS001 (naproxen etemesil), Mesalamine SALIX (mesalamine), Mesalamine SOFAR (mesalamine), Mesalazine (mesalamine), ML3000 (licofelone), MRX7EAT (etodolac), Naproxen IROKO (naproxen), NCX4016 (nitroaspirin), NCX701 (nitroacetaminophen), Nuprin SCOLR (ibuprofen), OMS103HP (amitriptyline hydrochloride, ketoprofen, oxymetazoline hydrochloride), Oralease (diclofenac), OxycoDex (dextromethorphan, oxycodone), P54, PercoDex (acetaminophen, dextromethorphan, oxycodone), PL3100 (naproxen, phosphatidyl choline), PSD508, R-Ketoprofen (ketoprofen), Remura (bromfenac sodium), ROX828 (ketorolac tromethamine), RP19583 (ketoprofen lysine), RQ00317076, SDX101 (R-etodolac), TDS943 (diclofenac sodium), TDT070 (ketoprofen), TPR100, TQ1011 (ketoprofen), TT063 (S-flurbiprofen), UR8880 (cimicoxib), V0498TA01A (ibuprofen), VT122 (etodolac, propranolol), XP20B (acetaminophen, dextropropoxyphene), XP21B (diclofenac potassium), XP21L (diclofenac potassium), Zoenasa (acetylcysteine, mesalamine), Acephen, Actifed Plus, Actifed-P, Acular, Acular LS, Acular PF, Acular X, Acuvail, Advil, Advil Allergy Sinus, Advil Cold and Sinus, Advil Congestion Relief, Advil PM, Advil PM Capsule, Air Salonpas, Airtal, Alcohol-Free NyQuil Cold & Flu Relief, Aleve, Aleve ABDI IBRAHIM, Aleve-D, Alka-Seltzer, Alka-Seltzer BAYER, Alka-Seltzer Extra Strength, Alka-Seltzer Lemon-Lime, Alka-Seltzer Original, Alka-Seltzer Plus, Alka-Seltzer plus Cold and Cough, Alka-Seltzer plus Cold and Cough Formula, Alka-Seltzer Plus Day and Night Cold Formula, Alka-Seltzer Plus Day Non-Drowsy Cold Formula, Alka-Seltzer Plus Flu Formula, Alka-Seltzer Plus Night Cold Formula, Alka-Seltzer Plus Sinus Formula, Alka-Seltzer Plus Sparkling Original Cold Formula, Alka-Seltzer PM, Alka-Seltzer Wake-Up Call, Anacin, Anaprox, Anaprox MINERVA, Ansaid, Apitoxin, Apranak, Apranax abdi, Arcoxia, Arthritis Formula Bengay, Arthrotec, Asacol, Asacol HD, Asacol MEDUNA ARZNEIMITTEL, Asacol ORIFARM, Aspirin BAYER, Aspirin Complex, Aspirin Migran, AZD3582, Azulfidine, Baralgan M, BAY1019036, BAY987111, BAY11902, BCIBUCH001, Benadryl Allergy, Benadryl Day and Night, Benylin 4 Flu, Benylin Cold and Flu, Benylin Cold and Flu Day and Night, Benylin Cold and Sinus Day and Night, Benylin Cold and Sinus Plus, Benylin Day and Night Cold and Flu Relief, Benylin1 All-In-One, Brexin, Brexin ANGELINI, Bromday, Bufferin, Buscopan Plus, Caldolor, Calmatel, Cambia, Canasa, Capoxigem, Cataflam, Celebrex, Celebrex ORIFARM, Children's Advil Allergy Sinus, Children's Tylenol, Children's Tylenol Cough and Runny Nose, Children's Tylenol plus cold, Children's Tylenol plus Cold and Cough, Children's Tylenol plus cold and stuffy nose, Children's Tylenol plus Flu, Children's Tylenol plus cold & allergy, Children's Tylenol plus Cough & Runny Nose, Children's Tylenol plus Cough & Sore Throat, Children's Tylenol plus multi symptom cold, Clinoril, Codral Cold and Flu, Codral Day and Night Day Tablets, Codral Day and Night Night Tablets, Codral Nighttime, Colazal, Combunox, Contac Cold plus Flu, Contac Cold plus Flu Non-Drowsy, Coricidin D, Coricidin HBP Cold and Flu, Coricidin HBP Day and Night Multi-Symptom Cold, Coricidin HBP Maximum Strength Flu, Coricidin HBP Nighttime Multi-Symptom Cold, Coricidin II Extra Strength Cold and Flu, CS502, CS670, Daypro, Daypro Alta, DDS06C, Demazin Cold and Flu, Demazin Cough, Cold and Flu, Demazin day/night Cold and Flu, Demazin PE Cold and Flu, Demazin PE day/night Cold and Flu, Diclofenac HPBCD, Dimetapp Day Relief, Dimetapp Multi-Symptom Cold and Flu, Dimetapp Night Relief, Dimetapp Pain and Fever Relief, Dimetapp PE Sinus Pain, Dimetapp PE Sinus Pain plus Allergy, Dipentum, Diractin, Disprin Cold 'n' Fever, Disprin Extra, Disprin Forte. Disprin Plus, Dristan Cold, Dristan Junior, Drixoral Plus, Duexis, Dynastat, Efferalgan, Efferalgan Plus Vitamin C, Efferalgan Vitamin C, Elixsure IB, Excedrin Back and Body, Excedrin Migraine, Excedrin PM, Excedrin Sinus Headache, Excedrin Tension Headache, Falcol, Fansamac, Feldene, Fever-All, Fiorinal, Fiorinal with Codeine, Flanax, Flector Patch, Flucam, Fortagesic, Gerbin, Giazo, Gladio, Goody's Back and Body Pain, Goody's Cool Orange, Goody's Extra Strength, Goody's PM, Greaseless Bengay, GW406381, HCT1026, He Xing Yi, Hyanalgese-D, HydrocoDex, Ibuprofen Sodium PFIZER, Ibuprofen with, Acetaminophen PFIZER, Icy Hot SANOFI AVENTIS, Impracor, Indocin, Indomethacin APP PHARMA, Indomethacin MYLAN, Infants' Tylenol, IP880, IP940, Iremod, ISV205, JNS013, Jr. Tylenol, Junifen, Junior Strength Advil, Junior Strength Motrin, Ketoprofen TDS, Lemsip Max, Lemsip Max All in One, Lemsip Max All Night, Lemsip Max Cold and Flu, Lialda, Listerine Mouth Wash, Lloyds Cream, Lodine, Lorfit P, Loxonin, LTNS001, Mersyndol, Mesalamine SALIX, Mesalamine SOFAR, Mesalazine, Mesasal GLAXO, Mesasal SANOFI, Mesulid, Metsal Heat Rub, Midol Complete, Midol Extended Relief, Midol Liquid Gels, Midol PM, Midol Teen Formula, Migranin COATED TABLETS, ML3000, Mobic, Mohrus, Motrin, Motrin Cold and Sinus Pain, Motrin PM, Movalis ASPEN, MRX7EAT, Nalfon, Nalfon PEDTNOL, Naprelan, Naprosyn, Naprosyn RPG LIFE SCIENCE, Naproxen IROKO, NCX4016, NCX701, NeoProfen LUNDBECK, Nevanac, Nexcede, Niflan, Norgesic MEDICIS, Novalgin, Nuprin SCOLR, Nurofen, Nurofen Cold and Flu, Nurofen Max Strength Migraine, Nurofen Plus, Nuromol, NyQuil with Vitamin C, Ocufen, GMS103HP, Oralease, Orudis ABBOTT JAPAN, Oruvail, Osteluc, OxycoDex, P54, Panadol, Panadol Actifast, Paradine, Paramax, Parfenac, Pedea, Pennsaid, Pentasa, Pentasa ORIFARM, Peon, Percodan, Percodan-Demi, PercoDex, Percogesic, Perfalgan, PL2200, PL3100, Ponstel, Prexige, Prolensa, PSD508, R-Ketoprofen, Rantudil, Relafen, Remura, Riobaxisal, Rotec, Rowasa, ROX828, RP19583, RQ00317076, Rubor, Salofalk, Salonpas, Saridon, SDX101, Seltouch, sfRowasa, Shinbaro, Sinumax, Sinutab, Sinutab, sinus, Spalt, Sprix, Strefen, Sudafed Cold and Cough, Sudafed Head Cold and Sinus, Sudafed PE Cold plus Cough, Sudafed PE Pressure plus Pain, Sudafed PE, Severe Cold, Sudafed PE Sinus Day plus Night Relief Day Tablets, Sudafed PE Sinus Day plus Night Relief Night Tablets, Sudafed PE Sinus plus Anti-inflammatory Pain Relief, Sudafed Sinus Advance, Surgam, Synalgos-DC, Synflex, Tavist allergy/sinus/headache, TDS943, TDT070, Theraflu Cold and Sore Throat, Theraflu Daytime Severe Cold and Cough, Theraflu Daytime Warming Relief, Theraflu Warming Relief Caplets Daytime Multi-Symptom Cold, Theraflu Warming Relief Cold and Chest Congestion, Thomapyrin, Thomapyrin C, Thomapyrin Effervescent, Thomapyrin Medium, Tilcotil, Tispol, Tolectin, Toradol, TPR100, TQ1011, Trauma-Salbe, Trauma-Salbe Kwizda, Treo, Treximet, Trovex, TT063, Tylenol, Tylenol Allergy Multi-Symptom; Tylenol Back Pain, Tylenol Cold & Cough Daytime, Tylenol Cold & Cough Nighttime, Tylenol Cold and Sinus Daytime, Tylenol Cold and Sinus Nighttime, Tylenol Cold Head Congestion Severe, Tylenol Cold Multi Symptom Daytime, Tylenol Cold Multi Symptom Nighttime Liquid, Tylenol Cold Multi Symptom Severe, Tylenol Cold Non-Drowsiness Formula, Tylenol Cold Severe Congestion Daytime, Tylenol Complete Cold, Cough and Flu Night time, Tylenol Flu Nighttime, Tylenol Menstrual, Tylenol PM, Tylenol Sinus Congestion & Pain Daytime, Tylenol Sinus Congestion & Pain Nighttime, Tylenol Sinus Congestion & Pain Severe, Tylenol Sinus Severe Congestion Daytime, Tylenol Ultra Relief, Tylenol with Caffeine and Codeine phosphate, Tylenol with Codeine phosphate, Ultra Strength Bengay Cream, Ultracet, UR8880, V0498TA01A, Vicks NyQuil Cold and Flu Relief, Vicoprofen, Vimovo, Voltaren Emulgel, Voltaren GEL, Voltaren NOVARTIS CONSUMER HEALTH GMBH, Voltaren XR, VT122, Xefo, Xefo Rapid, Xefocam, Xibrom, XL3, Xodol, XP20B, XP21B, XP21L, Zipsor, and Zoenasa. In another aspect, COX-2 inhibitors can be identified through methods known in the art (See, e.g., Dannhardt, G. and Kiefer, W. Cyclooxygenase inhibitors—current status and future prospects. 2001. *Eur. J. Med. Chem.* 36:109-126, which is herein incorporated by reference). In some aspects, the COX-2 inhibitor is used to treat or prevent or inhibit metastasis in a patient with advanced lung cancer. In some aspects, the COX-2 inhibitor is used in combination with a second treatment. In some aspects, the second treatment is any treatment described herein. In some aspects, the COX-2 inhibitor is used in combination with a second treatment selected from the group consisting of: Denosumab, Zometa (http://www.us.zometa.com/index.jsp?usertrack.filter_applied=true&NovaId=2935376934467633633; last accessed Dec. 2, 2012), Carbozantinib or Cabozantinib, Antibody or peptide blocking PTHLH (parathyroid hormone like hormone) or PTHrP (parathyroid hormone related protein).

In another aspect, the treatment agents used for avoiding and/or preventing bone degradation include, but are not limited to:
Parathyroid hormone (PTH) and Parathyroid like hormone (PTHLH) inhibitors (including blocking antibodies) or recombinant forms thereof (teriparatide corresponding to the amino acids 7-34 of PTH). This hormone acts by stimulating the osteoclasts, and increasing their activity.
Strontium ranelate: is an alternative oral treatment, and forms part of the group of drugs called "dual action bone agents" (DABAs) because they stimulate the osteoblast proliferation and inhibit the osteoclast proliferation.
"Estrogen receptor modulators" (SERM) refers to compounds which interfere or inhibit the binding of estrogens to the receptor, regardless of the mechanism. Examples of estrogen receptor modulators include, among others, estrogens progestagen, estradiol, droloxifene, raloxifene, lasofoxifene, TSE-424, tamoxifen, idoxifene, L Y353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4'dihydroxybenzophenone-2,4-dinitrophenyl-hydrazone and SH646.
Calcitonin: directly inhibits the osteoclast activity through the calcitonin receptor. The calcitonin receptors have been identified on the surface of the osteoclasts.
Bisphosphonates: are a group of medicinal products used for the prevention and the treatment of diseases with bone resorption and reabsorption such as osteoporosis and cancer with bone metastasis, the latter being with or without hypercalcaemia, associated to breast cancer and prostate cancer. Examples of bisphosphonates which can be used in the therapy designed by means of the fifth method of the invention, include, although not limited to, nitrogenous bisphosphonates (such as pamidronate, neridronate, olpadronate, alendronate, ibandronate, risedronate, incadronate, zoledronate or zoledronic acid etc.) and non-nitrogenous bisphosphonates (such as etidronate, clodronate, tiludrdnate, etc.).
"Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described in the publications PCT WO 00/55126 of Axys Pharmaceuticals, WO 01/49288 of Merck Frosst Canada & Co. and Axys Pharmaceuticals.
"DKK-1 (Dickkopf-1) inhibitor" as used herein refers to any compound which is capable of reducing DKK-1 activity. DKK-1 is a soluble Wnt pathway antagonist expressed predominantly in adult bone and upregulated in myeloma patients with osteolytic lesions. Agents targeting DKK-1 may play a role in preventing osteolytic bone disease in multiple myeloma patients. BHQ880 from Novartis is a first-in-class, fully human, anti-DKK-1 neutralizing antibody. Preclinical studies support the hypothesis that BHQ880 promotes bone formation and thereby inhibits tumor-induced osteolytic disease (Ettenberg S. et al., American Association for Cancer Research Annual Meeting, Apr. 12-16, 2008; San Diego, Calif. Abstract).

"Dual MET and VEGFR2 inhibitor" as used herein refers to any compound which is a potent dual inhibitor of the MET and VEGF pathways designed to block MET driven tumor escape. MET is expressed not only in tumor cells and endothelial cells, but also in osteoblasts (bone-forming cells) and osteoclasts (bone-removing cells). HGF binds to MET on all of these cell types, giving the MET pathway an important role in multiple autocrine and paracrine loops. Activation of MET in tumor cells appears to be important in the establishment of metastatic bone lesions. At the same time, activation of the MET pathway in osteoblasts and osteoclasts may lead to pathological features of bone metastases, including abnormal bone growth (ie, blastic lesions) or destruction (ie, lytic lesion. Thus, targeting the MET pathway may be a viable strategy in preventing the establishment and progression of metastatic bone lesions. Cabozantinib (Exelixis, Inc), formerly, known as XL184 (GAS 849217-68-1), is a potent dual inhibitor of the MET and VEGF pathways designed to block MET driven tumor escape. In multiple preclinical studies cabozantinib has been shown to kill tumor cells, reduce metastases, and inhibit angiogenesis (the formation of new blood vessels necessary to support tumor growth). Another suitable dual inhibitors are E7050 (N-[2-Fluoro-4-({2-[4-(4-methylpiperazin-1-yl) piperidin-1-yl]carbonylaminopyridin-4-} oxy) phenyl]-N'-(4-fluorophenyl) cyclopropane-1,1-dicarboxamide (2R,3R)-tartrate) (GAS 928037-13-2) or Foretinib (also known as GSK1363089, XO880, CAS 849217-64-7).

"RANKL inhibitors" as used herein refer to any compound which is capable of reducing the RANK activity. RANKL is found on the surface of the osteoblast membrane of the stroma and T-lymphocyte cells; and these T-lymphocyte cells are the only ones which have demonstrated the capacity for secreting it. Its main function is the activation of the osteoclasts cells involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:

a suitable RANK protein which is capable of binding RANKL and which comprises the entire or a fragment of the extracellular domain of a RANK protein. The soluble RANK, may comprise the signal peptide and the extracellular domain of the murine or human RANK polypeptides, or alternatively, the mature form of the protein with the signal peptide removed can be used.

Osteoprotegerin or a variant thereof with RANKL-binding capacity.

RANKL-specific antisense molecules

Ribozymes capable of processing the transcribed products of RANKL

Specific anti-RANKL antibodies. "Anti-RANKL antibody or antibody directed against RANKL" is understood herein as all that antibody which is capable of binding specifically to the ligand of the activating receptor for the nuclear factor κB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described, by Kohler, Milstein et al (Nature, 1975, 256: 495). Antibodies suitable in the context of the present invention include intact antibodies which comprise a variable, antigen binding region and a constant region, fragments "Fab", "F(ab')2" and "Fab", Fv, scFv, diabodies and bispecific antibodies.

Specific anti-RANKL nanobodies. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. The general structure Of nanobodies is

FR1-CDR1-FR2-CDR2-FR3-CPR3-FR4 wherein FR1 to FR4 are the framework regions 1 to 4 CDR1 to CDR3 are the complementarity determining regions 1 to 3. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. These newly discovered VHH; domains with their unique structural and functional properties form the basis of a new generation of therapeutic antibodies which Ablynx has named Nanobodies.

In one embodiment, the RANKL inhibitor is selected from the group consisting of a RANKL specific antibody, a RANKL specific nanobody and osteoprotegerin. In a specific embodiment, the anti-RANKL antibody is a monoclonal antibody. In a yet more specific embodiment, the anti-RANKL antibody, is Denosumab (Pageau, Steven C. (2009). mAbs 1 (3): 210-215, CAS number 615258-40-7) (the entire contents of which are hereby incorporated by reference). Denosumab is a fully human monoclonal antibody which binds to RANKL and prevents its activation (it does not bind to the RANK receptor). Various aspects of Denosumab are covered by U.S. Pat. Nos. 6,740,522; 7,411,050; 7,097,834; 7; 364,736 (the entire contents of each of which are hereby incorporated by reference in their entirety). In another embodiment, the RANKL inhibitor an antibody, antibody fragment, or fusion construct that binds the same epitope as Denosumab.

In a preferred embodiment; the anti-RANKL nanobody is any of the nanobodies as described in WO2008142164, (the contents of which are incorporated in the present application by reference). In a still, more preferred embodiment, the anti-RANKL antibody is the ALX-0141 (Ablynx). ALX-0141 has been designed to inhibit bone loss associated with post-menopausal osteoporosis, reumatoid arthritis, cancer and certain medications, and to restore the balance of healthy bone metabolism.

In a preferred embodiment, the agent preventing the bone degradation is selected from the group consisting of a bisphosphonate, a RANKL inhibitor, PTH and PTHLH inhibitor or a PRG analog, strontium ranelate, a DKK-1 inhibitor, a dual MET and VEGFR2 inhibitor, Radium-223 calcitonin, and a cathepsin K inhibitor. In a more preferred embodiment the agent preventing the bone degradation is a bisphosphonate. In a yet more preferred embodiment, the bisphosphonate is the zoledronic acid.

In one embodiment, a CCR5 antagonist is administered to prevent or inhibit metastasis of the primary lung cancer tumor to bone. In one embodiment, the CCR5 antagonist is a large molecule. In another embodiment, the CCR5 antagonist is a small molecule. In some embodiments, the CCR5 antagonist is Maraviroc (Velasco-Veláquez, M. et al. 2012. CCR5 Antagonist Blocks Metastasis of Basal Breast Cancer Cells. *Cancer Research*, 72:3839-3850.) In some embodiments, the CCR5 antagonist is Vicriviroc. Velasco-Veláquez, M. et al 2012. CCR5 Antagonist Blocks Metastasis of Basal Breast Cancer Cells. *Cancer Research*. 72:3839-3850.). In some aspects, the CCR5 antagonist is Aplaviroc (Demarest J. F. et al. 2005. Update on Aplaviroc: An HIV Entry Inhibitor Targeting CCR5. *Retrovirology* 2(Suppl. 1): S13). In some aspects, the CCR5 antagonist is a spiropiperidine CCR5 antagonist. (Rotstein D. M. et al. 2009. Spiropiperidine CCR5 antagonists. *Bioorganic & Medicinal Chemistry Letters*. 19(18): 5401-5406. In some embodiments, the CCR5 antagonist is INCB009471 (Kuritzkes, D. R. 2009. HIV-1 entry inhibitors: an overview. *Curr. Opin. HIV AIDS.* 4(2): 82-7).

In a preferred embodiment the dual MET and VEGFR2 inhibitor is selected from the group consisting of Cabozantinib, Foretinib and E7050.

In a preferred embodiment the Radium 223 therapy is alpharadin.

Alternatively a combined treatment can be carried out in which more than one agent from those mentioned above are combined to treat and/or prevent the metastasis or said agents can be combined with other supplements, such as calcium or vitamin D or with a hormone treatment.

Method for Designing Customized Therapy of the Invention in Lung Cancer Patients with Bone Metastasis Patients suffering lung cancer which has already metastasized to the bone and in which there are elevated c-MAF levels may particularly benefit from therapies aimed at preventing the bone degradation caused by the increased osteoclastic activity.

Thus, in another aspect, the invention relates to an in vitro method for designing a customized therapy for a subject with lung cancer with bone metastasis (hereinafter third method of the invention) which comprises
  (i) quantifying the c-MAF gene expression level in a metastatic tumor sample from bone of said subject, and
  (ii) comparing the expression/level previously obtained with the expression level of said gene in a control sample,
wherein if the expression levels are increased with respect to the expression levels of said gene in the control sample, then said subject is susceptible to receive a therapy aiming to prevent the bone degradation.
wherein if the expression level is not increased with respect to said reference value, then said subject is not susceptible to receive a therapy aiming to prevent and/or treat the bone metastasis.

The terms and expressions "subject", "lung cancer", "tumor sample", "metastasis", "determination of expression levels", "c-MAF gene", "increased expression levels" and "control sample" have been described in detail in relation to the first method of the invention and are equally applicable to the second and third method of the invention.

In a preferred embodiment, the bone metastasis is osteolytic metastasis.

The third method of the invention comprises in a first step, quantifying the c-MAF gene expression level in a tumor sample in a subject suffering lung cancer. In the case of the third method of the invention, the sample is a tissue sample from bone metastasis.

In a preferred embodiment, the third method of the invention comprises quantifying only the c-MAF gene expression level as a single marker, i.e., the method does not involve determining the expression level of any additional marker.

In a second step the c-MAF gene expression level obtained in the tumor sample of the subject is compared with the expression level of said gene in a control sample. The determination of the c-MAF gene expression levels must be correlated to values of a control sample or reference sample. Depending on the type of tumor to be analyzed, the exact nature of the control sample may vary. Thus, in the case involving the third method of the invention, then the reference sample is a tumor tissue sample of subject with lung cancer who has not suffered metastasis or that correspond to the median value of the c-MAF gene expression levels measured in a tumor tissue collection in biopsy samples of subjects with lung cancer who has not suffered metastasis.

Once the c-MAF gene expression level in the sample is measured and compared with the control sample, if the expression level of said gene are increased with respect to its expression levels in the control sample, then it can be concluded that said subject is susceptible to receive a therapy aiming to avoid or prevent bone degradation.

As used herein, an "agent for avoiding or preventing bone degradation" refers to any molecule capable of treating or stopping bone degradation either by stimulating the osteoblast proliferation or inhibiting the osteoclast proliferation.

Illustrative examples of agents used for avoiding and/or preventing bone degradation and/or bone metastasis include, although not limited to:

Parathyroid hormone (PTH) or recombinant forms thereof (teriparatide corresponding to the amino acids 1-34 of PTH). This hormone acts by stimulating the osteoblasts and increasing their activity.

Strontium ranelate: is an alternative oral treatment, and forms part of the group of drugs called "dual action/bone agents" (DABAs) because they stimulate the osteoblast proliferation and inhibit the osteoclast proliferation.

"Estrogen receptor modulators" (SERM) refers to compounds which interfere or inhibit the binding of estrogens to the receptor, regardless of the mechanism. Examples of estrogen receptor modulators include, among others, estrogens progestagen, estradiol, droloxifene, raloxifene, lasofoxifene, TSE-424, tamoxifen, idoxifene, L Y353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4'dihydroxybenzophenone-2,4-dinitrophenyl-hydrazone and SH646.

Calcitonin: directly inhibits the osteoclast activity through the calcitonin receptor. The calcitonin receptors have been identified, on the surface of the osteoclasts.

Bisphosphonates: are a group of medicinal products used for the prevention and the treatment of diseases with bone resorption and reabsorption such as osteoporosis and cancer with bone metastasis, the latter being with or without hypercalcaemia; associated to breast cancer and prostate cancer. Examples of bisphosphonates which cane be used in the therapy designed by means of the third method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.).

"Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described/in the publications PCT WO 00/55126 of Axys Pharmaceuticals, WO 01/49288 of Merck Frosst Canada & Co. and Axys Pharmaceuticals.

"DKK-1 (Dickkopf-1) inhibitor" as used herein refers to any compound which is capable of reducing DKK-1 activity. DKK-1 is a soluble Wnt pathway antagonist expressed predominantly in adult bone and upregulated in myeloma patients with osteolytic lesions. Agents targeting DKK-1 may play a role in preventing osteolytic bone disease in multiple myeloma patients. BHQ880 from Novartis is a first-in-class, fully human, anti-DKK-1 neutralizing antibody. Preclinical studies support the hypothesis that BHQ880 promotes bone formation and thereby inhibits tumor-induced osteolytic disease. (Ettenberg S. et al., American Association for Cancer Research Annual Meeting. Apr. 12-16, 2008; San Diego, Calif. Abstract).

"Dual MET and VEGFR2 inhibitor" as used herein refers to any compound which is a potent dual inhibitor of the MET and VEGF pathways designed to block MET driven tumor escape. MET is expressed not only in tumor cells and endothelial cells, but also, in osteoblasts (bone-forming cells) and osteoclasts (bone-removing cells). HGF binds to MET on all of these cell types, giving the MET pathway an important role in multiple autocrine and paracrine loops. Activation of MET in tumor cells appears to be important in the establishment of metastatic bone lesions. At the same time, activation of the MET pathway in osteoblasts and osteoclasts may lead to pathological features of bone metastases, including abnormal bone growth (ie, blastic lesions) or destruction (ie, lytic lesion. Thus, targeting the MET pathway may be a viable strategy in preventing the establishment and progression of metastatic bone lesions. Cabozantinib (Exelixis, Inc), formerly known as XL184 (CAS 849217-68-1), is a potent dual inhibitor of the MET and VEGF pathways designed to block MET driven tumor escape. In multiple preclinical studies cabozantinib has been shown to kill tumor cells, reduce metastases, and inhibit angiogenesis (the formation of new blood vessels necessary to support tumor growth). Another suitable dual inhibitors are E7050 (N-[2-Fluoro-4-({2-[4-(4-methylpiperazin-1-yl)piperidin-1-yl]carbonylaminopyridin-4-yl}oxy)phenyl]-N'-(4-fluorophenyl)cyclopropane-1,1-dicarboxamide (2R,3R)-tartrate) (CAS 928037-13-2) or Foretinib (also known as GSK1363089, XL880, CAS 849217-64-7).

"RANKL inhibitors" as used herein refers to any compound which is capable of reducing the RANK activity. RANKL is found on the surface of the osteoblast membrane of the stroma and T-lymphocyte cells, and these T-lymphocyte cells are the only ones which have demonstrated the capacity for secreting it. Its main function is the activation of the osteoclasts, cell's involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:

a suitable RANK protein which is capable of binding RANKL and which comprises the entire or a fragment of the extracellular domain of a RANK protein. The soluble RANK may comprise the signal peptide and the extracellular domain of the murine or human RANK polypeptides, or alternatively, the mature form of the protein with the signal peptide removed can be used.

Osteoprotegerin or a variant thereof with RANKL-binding capacity.

RANKL-specific antisense molecules

Ribozymes capable of processing the transcribed products of RANKL

Specific anti-RANKL antibodies. "Anti-RANKL antibody or antibody directed against RANKL" is understood herein as all that antibody which is capable of binding specifically to the ligand of the activating receptor for the nuclear factor κB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described by Kohler, Milstein et al. (Nature, 1975, 256: 495). Antibodies suitable in the context of the present invention include intact antibodies which comprises a variable antigen binding region and a constant region, fragments "Fab", "F(ab')2" and "Fab"', Fv, scFv, diabodies and bispecific antibodies.

Specific anti-RANKL nanobodies. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. The general structure of nanobodies is FR1-CDR1-FR2-CDR2-FR3-CDR3-FR4 wherein FR1 to FR4 are the framework regions 1 to 4 CDR1 to CDR3 are the complementarity determining regions 1 to 3. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. These newly discovered VHH domains with their unique structural and functional propertied form the basis of a new generation of therapeutic antibodies which Ablynx has named Nanobodies.

In one embodiment, the RANKL inhibitor is selected from the group consisting of a RANKL specific antibody, a RANKL specific nanobody and osteoprotegerin. In a preferred embodiment, the anti-RANKL antibody is a monoclonal antibody. In a yet more preferred embodiment, the anti-RANKL antibody is Denosumab (Pageau, Steven C. (2009). mAbs 1 (3): 210-215, CAS number 615258-40-7).

In the context of the present invention, Denosumab is a monoclonal antibody which binds to RANKL and prevents its activation (it does not bind to the RANK receptor). Various aspects of Denosumab are covered by U.S. Pat. Nos. 6,740,522; 7,411,050; 7,097,834; 7,364,736 (the entire contents of each of which are hereby incorporated by reference in their entirety). In another embodiment, the RANKL inhibitor is an antibody, antibody fragment, or fusion construct that binds the same epitope as Denosumab.

In a preferred embodiment, the anti-RANKL nanobody is any of the nanobodies as described in WO2008142164, (the contents of which are incorporated in the present application by reference). In a still more preferred embodiment, the anti-RANKL antibody is the ALX-0141 (Ablynx). ALX-0141 has been designed to inhibit bone loss associated with post-menopausal osteoporosis, rheumatoid arthritis, cancer and certain medications, and to restore the balance of healthy bone metabolism.

In a preferred embodiment, the agent preventing the bone degradation is selected from the group consisting of a bisphosphonate, a RANKL inhibitor, PTH and PTHLH inhibitor or a PRG analog, strontium ranelate, a DKK-1 inhibitor, a dual MET and VEGFR2 inhibitor, an estrogen receptor modulator, Radium-223 calcitonin, and a cathepsin K inhibitor. In a more preferred embodiment the agent preventing the bone degradation is a bisphosphonate. In a yet more preferred embodiment, the bisphosphonate is the zoledronic acid.

In one embodiment, a CCR5 antagonist is administered to prevent or inhibit metastasis of the primary lung cancer tumor to bone. In one embodiment, the CCR5 antagonist is a large molecule. In another embodiment, the CCR5 antagonist is a small molecule. In some embodiments, the CCR5 antagonist is Maraviroc (Velasco-Veláquez, M. et. al. 2012. CCR5 Antagonist Blocks Metastasis of Basal Breast Cancer Cells. Cancer Research. 72:3839-3850.). In some embodiments, the CCR5 antagonist is Vicriviroc. Velasco-Veláquez, M. et al. 2012. CCR5 Antagonist Blocks Metastasis of Basal Breast Cancer Cells. Cancer Research. 72:3839-3850). In some aspects, the CCR5 antagonist is Aplaviroc (Demarest J. F. et al. 2005. Update on Aplaviroc: An HIV Entry Inhibitor Targeting CCR5. Retrovirology 2(Suppl. 1): S13). In some aspects, the CCR5 antagonist is a spiropiperidine CCR5 antagonist. (Rotstein D. M. et al. 2009. Spiropiperidine CCR5 antagonists. Bioorganic & Medicinal Chemistry Letters. 19 (18): 5401-5406. In some embodiments, the CCR5 antagonist is INCB009471 (Kuritzkes, D. R. 2009. HIV-1 entry inhibitors: an overview. Curr. Opin. HIV AIDS. 4(2): 82-7).

In a preferred embodiment the dual MET and VEGFR2 inhibitor is selected from the group consisting of Cabozantinib, Foretinib and E7050.

In another aspect, the treatment is an mTor inhibitor. In some aspects, the mTor inhibitor is a dual mTor/PI3kinase inhibitor. In some aspects, the mTor inhibitor is used to prevent or inhibit metastasis. In some aspects the mTor inhibitor is selected, from the group consisting of: ABI009 (sirolimus), rapamycin (sirolimus), Abraxane (paclitaxel), Absorb (everolimus); Afinitor (everolimus), Afinitor with Gleevec, AS703026 (pimasertib), Axxess (umirolimus), AZD2014, BEZ235, Biofreedom (umirolimus), BioMatrix (umirolimus), BioMatrix flex (umirolimus), CC115, CC223, Combo Bio-engineered Sirolimus Eluting Stent ORBUSNEICH (sirolimus), Curaxin CBLC102 (mepacrine), DE109 (sirolimus), DS3078, Endeavor DES (zotarolimus), Endeavor Resolute (zotarolimus); Femara (letrozole), Hocena (antroquinonol), INK128, Inspiron (sirolimus), IPI504 (retaspimycin hydrochloride), KRN951 (tivozanib), ME344, MGA031 (teplizumab), MiStent SES (sirolimus), MKC1, Nobori (umirolimus), OSI027, OVI123 (cordycepin), Palomid 529, PF04691502, Promus Element (everolimus), PWT33597, Rapamune (sirolimus), Resolute DES (zotarolimus), RG7422, SAR245409, SF1126, SGN75 (vorsetuzumab mafodotin), Synergy (everolimus), Taltorvic (ridaforolimus), Tarceva (erlotinib), Torisel (temsirolimus), Xience Prime (everolimus), Xience V (everolimus), Zomaxx (zotarolimus), Zortress (everolimus), Zotarolimus Eluting Peripheral Stent MEDTRONIC (zotarolimus), AP23841, AP24170, ARmTOR26, BN107, BN108, Canstatin GENZYME (canstatin), CU906, EC0371, EC0565, KI1004, LOR220, NV128, Rapamycin ONCOIMMUNE (sirolimus), SB2602, Sirolinius PNP SAMYANG BIOPHARMACEUTICALS (sirolimus), TOP216, VLI27, VS5584, WYE125132, XL388, Advacan (everolimus); AZD8055, Cypher Select Plus Sirolimus eluting Coronary Stent (sirolimus), Cypher Sirolimus eluting coronary stent (sirolimus), Drug Coated Balloon (sirolimus), E-Magic Plus (sirolimus), Emtor (sirolimus), Esprit (everolimus), Evertor (everolimus), HBF0079, LCP-Siro (sirolimus), Limus CLARIS (sirolimus), mTOR Inhibitor CELLZOME, Nevo Sirolimus eluting Coronary Stent (sirolimus), nPT-mTOR, Rapacan (sirolimus), Renacept (sirolimus), ReZolve (sirolimus), Rocas (sirolimus), SF1126, Sirolim (sirolimus), Sirolimus NORTH CHINA (sirolimus), Sirolimus RANBAXY (sirolimus), Sirolimus WATSON (sirolimus), Siropan (sirolimus), Sirova (sirolimus), Supralimus (sirolimus), Supralimus-Core (sirolimus), Tacrolimus WATSON (tacrolimus), TAFA93, Temsirolimus ACCORD (temsirolimus), Temsirolimus SANDOZ (temsirolimus), TOP216, Xience Prime, (everolimus), Xience V (everolimus). In a specific aspect the mTor inhibitor is Afinitor (everolimus) (http://www.afinitor.com/index.jsp?usertrack.filter_applied=true&NovaId= 40294620643 38207963; last accessed Nov. 28, 2012). In another aspect, mTor inhibitors can be identified through methods known in the art. (See, e.g., Zhou, H. et al. Updates of mTor inhibitors. 2010. Anticancer Agents Med. Chem. 10(7): 571-81, which is herein incorporated by reference). In some aspects, the mTor inhibitor is used to treat or prevent or inhibit metastasis in a patient with advanced lung cancer. In some aspects, the mTor inhibitor is used in combination with a second treatment. In some aspects, the second treatment is any treatment described herein.

In another aspect, the treatment is a Src kinase inhibitor. In some aspects, the Src inhibitor is used to prevent or inhibit metastasis. In some aspects, the Src kinase inhibitor is selected from the group: AZD0530 (saracatinib), Bosulif (bosutinib), ENMD981693, KD020, KX01, Sprycel (dasatinib), Yervoy (ipilimumab), AP23464, AP23485, AP23588, AZD0424, c-Src Kinase Inhibitor KISSEI, CU201, KX2361, SKS927, SRN004, SUNK706, TG100435, TG100948, AP23451, Dasatinib HETERO (dasatinib), Dasatinib VALEANT (dasatinib), Fontrax (dasatinib), Src Kinase Inhibitor KINEX, VX680, (tozasertib lactate), XL228, and SUNK706. In some embodiments, the Src kinase inhibitor is dasatinib. In another aspect, Src kinase inhibitors can be identified through methods known in the art (See, e.g., Sen, B. and Johnson, F. M. Regulation of Src Family Kinases in Human Cancers. 2011, *J. Signal Transduction*. 2011: 14 pages, which is herein incorporated by reference). In some aspects, the Src kinase inhibitor is used to treat or prevent or inhibit metastasis in a patient that is positive for the SRC-responsive signature (SRS). In some aspects, the patient is SRS+(See, e.g., Zhang, C H. F, et al.

Latent Bone Metastasis in Breast Cancer Tied to Src-Dependent survival signals. 2009. *Cancer Cell.* 16:67-78, which is herein incorporated by reference.) In some aspects, the Src kinase inhibitor is used to treat or prevent or inhibit metastasis in a patient with advanced lung cancer. In some aspects, the Src kinase inhibitor is used in combination with a second treatment. In some aspects, the second treatment is any treatment described herein.

In another aspect, the treatment is a COX-2 inhibitor. In some aspects, the COX-2 inhibitor is used to prevent or inhibit metastasis. In some aspects, the COX-2 inhibitor is selected from the group: ABT963, Acetaminophen ER JOHNSON (acetaminophen), Acular X (ketorolac tromethamine), BAY1019036 (aspirin), BAY987111 (diphenhydramine, naproxen sodium), BAY11902 (piroxicam), BCI-BUCH001 (ibuprofen); Capoxigem (apricoxib), CS502, CS670 (pelubiprofen), Diclofenac HPBCD (diclofenac), Diractin (ketoprofen), GW406381, HCT1026 (nitroflurbiprofen), Hyanalgese-D (diclofenac), HydrocoDex (acetaminophen, dextromethorphan, hydrocodone), Ibuprofen Sodium PFIZER (ibuprofen sodium), Ibuprofen with Acetaminophen PFIZER (acetaminophen, ibuprofen), Impracor (ketoprofen), IP880 (diclofenac), IP940 (indomethacin), ISV205 (diclofenac, sodium), JNS013 (acetaminophen, tramadol hydrochloride), Ketoprofen TDS (ketoprofen), LTNS001 (naproxen etemesil), Mesalamine SAL1X (mesalamine), Mesalamine SOFAR (mesalamine), Mesalazine (mesalamine), ML3000 (licofelone), MRX7EAT (etodolac), Naproxen IROKO (naproxen), NCX4016 (nitroaspirin), NCX701 (nitroacetaminophen), Nuprin SCOLR (ibuprofen), OMS103HP (amitriptyline hydrochloride, ketoprofen, oxymetazoline hydrochloride), Oralease (diclofenac), OxycoDex (dextromethorphan, oxycodone), P54, PercoDex (acetaminophen, dextromethorphan, oxycodone), PL3100 (naproxen, phosphatidyl choline), PSD508, R-Ketoprofen (ketoprofen), Remura (bromfenac sodium), ROX828 (ketorolac tromethamine), RP19583 (ketoprofen lysine), RQ00317076, SDX101 (R-etodolac), TDS943 (diclofenac sodium), TDT070 (ketoprofen), TPR100, TQ1011 (ketoprofen), TT063 (S-flurbiprofen), UR8880 (cimicoxib), V0498TA01A (ibuprofen), VT122 (etodolac, propranolol), XP20B (acetaminophen, dextropropoxyphene), XP21B (diclofenac potassium), XP21L (diclofenac potassium), Zoenasa (acetylcysteine, mesalamine), Acephen, Actifed Plus, Actifed-P, Acular, Acular LS, Acular PF, Acular X, Acuvail, Advil, Advil Allergy Sinus, Advil Cold and Sinus, Advil Congestion Relief, Advil PM, Advil PM Capsule, Air Salonpas, Airtal, Alcohol-Free NyQuil Cold & Flu Relief, Aleve, Aleve ABDI IBRAHIM, Aleve-D, Alka-Seltzer, Alka-Seltzer BAYER, Alka-Seltzer Extra Strength, Alka-Seltzer Lemon-Lime, Alka-Seltzer Original, Alka-Seltzer Plus, Alka-Seltzer plus Cold and Cough, Alka-Seltzer plus Cold and Cough Formula, Alka-Seltzer Plus Day and Night Cold Formula, Alka-Seltzer Plus Day Non-Drowsy Cold Formula, Alka-Seltzer Plus Flu Formula, Alka-Seltzer Plus Night Cold Formula, Alka-Seltzer Plus Sinus Formula, Alka-Seltzer Plus Sparkling Original Cold Formula, Alka-Seltzer PM, Alka-Seltzer Wake-Up Call, Anacin, Anaprox, Anaprox MINERVA, Ansaid, Apitoxin, Apranax, Apranax abdi, Arcoxia, Arthritis Formula Bengay, Arthrotec, Asacol, Asacol HD, Asacol MEDUNA ARZNEIMITTEL, Asacol ORIFARM, Aspirin BAYER, Aspirin Complex, Aspirin Migran, AZD3582, Azulfidine, Baralgan M, BAY1019036, BAY987111, BAY11902, BCIBUCH001, Benadryl Allergy, Benadryl Day and Night, Benylin 4 Flu, Benylin Cold and Flu, Benylin Cold and Flu Day and Night, Benylin Cold and Sinus Day and Night, Benylin Cold and Sinus Plus, Benylin Dan and Night Cold and Flu Relief, Benylin1 All-In-One, Brexin, Brexin ANGELINI, Bromday, Bufferin, Buscopan Plus, Caldolor, Calmatel, Cambia, Canasa, Capoxigem, Cataflam, Celebrex, Celebrex ORIFARM, Children's Advil Allergy Sinus, Children's Tylenol, Children's Tylenol Cough and Runny Nose, Children's Tylenol plus cold, Children's Tylenol-plus Cold and Cough, Children's Tylenol plus cold and stuffy nose, Children's Tylenol plus Flu, Children's Tylenol plus cold & allergy, Children's Tylenol plus Cough & Runny Nose, Children's Tylenol plus Cough & Sore Throat, Children's Tylenol, plus multi symptom cold, Clinoril, Codral Cold and Flu, Codral Day and Night Day Tablets, Codral Day and Night Night Tablets, Codral Nightime, Colazal, Combunox, Contac Cold plus Flu, Contac Cold plus Flu Non-Drowsy, Coricidin D, Coricidin HBP Cold and Flu, Coricidin HBP Day and Night Multi-Symptom Cold, Coricidin HBP Maximum Strength Flu, Coricidin HBP Nighttime Multi-Symptom Cold, Coricidin II Extra Strength Cold and Flu, CS502, CS670, Daypro, Daypro Alta, DDS06C, Demazin Cold and Flu, Demazin Cough, Cold and Flu, Demazin day/night Cold and Flu, Demazin PE Cold and Flu, Demazin PE day/night Cold and Flu, Diclofenac HPBCD, Dimetapp Day Relief, Dimetapp Multi-Symptom Cold and Flu, Dimetapp Night Relief, Dimetapp Pain and Fever Relief, Dimetapp PE Sinus Pain, Dimetapp PE Sinus Pain plus Allergy, Dipentum, Diractin, Disprin Cold 'n' Fever, Disprin Extra, Disprin Forte, Disprin Plus, Dristan Cold, Dristan Junior, Drixoral Plus, Duexis, Dynastat, Efferalgan, Efferalgan Plus Vitamin C, Efferalgan Vitamin C, Elixsure IB, Excedrin Back and Body, Excedrin Migraine, Excedrin PM, Excedrin Sinus Headache, Excedrin Tension Headache, Falcol, Fansamac, Feldene, Fever-All, Fiorinal, Fiorinal with Codeine, Flanax, Flector Patch, Flucam, Fortagesic, Gerbin, Giazo, Gladio, Goody's Back and Body Pain; Goody's Cool Orange, Goody's Extra Strength; Goody's PM, Greaseless Bengay, GW406381, HCT1026, He Xing Yi, Hyanalgese-D, HydrocoDex, Ibuprofen Sodium PFIZER, Ibuprofen with, Acetaminophen PFIZER, Icy Hot SANOFI AVENTIS, Impracor, Indocin, Indomethacin APP PHARMA, Indomethacin MYLAN, Infants' Tylenol, IP880, IP940, Iremod, ISV205, JNS013, Jr. Tylenol, Junifen, Junior Strength Advil, Junior Strength Motrin, Ketoprofen TDS, Lemsip Max, Lemsip Max All in One, Lemsip Max All Night, Lemsip Max Cold and Flu, Lialda, Listerine Mouth Wash, Lloyds Cream, Lodine, Lorfit P, Loxonin, LTNS001, Mersyndol, Mesalamine SALIX, Mesalamine SOFAR, Mesalazine, Mesasal GLAXO, Mesasal SANOFI, Mesulid, Metsal Heat Rub, Midol Complete, Midol Extended Relief, Midol Liquid Gels, Midol PM, Midol Teen Formula, Migranin COATED TABLETS, ML3000, Mobic, Mohrus, Motrin, Motrin Cold and Sinus Pain, Motrin PM, Movalis ASPEN, MRX7EAT, Nalfon, Nalfon PEDINOL, Naprelan, Naprosyn, Naprosyn RPG LIFE SCIENCE, Naproxen IROKO, NCX4016, NCX701, NeoProfen LUNDBECK, Nevanac, Nexcede, Niflan, Norgesic MEDICIS, Novalgin, Nuprin SCOLR, Nurofen, Nurofen Cold and Flu, Nurofen Max Strength Migraine, Nurofen Plus, Nuromol, NyQuil with Vitamin C, Ocufen, OMS103HP, Oralease, Orudis ABBOTT JAPAN, Oruvail, Osteluc, OxycoDex, P54, Panadol, Panadol Actifast, Paradine, Paramax, Parfenac, Pedea, Pennsaid, Pentasa, Pentasa ORIFARM, Peon, Percodan, Percodan-Demi, PercoDex, Percogesic, Perfalgan, PL2200, PL3100, Ponstel, Prexige, Prolensa, PSD508, R-Ketoprofen, Rantudil, Relafen, Remura, Robaxisal, Rotec, Rowasa, ROX828, RPI9583, RQ00317076, Rubor, Salofalk, Salonpas, Saridon, SDX101, Seltouch, sfRowasa, Shinbaro, Sinumax, Sinutab, Sinutab, sinus, Spalt, Sprix, Strefen, Sudafed Cold and Cough, Sudafed Head Cold and Sinus, Sudafed PE Cold plus Cough, Sudafed PE Pressure plus Pain, Sudafed PE, Severe Cold, Sudafed PE Sinus Day plus Night Relief Day Tablets, Sudafed PE Sinus Day plus Night Relief Night Tablets, Sudafed PE Sinus plus Anti-inflammatory Pain Relief, Sudafed Sinus Advance, Surgam, Synalgos-DC, Synflex, Tavist allergy/sinus/headache, TDS943, TDT070, Theraflu Cold and Sore Throat, Theraflu Daytime Severe Cold and Cough, Theraflu Daytime Warming Relief, Theraflu Warming, Relief Caplets Daytime Multi-Symptom Cold, Theraflu Warming Relief Cold and Chest Congestion, Thomapyrin, Thomapyrin C, Thomapyrin Effervescent, Thomapyrin Medium, Tilcotil, Tispol, Tolectin, Toradol, TPR100, TQ1011, Trauma-Salbe, Trauma-Salbe Kwizda, Treo, Treximet, Trovex, TT063, Tylenol, Tylenol Allergy Multi-Symptom, Tylenol Back Pain, Tylenol Cold & Cough Daytime, Tylenol Cold & Cough Nighttime, Tylenol Cold and Sinus Daytime, Tylenol Cold and Sinus Nighttime, Tylenol Cold Head Congestion Severe, Tylenol Cold Multi Symptom Daytime, Tylenol Cold Multi Symptom Nighttime Liquid, Tylenol Cold Multi Symptom Severe, Tylenol Cold Non-Drowsiness Formula, Tylenol Cold Severe Congestion Daytime, Tylenol Complete Cold, Cough and Flu Night time, Tylenol Flu Nighttime, Tylenol Menstrual, Tylenol PM, Tylenol Sinus Congestion & Pain Daytime, Tylenol Sinus Congestion & Pain Nighttime, Tylenol Sinus Congestion & Pain Severe, Tylenol Sinus Severe Congestion Daytime, Tylenol Ultra Relief, Tylenol with Caffeine and Codeine phosphate, Tylenol with Codeine phosphate, Ultra Strength Bengay Cream, Ultracet, UR8880, V0498TA01A, Vicks NyQuil Cold and Flu Relief, Vicoprofen Vimovo, Voltaren Emulgel, Voltaren GEL, Voltaren NOVARTIS CONSUMER HEALTH GMBH, Voltaren XR, VT122, Xefo, Xefo Rapid, Xefocam, Xibrom, XL3, Xodol, XP20B, XP21B, XP21L, Zipsor, and Zoenasa. In another aspect, COX-2 inhibitors can be identified through methods known in the art (See, e.g., Dannhardt, G. and Kiefer, W. Cyclooxygenase inhibitors—current status and future prospects, 2001. *Eur. J. Med. Chem*, 36:109-126, which is herein incorporated by reference). In some aspects, the COX-2 inhibitor is used to treat or prevent, or inhibit metastasis in a patient with advanced lung cancer. In some aspects, the COX-2 inhibitor is used in combination with a second treatment. In some aspects, the second treatment is any treatment described herein. In some aspects, the COX-2 inhibitor is used in combination with a second treatment selected from the group consisting of: Denosumab, Zometa (http://www.us.zometa.com/index.jsp?usertrack.filter_applied=true&NovaId=293537693 4467633633; last accessed Dec. 2, 2012), Carbozantinib or Cabozantinib, Antibody or peptide blocking PTHLH (parathyroid hormone like hormone) or PTHrP (parathyroid hormone related protein).

In a preferred embodiment the Radium 223 therapy is Alpharadin (aka, Xofigo) (radium-223 dichloride). Alpharadin uses alpha radiation from radium-223 decay to kill cancer cells. Radium-223 naturally self-targets to bone metastases by virtue of its properties as a calcium-mimic. Alpha radiation has a very short range of 2-10 cells (when compared to current radiation therapy which is based on beta or gamma radiation), and therefore causes less damage to surrounding healthy tissues (particularly bone marrow). With similar properties to calcium, radium-223 is drawn to places where calcium is used to build bone in the body, including the site of faster, abnormal bone growth—such as that seen in the skeletal metastases of men with advanced, castration-resistant prostate cancer. Radium-223, after injection, is carried in the bloodstream to sites of abnormal bone, growth. The place where a cancer starts in the body is known as the primary tumor. Some of these cells may break away and be carried in the bloodstream to another part of the body. The cancer cells may then settle in that part of the body and form a new tumor. If this happens it is called a secondary cancer of a metastasis. Most patients with late stage prostate cancer suffer the maximum burden of disease in their bones. The aim with radium-223 is to selectively target this secondary cancer. Any radium-223 not taken-up in the bones is quickly routed to the gut and excreted. In a preferred embodiment, the agent preventing the bone degradation is a bisphosphonate. In a yet more preferred embodiment, the bisphosphonate is the zoledronic acid.

Alternatively a combined treatment can be carried out in which more than one agent from those mentioned above are combined to treat and/or prevent the metastasis or said agents can be combined with other supplements, such as calcium or vitamin D or with a hormone treatment.

Method of Diagnosis or Prognosis of Metastasis, in Lung Cancer Based on Detecting the Amplification of the c-MAF Gene In one aspect, the invention relates to an in-vitro method for the diagnosis of metastasis in a subject with lung cancer (hereinafter, fourth diagnosis method of the invention) and/or for the prognosis of the tendency to develop metastasis in a subject with lung cancer which comprises determining if the c-MAF gene is amplified in a tumor tissue sample of said subject; wherein if said gene is amplified with respect to a control sample, then said subject has a positive diagnosis for metastasis or a greater tendency to develop metastasis.

In a particular embodiment, the lung cancer diagnosed in the fourth method of the invention is NSCLC.

The terms "c-MAF gene", "metastasis", "tumor sample", "lung cancer", "diagnosis of metastasis in a subject with lung cancer", "prognosis of the tendency to develop metastasis in a subject with lung cancer", "subject", "patient", "subject having a positive diagnosis of metastasis", "subject having a greater tendency to develop metastasis" have been described in detail in the context of the first method of the invention and are equally applicable to the fourth method of the invention.

In a particular embodiment, the degree of amplification of the c-MAF gene can be determined by means of determining the amplification of a chromosome region containing said gene. Preferably, the chromosome region the amplification of which is indicative of the existence of amplification of the c-MAF gene is the locus 16q22-q24 which includes the c-MAF gene. The locus 16q22-q24 is located in chromosome 16, in the long arm of said chromosome and in a range between band 22 and band 24. This region corresponds in the NCBI database with the contigs NT_010498.15 and NT_010542.15. In another preferred embodiment, the degree of amplification of the c-MAF gene can be determined by means of using a probe specific for said gene.

The fourth diagnosis/prognosis method of the invention comprises, in a first step, determining if the c-MAF gene is-amplified in a tumor sample of a subject. To that end, the amplification of the c-MAF gene in the tumor sample is compared with respect to a control sample.

The term, "amplification of a gene" as understood herein refers to a process through which various copies of a gene or of a gene fragment are formed in an individual cell or a cell line. The copies of the gene are not necessarily located in the same chromosome. The duplicated region is often called an "amplicon". Normally, the amount of mRNA produced, i.e., the gene expression level also increases in proportion to the copy number of a particular gene.

In a particular embodiment, the fourth method of the invention for the diagnoses of metastasis in a subject with lung cancer and/or for the prognosis of the tendency to develop metastasis in a subject with lung cancer, comprises determining the c-MAF gene copy number in a tumor sample of said subject and comparing said copy number with the copy number of a control or reference sample, wherein if the c-MAF copy number is greater with respect to the c-MAF copy number of a control sample, then the subject has a positive diagnosis of metastasis or a greater tendency to develop metastasis.

The control sample refers to a tumor sample of a subject with lung cancer who has not suffered metastasis or that correspond to the median value of the c-MAF gene copy number measured in a tumor tissue collection in biopsy samples of subjects with lung cancer who have not suffered metastasis. Said reference sample is typically obtained by combining equal amounts of samples from a subject population. If the c-MAF gene copy number is increased with respect to the copy number of said gene in the control sample then subject has a positive diagnosis for metastasis or a greater tendency to develop metastasis.

As used herein, the term "gene copy number" refers to the copy number of a nucleic acid molecule in a cell. The gene copy number includes the gene copy number in the genomic (chromosomal) DNA of a cell. In a normal cell (non-tumoral cell), the gene copy number is normally two copies (one copy in each member of the chromosome pair). The gene copy number sometimes includes half of the gene copy number taken from samples of a cell population.

In the present invention, "increased gene copy number" is understood as when the c-MAF gene copy number is more than the copy number that a reference sample or control sample has. In particular, it can be considered that a sample has an increased c-MAF copy number when the copy number is more than 2 copies, for example, 3, 4, 5, 6, 7, 8, 9 or 10 copies, and even more than 10 copies of the c-MAF gene.

In some embodiments, the amplification is in region at the 16q23 locus. In some embodiments, the amplification is in any part of the chromosomal region between about Chr. 16—about 79,392,959 bp to about 79,663,806 bp (from centromere to telomere). In some embodiments, the amplification is in the genomic region between about Chr. 16—about 79,392,959 bp to about 79,663,806 bp, but excluding DNA repeating elements. In some embodiments, amplification is measured using a probe specific for that region.

In a particular embodiment, the amplification or the copy number is determined by means of in situ hybridization or PCR.

Methods for determining whether the c-MAF gene or the chromosome region 16q22-q24 is amplified are widely known in the state of the art. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase-chain reaction (such as real time quantitative PCR). For any ISH method, the amplification or the copy number can be determined by counting the number of fluorescent points, colored points or points with silver in the chromosomes or in the nucleus.

The fluorescence in situ hybridization (FISH) is a cytogenetic technique which is used for detecting and locating the presence or absence of specific DNA sequences in chromosomes. FISH uses fluorescence probes which only bind to some parts of the chromosome with which they show a high degree of sequence similarity. In a typical FISH method, the DNA probe is labeled with a fluorescent molecule or a hapten, typically in the form of fluor-dUTP; digoxigenin-dUTP, biotin or hapten-dUTP which is incorporated in the DNA using enzymatic reactions, such as nick translation or PCR, The sample containing the genetic material (the chromosomes) is placed on glass slides and is denatured by a form amide treatment. The labeled probe is then hybridized with the sample containing the genetic material under suitable conditions which will be determined by the person skilled in the art. After the hybridization, the sample is viewed either directly (in the case of a probe labeled with fluorine) or indirectly (using fluorescently labeled antibodies to detect the hapten).

In the case of CISH, the probe is labeled with digoxigenin, biotin or fluorescein and is hybridized with the sample containing the genetic material in suitable conditions.

Any marking or labeling molecule which can bind to a DNA can be used to label the probes used in the fourth method of the invention, thus allowing the detection of nucleic acid molecules. Examples of labels for the labeling include, although not limited to, radioactive isotopes, enzyme, substrates, cofactors, ligands, chemiluminescence agents, fluorophores, haptens, enzymes and combinations thereof. Methods for labeling and guideline for selecting suitable labels for different purposes can be found, for example, in Sambrook et al. (Molecular Cloning: A Laboratory Manual, Cold Spring Harbor, N.Y., 1989) and Ausubel et al. (In Current Protocols in Molecular Biology, John Wiley and Sons, New York, 1998).

Once the existence of amplification is determined, either by directly determining the amplification of the c-MAF gene or by determining the amplification of the locus 16q22-q24, and after being compared with the amplification of said gene in the control sample, if amplification in the c-MAF gene is detected, it is indicative of the fact that the subject has a positive diagnosis for metastasis or a greater tendency to develop metastasis.

The determination of the amplification of the c-MAF gene needs to be correlated with values of a control sample or reference sample that correspond to the level of amplification of the c-MAF gene measured in a tumor tissue sample of a subject with lung cancer who has not suffered metastasis or that correspond to the median value of the amplification of the c-MAF gene measured in a tumor tissue collection in biopsy samples of subjects with lung cancer who have not suffered metastasis. Said reference sample is typically obtained by combining equal amounts of samples from a subject population. In general, the typical reference samples will be obtained from subjects who are clinically well documented and in whom the absence of metastasis is well characterized. The sample collection from which the reference level is derived will preferably be made up of subjects suffering the same type of cancer as the patient object of the study (e.g., NSCLC). Once this median value has been established, the level of amplification of c-MAF in tumor tissues of patients can be compared with this median value, and thus, if there is amplification, the subject has a positive diagnosis of metastasis or a greater tendency to develop metastasis.

In a preferred embodiment, the metastasis is bone metastasis. In a yet more preferred embodiment, the bone metastasis is osteolytic bone metastasis. As used herein, the expression "osteolytic bone metastasis" refers to a type of metastasis in which bone resorption (progressive loss of bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

Method of Prognosis of Metastasis in Lung Cancer Based on Detecting the Translocation of the c-MAF Gene In another aspect, the invention relates to an in vitro method for predicting the clinical outcome of a patient suffering from lung cancer, which comprises determining if the c-MAF gene is translocated in a sample of said subject wherein a translocation of the c-MAF gene is indicative of a poor clinical outcome.

In another aspect, the invention relates to an in vitro method for predicting the clinical outcome of a patient suffering lung cancer, which comprises determining if the c-MAF gene is translocated in a sample of said subject wherein a translocation of the c-MAF gene is indicative of a poor clinical outcome.

In some embodiments, the translocated gene is from the region at the 16q23 locus. In some embodiments, the translocated gene is from any part of the chromosomal region between about Chr. 16—about 79,392,959 bp to about 79,663,806 bp (from centromere to telomere). In some embodiments, the translocated gene is from the genomic region between about Chr. 16—about 79,392,959 bp to about 79,663,806 bp, but excluding DNA repeating elements. In some embodiments, the translocation is measured using a probe specific for that region.

In a particular embodiment, the translocation of the c-MAF gene can be determined by means of determining the translocation of a chromosome region containing said gene. In one embodiment, the translocation is the t(14,16) translocation. In another embodiment, the chromosome region that is translocated is from locus 16q22-q24. The locus 16q22-q24 is located in chromosome 16, in the long arm of said chromosome and in a range between band 22 and band 24. This region corresponds in the NCBI database with the contigs NT_010498.15 and NT_010542.15. In a preferred embodiment, the c-MAF gene translocates to chromosome 14 at the locus 14q32, resulting in the translocation t(14, 16)(q32,q23). This translocation places the MAF gene next to the strong enhancers in the IgH locus, which, in some cases, leads to overexpression of MAF. (Eyehene, A., Rocques, N., and Puoponnot, C., A new MAFia in cancer. 2008. Nature-Reviews: Cancer. 8:683-693.)

In a preferred embodiment, the translocation of the c-MAF gene can be determined by means of using a probe specific for said translocation. In some embodiments, the translocation is measured using a dual color probe. In some embodiments, the translocation is measured using a dual fusion probe. In some embodiments, the translocation is measured using a dual color, dual fusion probe. In some embodiments, the translocation is measured using two separate probes.

In another preferred embodiment, the translocation of the C-MAF gene is determined using the Vysis LSI IGH/MAF Dual Color dual fusion probe (http://www.abbottmolecular.com/us/products/analyte-specific-reagent/fish/vysis-lsi-igh-maf-dual-color-dual-fusion-probe.html; last accessed Nov. 5, 2012), which comprises a probe against 14q32 and 16q23. In another preferred embodiment, the translocation of the c-MAF gene is determined using a Kreatech diagnostics MAF/IGH gt(14;16) Fusion probe (http://www.kreatech.com/products/repeat-freetm-poseidontm-fish-probes/hematology/maf-igh-gt1416-fusion-probe.html; last accessed Nov. 5, 2012), an Abnova MAF FISH probe (http://www.abnova.com/products/products_detail.asp?Catalog_id=FA0375; last accessed Nov. 5, 2012), a Cancer Genetics Italia IGH/MAF Two Color, Two Fusion translocation probe (http://www.cancergeneticsitalia.com/dna-fish-probe/igh-maf/; last accessed Nov. 5, 2012), a Creative Bioarray IGH/MAF-t(14;16) (q32;q23) FISH probe (http://www.creative-bioarray.com/products.asp?cid=35&page=10; last accessed Nov. 5, 2012), a Arup Laboratories multiple myeloma panel by FISH (http://www.aruplab.com/files/technical-bulletins/multiple%20Myeloma%20%28MM%29%20by%20FISH.pdf; last accessed Nov. 5, 2012), an Agilent probe specific to 16q23 or 14q32 (http://www.genomics.agilent.com/ProductSearch.aspx?chr=16&start=79483700&end=7.9754340; last accessed Nov. 5, 2012; http://www.genomics.agilent.com/ProductSearch.aspx?Pageid=3000&ProductID=637; last accessed Nov. 5, 2012), a Dako probe specific to 16q23 or 14q32 (http://www.dako.com/us/ar42/psg42806000/baseproducts_surefish.htm?setCountry=true&purl=ar42/psg42806000/baseproducts_surefish.htm?undefined&submit=Accept%20country; last accessed Nov. 5, 2012), a Cytocell IGH/MAF Translocation, Dual Fusion Probe (http://www.zentech.be/uploads/docs/products_info/prenatalogy/cytocell%202012-2013%20catalogue%5B3%5D.pdf; last accessed Nov. 5, 2012), a Metasystems XL IGH/MAF Translocation Dual Fusion Probe (http://www.metasystems-international.com/index.php?option=com_joodb&view=article&joobase=5&id=12%3Ad-5029-100-og&Itemid=272; last accessed Nov. 5, 2012), a Zeiss FISH Probes XL, 100 µl, IGH/MAFB (https://www.micro-shop.zeiss.com/?s=440675675dedc6&l=en&p=uk&f=r&i=5000&o=&h=25&n=1U2d=000000-0528-231-uk; last accessed Nov. 5, 2012) or a Genycell Biotech IGH/MAF Dual Fusion Probe (http://www.google.com/url?sa=t&ret=j&q=&esrc=s&source=web&cd=1&ved=0CCQQFjAA&url=http%3A%2F%2Fwww.genycell.es%2Fimages%2Fproductos%2Fbrochures%2Flphmie6_86.ppt&ci=MhGYUOi3GKWH0QGlt4DoDw&usg=AFQjCNEqQMbT8vQGjJbi9riEf31VgoFTFQ&sig2=V5IS8juEMVHB18Mv2Xx_Ww; last accessed Nov. 5, 2012)

In some embodiments, the label on the probe is a fluorophore. In some embodiments, the fluorophore on the probe is orange. In some embodiments, the fluorophore on the probe is green. In some embodiments, the fluorophore on the probe is red. In some cases, the fluorophore on the probe is yellow. In some embodiments, one probe is labeled with a red fluorophore, and one with a green fluorophore. In some embodiments, one probe is labeled with a green fluorophore and one with an orange fluorophore. In some cases, the fluorophore on the probe is yellow. For instance, if the MAF-specific probe is labeled with a red fluorophore, and the IGH-specific probe is labeled with a green fluorophore, if white is seen it indicates that the signals overlap and translocation has occurred.

In some embodiments, the fluorophore is SpectrumOrange. In some embodiments, the fluorophore is SpectrumGreen. In some embodiments, the fluorophore is DAPI. In some embodiments, the fluorophore is PlatinumBright405. In some embodiments, the fluorophore is PlatinumBright415. In some embodiments, the fluorophore is PlatinumBright495. In some embodiments, the fluorophore is PlatinumBright505. In some embodiments, the fluorophore is PlatinumBright550. In some embodiments, the fluorophore is PlatinumBright547. In some embodiments, the fluorophore is PlatinumBright570. In some embodiments, the fluorophore is PlatinumBright590. In some embodiments, the fluorophore is PlatinumBright647. In some embodiments, the fluorophore is PlatinumBright495/

550. In some embodiments, the fluorophore is Platinum-Bright415/495/550. In some embodiments, the fluorophore is PAPI/PlatinumBright495/550. In some embodiments, the fluorophore is FITC. In some embodiments, the fluorophore is Texas Red. In some embodiments, the fluorophore is DEAC. In some embodiments, the fluorophore is R6G. In some embodiments, the fluorophore is Cy5. In some embodiments, the fluorophore is FITC, Texas Red and DAPI. In some embodiments, a DAPI counterstain is used to visualize the translocation, amplification or copy number alteration.

One embodiment of the invention comprises a method in which in a first step it is determined if the c-MAF gene is translocated in a sample of a subject. In a preferred embodiment, the sample is a tumor tissue sample.

In a particular embodiment, a method of the invention for the prognosis of the tendency to develop bone metastasis in a subject with lung cancer comprises determining the c-MAF gene copy number in a sample of said subject wherein the c-MAF gene is translocated and comparing said copy number with the copy number of a control or reference sample, wherein if the c-MAF copy number is greater with respect to the c-MAF copy number of a control sample, then the subject has a greater tendency to develop bone metastasis. In a preferred embodiment, the bone metastasis is very early bone metastasis. In a preferred embodiment, the bone metastasis is osteolytic metastasis.

"Average level" as used herein relates to a single value of c-MAF expression level (as a mean, mode, or median) that summarizes or represents the general significance of a set of unequal values. In a preferred embodiment the average level corresponds to the average of expression levels obtained from a representative cohort of lung cancer tumors. The patient cohort is defined by age that is representative of the individual patient that one is attempting to evaluate.

"Standard deviation" as used herein relates to a measure of the dispersion of a collection of numbers. For example, the standard deviation for the average normal level of c-MAF is the dispersion of a collection of the c-MAF levels found in lung tumor samples The more spread apart the data, the higher the deviation. Standard deviation can be obtained by extracting the square root of the mean of squared deviations of observed values from their mean in a frequency distribution.

Once the c-MAF gene expression level in a sample from a subject with lung cancer, has been measured and compared with the average level, if the expression level of said gene is above the average plus one standard deviation with respect to the average level, then it can be concluded that said subject has a greater tendency to develop early bone metastasis.

Methods for determining whether the c-MAF gene or the chromosome region 16q22-q24 is translocated are widely known in the state of the art and include those described previously for the amplification of c-MAF. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification, the copy number, or the translocation can be determined by counting the number of fluorescent points, colored points or points with silver in the chromosomes or in the nucleus. In other embodiments, the detection of copy number alterations and translocations can be detected through the use of whole genome sequencing, exome sequencing or by the use of any PCR derived technology. For instance, PCR can be performed on samples of genomic DNA to detect translocation. In one embodiment, quantitative PCR is used. In one embodiment, PCR is performed with a primer specific to the c-MAF gene and a primer specific to the IGH promoter region; if a product is produced, translocation has occurred.

In some embodiments, the amplification and copy number of the c-MAF gene are determined after translocation of the c-MAF gene is determined. In some embodiments, the probe is used to determine if the cell is polyploid for the c-MAF gene. In some embodiments, a determination of polyploidy is made by determining if there are more than 2 signals from the gene of interest. In some embodiments, polyploidy is determined by measuring the signal from the probe specific for the gene of interest and comparing it with a centromeric probe or other probe.

Method of Prognosis of Clinical Outcome in Lung Cancer Based on Defecting the Amplification or Translocation of the c-MAF Gene In another aspect, the invention relates to an in vitro method (hereinafter seventh method of the invention) for predicting the clinical outcome of a patient suffering lung cancer, which comprises determining if the c-MAF gene is amplified or translocated in a sample of said subject relative to a reference gene copy number wherein an amplification of the c-MAF gene with respect to said reference gene copy number is indicative of a poor clinical outcome.

The seventh method of the invention comprises in a first step, determining if the c-MAF gene is amplified in a sample of a subject. The determination of the amplification of the c-MAF is carried out essentially as described in the fifth method of the invention. In a preferred embodiment the sample is a tumor tissue sample. In a preferred embodiment, the amplification of the c-MAF gene is determined by means of determining the amplification of the locus 16q23 or 16q22-q24. In another preferred embodiment, the amplification of the c-MAF gene is determined by means of using a c-MAF gene-specific probe.

In a second step, the seventh method of the invention comprises comparing said copy number with the copy number of a control or reference sample, wherein if the c-MAF copy number is greater with respect to the c-MAF copy number of a control sample, then this is indicative of a poor clinical outcome.

In a preferred embodiment the c-MAF gene is amplified with respect to a reference gene copy number when the c-MAF gene copy number is higher than the copy number that a reference sample or control sample has. In one example, the c-MAF gene is said to be "amplified" if the genomic copy number of the c-MAF gene is increased by at least 2- (i.e., 6 copies), 3- (i.e., 8copies), 4-, 5-, 6-, 7-, 8-, 9-, 10-, 15-, 20-, 25-, 30-, 35-, 40-, 45-, or 50-fold in a test sample relative to a control sample. In another example, a c-MAF gene is said to be "amplified" if the genomic copy number of the c-MAF gene per cell is at least 3, 4, 5, 6, 7, 8, 9, 10, 11, 12, 13, 14, 15, 16, 17, 18, 19, 20, 21, 22, 23, 24, 25, 26, 27, 28, 29, 30, and the like.

In another embodiment, the reference gene copy number is the gene copy number in a sample of lung cancer, from a subject who has not suffered bone metastasis.

In another embodiment, the amplification is determined by means of in situ hybridization or PCR.

Therapeutic Methods of the Invention
Treating bone metastasis using c-MAF inhibitory agents.

A c-MAF gene expression inhibitory agent or an inhibitory agent of the protein encoded by said gene can be used in the treatment and/or the prevention of lung cancer metastasis.

In another aspect, the invention relates to the use of a c-MAF inhibitory agent for the manufacture of a medicament for the treatment or prevention of bone metastasis lung cancer.

In another aspect, the invention relates to a method for the treatment or prevention of the bone metastasis from lung cancer, in a subject in need thereof comprising the administration to said subject of a c-MAF inhibitory agent.

In another aspect, the invention relates to a method for preventing or reducing the risk of bone metastasis in a subject suffering from lung cancer, said method comprising administering to said subject an agent that prevents or reduces bone metastasis, wherein said agent is administered in accordance with a treatment regimen determined from quantifying the expression level of c-MAF in said subject.

Therefore, in another aspect, the invention relates to the use of a c-MAF gene expression inhibitory agent or an inhibitory agent of the protein encoded by said gene (hereinafter, inhibitory agent of the invention) in the preparation of a medicinal product for treating and/or preventing lung cancer metastasis. Alternatively, the invention relates to a c-MAF gene expression inhibitory agent or an inhibitory agent of the protein encoded by said gene for use in the treatment and/or the prevention of lung cancer metastasis. Alternatively, the invention relates to a method for treating the lung cancer metastasis in a subject which comprises administering a c-MAF inhibitor to said subject.

As used herein, a "c-MAF inhibitory agent" refers to any molecule capable of completely or partially inhibiting the c-MAF gene expression, both by preventing the expression product of said gene from being produced (interrupting the c-MAF gene transcription and/or blocking the translation of the mRNA coming from the c-MAF gene expression) and by directly inhibiting the c-MAF protein activity. C-MAF gene expression inhibitors can be identified using methods based on the capacity of the so-called inhibitor to block the capacity of c-MAF to promote the in vitro cell proliferation, such as shown in the international patent application WO2005/046731 (hereby incorporated by reference in its entirety), based on the capacity of the so-called inhibitor to block the transcription capacity of a reporter gene under the control of the cyclin D2 promoter or of a promoter containing the c-MAF response region (MARE or c-MAF responsive element) in cells which express c-MAF such as described in WO2008098351 (hereby incorporated by reference in its entirety) or based on the capacity of the so-called inhibitor to block the expression of a reporter gene under the control of the IL-4 promoter in response to the stimulation with PMA/ionomycin in cells which express NFATc2 and c-MAF such as described in US2009048117A (hereby incorporated by reference in its entirety).

By way of non-limiting illustration, c-MAF inhibitory agents suitable for use in the present invention include antisense oligonucleotides, interference RNAs (siRNAs), catalytic RNAs or specific ribozymes and inhibitory antibodies.

Antisense Oligonucleotides

An additional aspect of the invention relates to the use of isolated "antisense" nucleic acids to inhibit expression, for example, for inhibiting transcription and/or translation of a nucleic acid which encodes c-MAF the activity of which is to be inhibited. The antisense nucleic acids can be bound to the target potential of the drug by means of conventional base complementarity or, for example, in the case of biding to Double stranded DNA through specific interaction in the large groove of the double helix. Generally, these methods refer to a range of techniques generally used in the art and they include any method which is based on the specific binding to oligonucleotide sequences.

An antisense construct of the present invention can be administered, for example, as an expression plasmid which, when is transcribed in cell, produces RNA complementary to at least one unique part of the cellular mRNA encoding c-MAF. Alternatively, the antisense construct is a oligonucleotide probe generated ex vivo which, when introduced into the cell, produces inhibition of gene expression hybridizing with the mRNA and/or gene sequences of a target nucleic acid. Such oligonucleotide probes are preferably modified oligonucleotides which are resistant to endogenous nucleases, for example, exonucleases and/or endonucleases and are therefore stable in vivo. Examples of nucleic acids molecules for use thereof as an antisense oligonucleotides are DNA analogs of phosphoramidate, phosphothionate and methylphosphonate (sec also U.S. Pat. Nos. 5,176,996; 5,264,564; and 5,256,775) (hereby incorporated by reference in their entireties). Additionally, the general approximations for constructing oligomers useful in the antisense therapy have been reviewed, for example, in Van der Krol et al., BioTechniques 6: 958-976, 1988; and Stein et al. Cancer Res 48:2659-2668, 1988.

With respect to the antisense oligonucleotide, the oligodeoxyribonucleotide regions derived from the starting site of the translation, for example, between −10 and +10 of the target gene are preferred. The antisense approximations involve the oligonucleotide design (either DNA or RNA) that are complementary to the mRNA encoding the target polypeptide. The antisense oligonucleotide will be bound to the transcribed mRNA and translation will be prevented.

The oligonucleotides which are complementary to the 5' end of the mRNA, for example the non translated 5' sequence up to and including the start codon AUG must function in the most efficient manner to inhibit translation. Nevertheless, it has been shown that the sequences complementary to the non translated 3' sequences of the mRNA are also efficient for inhibiting mRNA translation (Wagner, Nature 372:333, 1994). Therefore, complementary oligonucleotides could be used at the non translated 5' or 3' regions, non coding regions of a gene in an antisense approximation to inhibit the translation of that mRNA. The oligonucleotides complementary to the non translated 5' region of the mRNA must include the complement of the start codon AUG. The oligonucleotides complementary to the coding region of the mRNA are less efficient translation inhibitors but they could also be used according to the invention. If they are designed to hybridize with the 5' region, 3' region or the coding region of the mRNA, the antisense nucleic acids must have at least six nucleotides long and preferably have less than approximately 100 and more preferably less than approximately 50, 25, 17 or 10 nucleotides long.

Preferably, in vitro studies are performed first to quantify the capacity of the antisense oligonucleotides for inhibiting gene expression. Preferably, these studies use controls which distinguish between antisense gene inhibition and nonspecific biological effects of the oligonucleotides. Also preferably these studies compared the levels of target RNA or protein with that of an internal control of RNA or protein. The results obtained using the antisense oligonucleotides can be compared with those obtained using a control oligonucleotide. Preferably the control oligonucleotide is approximately of the same length as the oligonucleotide to be assayed and that the oligonucleotide sequence does not differ from the antisense sequence more than it is deemed necessary to prevent the specific hybridization to the target sequence.

The antisense oligonucleotide can be a single or double stranded DNA or RNA or chimeric mixtures or derivatives or modified versions thereof. The oligonucleotide can be modified in the base group, the sugar group or the phosphate backbone, for example, to improve the stability of the molecule, its hybridization capacity etc. The oligonucleotide may include other bound groups, such as peptides (for example, for directing them to the receptors of the host cells) or agents for facilitating transport through the cell membrane (see, for example, Letsinger et al., Proc. Natl. Acad. Sci. U.S.A. 86:6553-6556, 1989, Lemaitre et al., Proc. Natl. Acad. Sci. 84:648-652, 1987; PCT Publication No. WO 88/09810) or the blood-brain barrier (see, for example, PCT Publication No. WO 89/10134), intercalating agents, (see, for example, Zon, Pharm. Res. 5:539-549, 1988). For this purpose, the oligonucleotide can be conjugated to another molecule, for example, a peptide, a transporting agent, hybridization triggered cleaving agent, etc.

The antisense oligonucleotides may comprise at least one group of modified base. The antisense oligonucleotide may also comprise at least a modified sugar group selected from the group including but not limited to arabinose, 2-fluoro-arabinose, xylulose, and hexose. The antisense oligonucleotide may also contain a backbone similar to a neutral peptide. Such molecules are known as peptide nucleic acid (PNA) oligomers and are described, for example, in Perry-O'Keefe et al., Proc. Natl. Acad. Sci. U.S.A. 93:14670, 1996, and in Eglom et al., Nature 365:566, 1993.

In yet another embodiment, the antisense oligonucleotide comprises at least one modified phosphate backbone. In yet another embodiment, the antisense oligonucleotide is an alpha-anomeric oligonucleotide.

While antisense oligonucleotides complementary to the coding region of the target mRNA sequence can be used, those complementary to the transcribed non translated region can also be used.

In some cases, it may be difficult to reach the sufficient intracellular concentrations of the antisense to suppress the endogenous mRNA translation. Therefore, a preferred approximation uses a recombinant DNA construct in which the antisense oligonucleotide is placed under the control of a strong pol III or pol II promoter.

Alternatively, the target gene expression can be reduced by directing deoxyribonucleotide sequences complementary to the gene regulating region (i.e., the promoter and/or enhancers) to form triple helix structures preventing gene transcription in the target cells in the body (see in general, Helene, Anticancer Drug Des. 6(6): 569-84, 1991). In certain embodiments, the antisense oligonucleotides are antisense morpholines.

siRNA

Small interfering RNA or siRNA are agents which are capable of inhibiting the expression of a target gene by means of RNA interference. A siRNA can be chemically synthesized, can be obtained by means of in vitro transcription or can be synthesized in vivo in the target cell. Typically, the siRNA consist of a double stranded RNA between 15 and 40 nucleotide long and may contain a 3' and/or 5' protruding region of 1 to 6 nucleotides. The length of the protruding region is independent of the total length of the siRNA molecule. The siRNA act by means of degrading or silencing the target messenger after transcription.

The siRNA of the invention are substantially homologous to the mRNA of the c-MAF encoding gene or to the gene sequence which encodes said protein. "Substantially homologous" is understood as having a sequence which is sufficiently complementary or similar to the target mRNA such that the siRNA is capable of degrading the latter through RNA interference. The siRNA suitable for causing said interference include siRNA formed by RNA, as well as siRNA containing different chemical modifications such as
  siRNA in which the bonds between the nucleotides are different than those appear in nature, such as phosphorothionate bonds.
  Conjugates of the RNA strand with a functional reagent, such as a fluorophore.
  Modifications of the ends of the RNA strands, particularly of the 3' end by means of the modification with different hydroxyl functional groups in 2' position.
  Nucleotides with modified sugars such as O-alkylated residues on 2' position like 2'-O-Nucleotides or 2'-O-fluororibose.
  Nucleotides with modified bases such as halogenated bases (for example 5-bromouracil and 5-iodouracil), alkylated bases (for example 7-methylguanosine).

The siRNA can be used as is, i.e., in the form of a double stranded RNA with the aforementioned characteristics. Alternatively, the use of vectors containing the sense and antisense strand sequence of the siRNA is possible under the control of suitable promoters for the expression thereof in the cell of interest.

Vectors suitable for expressing siRNA are those in which the two DNA regions encoding the two strands of siRNA are arranged in tandem in one and the same DNA strand separated by a spacer region which, upon transcription, forms a loop and wherein a single promoter directs the transcription of the DNA molecule giving rise to shRNA.

Alternatively, the use of vectors in which each of the strands forming the siRNA is formed from the transcription of a different transcriptional unit is possible. These vectors are in turn divided into divergent and convergent transcription vectors. In divergent transcription vectors, the transcriptional units encoding each of the DNA strands forming the siRNA are located in tandem in a vector such that the transcription of each DNA strand depends on its own promoter which may be the same or different (Wang, J. et al., 2003, Proc. Natl. Acad. Sci. USA., 100:5103-5106 and Lee, N. S., et al., 2002, Nat. Biotechnol., 20:506-505). In convergent transcription vectors, the DNA regions giving rise to the siRNA form the sense and antisense strands of a DNA region which are flanked by two reverse promoters. After the transcription of the sense and antisense RNA strands, the latter will form the hybrid for forming a functional siRNA. Vectors with reverse promoter systems in which 2 U6 promoters (Tran, N. et al., 2003, BMC Biotechnol., 3:21), a mouse U6 promoter and a human H1 promoter (Zheng, L., et al., 2004, Proc. Natl. Acad. Sci. USA., 135-140 and WO 2005026322) and a human U6 promoter and a mouse H1 promoter (Kaykas, A. and Moon, R., 2004, BMC Cell Biol., 5:16) are used have been described.

Promoters suitable for use thereof in the expression of siRNA from convergent or divergent expression vectors include any promoter, or pair of promoters compatible with the cells in which the siRNA is to be expressed. Thus, promoters suitable for the present invention include but are not necessarily limited to constitutive promoters such as those derived from the genomes of eukaryotic viruses such as the polyoma virus, adenovirus, SV40, CMV, avian sarcoma virus, hepatitis B virus, the metallothionein gene promoter, the thymidine kinase gene promoter of the herpes simplex virus, retrovirus LTR regions, the immunoglobulin gene promoter, the actin gene promoter, the EF-1alpha gene promoter as well as inducible promoters in which the protein expression depends on the addition of a molecule or an exogenous signal such as the tetracycline system, the NFkappaB/UV light system, the Cre/Lox system and the heat shock gene promoter, the regulatable RNA polymerase II promoters described in WO/2006/135436 as well as specific tissue promoters (for example, the PSA promoter described in WO2006012221). In a preferred embodiment, the promoters are RNA polymerase III promoters which act constitutively. The RNA polymerase III promoters are found in a limited number of genes such as 5S RNA, tRNA, 7SL RNA and U6 snRNA. Unlike other RNA polymerase III promoters, type III prompters do not require any intragenic sequence but rather need sequences in 5' direction comprising a TATA box in positions −34 and −24, a proximal sequence element or DSE between −66 and −47 and, in some cases, a distal sequence element or DSE between positions −265 and −149. In a preferred embodiment, the type III RNA polymerase III promoters are the human or murine H1 and U6 gene promoters. In a yet more preferred embodiment, the promoters are 2 human or murine U6 promoters, a mouse U6 promoter and a human H1 promoter or a human U6 promoter and a mouse H1 promoter.

The siRNA can be generated intracellularly from the so called shRNA (short hairpin RNA) characterized in that the antiparallel strands forming the siRNA are connected by a loop or hairpin region. The shRNAs can be encoded by plasmids or viruses, particularly retroviruses, and are under the control of a promoter. Promoters suitable for expressing shRNA are those indicated in the paragraph above for expressing siRNA.

Vectors suitable for expressing siRNA and shRNA include prokaryotic expression vectors such as pUC18, pUC19, Bluescript and the derivatives thereof, mp18, mp19, pBR322, pMB9, ColE1, pCR1, RP4, phages and shuttle vectors such as pSA3 and pAT28, yeast expression vectors such as 2-micron plasmid type vectors, integration plasmids, YEP vectors, centromeric plasmids and the like, insect cell expression vectors such as pAC series vectors and pVL series vectors, plant expression vectors such as pIBI, pEarleyGate, pAVA, pCAMBIA, pGSA, pGWB, pMDC, pMY, pORE series vectors and the like and viral vector-based (adenovirus, viruses associated with adenoviruses as well as retroviruses and particularly lentiviruses) higher eukaryotic cell expression vectors or non-viral vectors such as pcDNA3, pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1. In a preferred embodiment, the vectors are lentiviral vectors.

The siRNA and shRNA of the invention can be obtained using a series of techniques known by the person skilled in the art. The region of the nucleotide sequence taken as a basis for designing the siRNA is not limiting and it may contain a region of the coding sequence (between the start codon and the end codon) or it may alternatively contain sequences of the non-translated 5' or 3' region preferably between 25 and 50 nucleotides long and in any position in 3' direction position with respect to the start codon. One way of designing an siRNA involves the identification of the AA(N19)TT motifs wherein N can be any nucleotide in the c-MAF gene sequence, and the selection of those having a high G/C content. If said motif is not found, it is possible to identify the NA(N21) motif wherein N can be any nucleotide.

c-MAF specific siRNAs include the siRNA described in WO2005046731 (hereby incorporated by reference in its entirety), one of the strands of which is ACGG-CUCGAGCAGCGACAA (SEQ ID NO: 6). Other c-MAF specific siRNA sequences include but are not limited to CUUACCAGUGUGUUCACAA (SEQ ID NO: 7), UGGAAGACUACUACUGGAUG (SEQ ID NO: 8), AUUUGCAGUCAUGGAGAACC (SEQ ID NO: 9), CAAGGAGAAAUAGGAGAAGU (SEQ ID NO: 10), ACAAGGAGAAAUACGAGAAG (SEQ ID NO: 11) and ACCUGGAAGAGUACUACUGG (SEQ ID NO: 12).

DNA Enzymes

On the other hand, the invention also contemplates the use of DNA enzymes to inhibit the expression of the c-MAF gene of the invention. DNA enzymes incorporate some of the mechanistic features of both antisense and ribozyme technologies. DNA enzymes are designed such that they recognize a particular target nucleic acid sequence similar to the antisense oligonucleotide, nevertheless like the ribozyme they are catalytic and specifically cleave the target nucleic acid.

Ribozymes

Ribozyme molecules designed for catalytically cleaving transcription products of a target mRNA to prevent the translation of the mRNA which encodes c-MAF the activity of which is to be inhibited, can also be used. Ribozymes are enzymatic RNA molecules capable of catalysing specific RNA cleaving. (For a review, see, Rossi, Current Biology 4:469-471, 1994). The mechanism of ribozyme action involves a Specific hybridization of a ribozyme molecule sequence to a complementary target RNA followed by an endonucleolytic cleavage event. The composition of the ribozyme molecules preferably includes one or more sequences complementary to the target mRNA and the well known sequence responsible for cleaving the mRNA or a functionally equivalent sequence (see, for example, U.S. Pat. No. 5,093,246).

The ribozymes used in the present invention include hammer-head ribozymes, endoribonuclease RNA (hereinafter "Cech type ribozymes") (Zaug et. al., Science 224:574-578, 1984.

The ribozymes can be formed by modified oligonucleotides (for example to improve the stability, targeting, etc.) and they should be distributed to cells expressing the target gene in vivo. A preferred distribution method involves using a DNA construct which "encodes" the ribozyme under the control of a strong constitutive pol III or pol II promoter such that the transfected cells will produce sufficient amounts of the ribozyme to destroy the endogenous target messengers and to inhibit translation. Since the ribozymes are catalytic, unlike other antisense molecules, a low intracellular concentration is required for its efficiency.

Inhibitory Antibodies

In the context of the present invention, "inhibitory antibody" is understood as any antibody capable of binding specifically to the c-MAF protein and inhibiting one or more of the functions of said protein, preferably those related to transcription. The antibodies can be prepared using any of the methods which are known by the person skilled in the art, some of which have been mentioned above. Thus, the polyclonal antibodies are prepared by means of immunizing an animal with the protein to be inhibited. The monoclonal antibodies are prepared using the method described by Kohler, Milstein et al. (Nature, 1975, 256: 495). In the context of the present invention, suitable antibodies include intact antibodies comprising a variable antigen binding region and a constant region, "Fab", "F(ab')2" and "Fab'", Fv, scFv fragments, diabodies, bispecific antibodies, alphabodies, cyclopeptides and stapled peptides. Once antibodies with c-MAF protein binding capacity are identified, those capable of inhibiting the activity of this protein will be selected using an inhibitory agent identification assay.

Inhibitory Peptides

As used herein, the term "inhibitory peptide" refers to those peptides capable of binding to the c-MAF protein and inhibiting its activity as has been explained above, i.e., preventing the c-MAF from being able to activate gene transcription.

Negative c-MAF Dominants

Since the proteins from the maf family are capable of homodimerizing and heterodimerizing with other members of the AP-1 family such as Fos and Jun, one way of inhibiting c-MAF activity is by means of using negative dominants capable of dimerizing with c-MAF but lacking the capacity for activating transcription. Thus, the negative c-MAF dominants can be any of the small maf proteins existing in the cell and lacking two-thirds of the amino terminal end containing the transactivation domain (for example, mafK, mafF, mafg and pi 8) (Fujiwara et al (1993) Oncogene 8, 2371-2380, Igarashi et al. (1995) J. Biol. Chem. 270, 7615-7624; Andrews et al. (1993) Proc. Natl. Acad. Sci. USA 90, 11488-11492, Kataoka et al. (1995) Mol. Cell. Biol. 15, 2180-2190) (Kataoka et al. (1996) Oncogene 12, 53-62).

Alternatively, the negative c-MAF dominants include c-MAF variants which maintain the capacity for dimerizing with other proteins but lack the capacity for activating transcription. These variants are, for example, those lacking the c-MAF transactivation domain located at the N-terminal end of the protein. Thus, negative c-MAF dominant variants include in an illustrative manner the variants in which at least amino acids 1 to 122, at least amino acids 1-187 or at least amino acids 1 to 257 (by considering the numbering of human c-MAF as described in U.S. Pat. No. 6,274,338, hereby incorporated by reference in its entirety) have been removed.

The invention contemplates the use of both the negative c-MAF dominant variants and of polynucleotides encoding c-MAF under the operative control of a promoter suitable for expression in target cell. The promoters that can be used for regulating the polynucleotide transcription of the invention can be constitutive promoters, i.e., promoters directing the transcription at a basal level, or inducible promoters in which the transcriptional activity requires an external signal. Constitutive promoters suitable for regulating transcription are, among others, the CMV promoter, the SV40 promoter, the DHFR promoter, the mouse mammary tumor virus (MMTV) promoter, the 1a elongation factor (EF1a) promoter, the albumin-promoter, the ApoA1 promoter, the keratin promoter, the CD3 promoter, the immunoglobulin heavy or light chain promoter, the neurofilament promoter, the neuron specific enolase promoter, the L7 promoter, the CD2 promoter, the myosin light chain kinase promoter, the HOX gene promoter, the thymidine kinase promoter, the RNA polymerase II promoter, the MyoD gene promoter, the phosphoglyceratekinase (PGK) gene promoter, the low density lipoprotein (LDL) promoter, the actin gene promoter. In a preferred embodiment, the promoter regulating the expression of the transactivator is the PGK gene promoter. In a preferred embodiment, the promoter regulating the poly-nucleotide transcription of the invention is the RNA polymerase promoter of the T7 phage.

Preferably, the inducible promoters that can be used in the context of the present invention are those responding to an inducer agent showing zero or negligible basal expression in the absence of an inducer agent and are capable of promoting the activation of gene located in the 3' position. Depending on the type of inducer agent, the inducible promoters are classified as Tet on/off promoters (Gossen, M. and H. Bujard (1992) Proc. Natl. Acad. Sci. USA, 89:5547-5551: Gossen, M. et al., 1995, Science 268:1766-1769; Rossi, F. M. V. and H. M. Blau, 1998, Curr. Opin. Biotechnol. 9:451-456); Pip on/off promoters (U.S. Pat. No. 6,287,813); antiprogestin-dependent promoters (US 2004132086), ecdysone-dependent promoters (Christopherson et al., 1992, Proc. Natl. Acad. Sci. USA, 89:6314-6318; No et al., 1996; Proc. Natl. Acad. Sci. USA, 93:3346-3351, Suhr et al., 1998, Proc. Natl. Acad. Sci. USA, 95:7999-8004 and WO9738117), a metallothionein-dependent promoter (WO8604920) and rapamycin-dependent promoters (Rivera et al., 1996, Nat. Med. 2:1028-32).

Vectors suitable for expressing the polynucleotide encoding the negative c-MAF dominant variant include vectors derived from prokaryotic expression; vectors such, as pUC18, pUC19, Bluescript and derivatives thereof, mp18, mp19, pBR322, pMB9, ColE1, pCR1, RP4, phages and shuttle vectors such as pSA3 and pAT28, yeast expression vectors such as 2-micron type plasmid vectors, integration plasmids, YEP vectors centromeric plasmids and the like, insect cell expression vectors such as pAC series vectors and pVL series vectors, plant expression vectors such as pIBI, pEarleyGate, pAVA, pCAMBIA, pGSA, pGWB, pMDC, pMY, pORE series vectors and the like and viral vector-based (adenoviruses, viruses associated with adenoviruses as well as retroviruses and particularly lentiviruses) higher eukaryotic cell expression vectors OR non-viral vectors such as pSilencer 4.1-CMV (Ambion), pcDNA3, pcDNA3.1/hyg pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10; pBPV-1, pML2d and pTDTI.

Other Inhibitory Compounds of the c-MAF Protein Activity

Other c-MAF inhibitory compounds suitable for use in the present invention include:

TABLE 1 small molecules with c-MAF inhibiting capacity

I Endiandric acid H derivatives such as those described in WO2004014888 corresponding to the general formula TABLE 1-continued small molecules with c-MAF inhibiting capacity wherein
$R_1$ and $R_2$ are, independently of one another,
1.0 H or
2.0 a $O-C_1-C_6$-alkyl, $-O-C_2-C_6$-alkenyl, $-O-C_2-C_6$-alkynyl or $-O-C_6-C_{10}$-aryl group, in which alkyl, alkenyl and alkynyl are straight-chain or branched, and in which the alkyl, alkenyl and alkynyl groups are mono- or disubstituted with:
2.1 —OH,
2.2 =O,
2.3 —O—$C_1$-C6-alkyl, in which alkyl is straight-chain or branched,
2.4 —O—$C_2$-$C_6$-alkenyl, in which alkenyl is straight-chain or branched,
2.5 $C_6$-$C_{10}$-aryl,
2.6 —NH—$C_1$-$C_6$-alkyl, in which alkyl is straight-chain or branched,
2.7 —NH—$C_2$-$C_6$-alkenyl, in which alkenyl is straight-chain or branched,
2.8 —$NH_2$ or
2.9 halogen,
and in which the aryl group, is optionally mono- or disubstituted with the substituent 2.1 or 2.3 to 2.9,
in which the substituents 2.3, 2.4, 2.6 and 2.7 may be further substituted with —CN, -amide or -oxime functions, and 2.5 may be further substituted with —CN or amide functions, or $R_1$ and $R_2$ together form a ring, wherein $R_1$ and $R_2$ mean a
—O—[($C_1$-$C_6$)-alkylene]-O— group,
$R_3$ is
1.0 H or
2.0 a $-O-C_1-C_6$-alkyl, $-O-C_2-C_6$-alkenyl, $-O-C_2-C_6$-alkynyl or $-O-C_6-C_{10}$-aryl group, in which alkyl, alkenyl and alkynyl are straight-chain or branched, and in which the alkyl, alkenyl and alkynyl groups are mono- or disubstituted with:
2.1 —OH,
2.2 =O,
2.3 —O—$C_1$-$C_6$-alkyl, in which alkyl is straight-chain or blanched,
2.4 —O—$C_2$-$C_6$-alkenyl, in which alkenyl is straight-chain or branched,
2.5 —$C_6$-$C_{10}$-aryl,
2.6 —NH—$C_1$-$C_6$-alkyl, in which alkyl is straight-chain or branched,
2.7 —NH—$C_2$-$C_6$-alkenyl, in which alkenyl is straight-chain or branched,
2.8 —$NH_2$ or
2.9 halogen,
and in which the aryl group, is optionally mono- or disubstituted with the substituent 2.1 or 2.3 to 2.9,
in which the substituents 2.3, 2.4, 2.6 and 2.7 may be further substituted with —CN, -amide or -oxime functions, and 2.5 may be further substituted with —CN or amide functions
$R_4$ is $CO_2R_3$, $CO_2NHR_3$, CHO, $CH_2OR_3$, $CH_2OSi(R_3)_3$, $CH_2Br$, $CH_2CN$, in which $R_3$ is as defined above,
and, in particular, the compounds

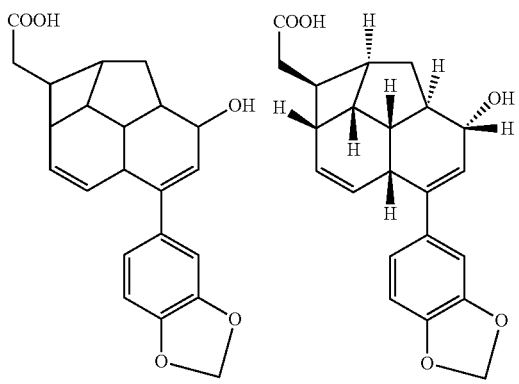

II 8-hydroxyquinoline derivatives such as those described in WO2009146546 of general formula

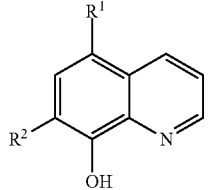

wherein
$R_1$ is selected from the group consisting of $NO_2$, $NH_2$, $NH(C_1$-$C_6$-alkyl) and $N(C_1$-$C_6$-alkyl)($C_1$-$C_6$-alkyl);
$R_2$ is selected from H, halogen, $C_1$-$C_6$ alkyl, and fluoro-substituted $C_1$-$C_6$ alkyl, or
$R_1$ is Cl and $R_2$ is Br or H,
and, preferably, the compounds

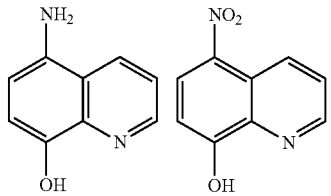

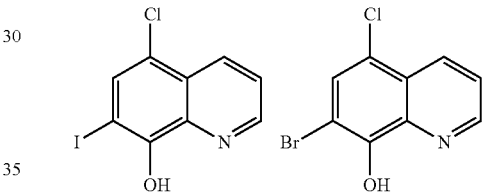

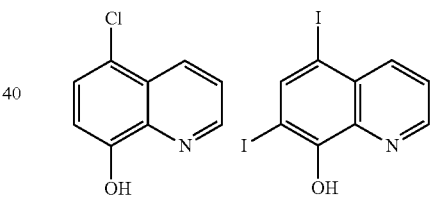

III Clioquinol (5-chloro-7-iodoquinolin-8-ol) as described in WO09049410
IV Compounds such as those described in WO08098351 of general formula

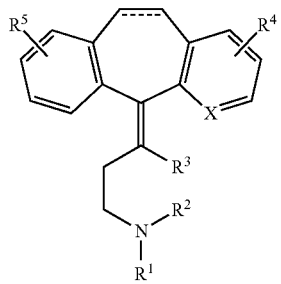

wherein
==-:-:-: is a single or double bond,
$R^1$ is selected from the group consisting of H, $C_1$-$C_4$ alkyl, C(O)O $C_1$-$C_4$ alkyl, C(O) $C_1$-$C_4$ alkyl and C(O)NH $C_1$-$C_4$ alkyl;
$R^2$ is selected from H and $C_1$-$C_4$ alkyl;
$R^3$ is selected from H and $C_1$-$C_4$ alkyl;
or $R^2$ and $R^3$ are bound together along with the carbon and nitrogen atoms to which they are bound to form a piperidine ring,

TABLE 1-continued small molecules with c-MAF inhibiting capacity $R^4$ and $R^5$ are independently selected from H, halogen, hydroxy, $C_1$-$C_4$ alkyl, fluoro-substituted $C_1$-$C_4$ alkyl and $C_1$-$C_4$ alkoxy; and X is selected from C and N,
and preferred compounds such as
Cyproheptadine (4-(5H-dibenzo-[a,d]cyclohepten-5-ylidene)-1-methylpiperidine hydrochloride),
Amitriptyline (3-(10,11-dihydro-5H-dibenzo[[a,d]]cycloheptene-5-ylidene)-N,N-dimethyl-1-propanamine),
Loratadine (Ethyl 4-(8-chloro-5,6-dihydro-11H-benzo[5,6]cyclohepta[1,2-b]pyridin-11-ylidene)-1-piperidinecarboxylate,
Cyclobenzrapine (3-(5H-dibenzo[a,d]cyclohepten-5-ylidene)-N,N-dimethyl-1-propanamine).
V Nivalenol (12,13-epoxy-3,4,7,15-tetrahydroxytrichothec-9-en-8-one) as described in WO0359249

Other c-MAF inhibitors are described in the patent application WO2005063252, such as shown in the following table (Table 2).

TABLE 2 c-MAF inhibitors

| Antagonist | Reference for cdk2 inhibitory activity |
|---|---|
| Purine Analogs | |
| Purvalanols such as 2-(1R-Isopropyl-2-hydroxyethylamino)-6-(3-chloroanilino)-9-isopropylpurine having a molecular formula $C_{19}H_{25}ClN_6O$ available from Sigma-Aldrich under the trade name Purvalanol A (#P4484, Sigma-Aldrich, St. Louis, MO), Purvalanol B, aminopurvalanol, compound 52 (where isopropyl of purvalanol A is replaced with H) | Gray, N. S. et al., Science, 281, 533-538 (1998); Chang, Y. T. et al., Chem. Biol., 6, 361-375 (1999). |
| 2-(Hydroxyethylamino)-6-benzylamino-9-methylpurine having a molecular formula $C_{15}H_{18}N_6O$ available from Sigma-Aldrich under the trade name Olomoucine (#O0886), 2-(2'-Hydroxyethylamino)-6-benzylamino-9-isopropylpurine having a molecular formula $C_{17}H_{22}N_6O$ available from Sigma-Aldrich under the trade name $N^9$-isopropylolomoucine (#I0763); CVT-313 | Vesely, J., et al., (1994) Eur, J. Biochem., 224, 771-86, 11; Brooks, E. E., et al., (1997) J. Biol. Chem., 272, 29207-11 |
| 6-(Benzylamino)-2(R)-[[1-(hydroxymethyl)propyl]amino]-9-isopropylpurine 2-(R)-[[9-(1-methylethyl)-6-[(phenylmethyl)amino]-9H-purin-2-yl]amino]-1-butanol having a molecular formula of $C_{19}H_{26}N_6O$ available from Sigma-Aldrich under the trade name Roscovitine (#R7772), methoxyroscovitine | Wang, D. et al., J. Virol., 75, 7266-7279 (2001); McClue, S., et al., Int. J. Cancer, 102, 463-468 (2002); Meijer, L., et al., (1997) Eur. J. Biochem., 243, 527-36 |
| Purine analog N2-(cis-2-Aminocyclohexyl)-N6-(3-chlorophenyl)-9-ethyl-9H-purine-2,6-diamine having a molecular formula of $C_{19}H_{24}ClN_7$ available from Sigma-Aldrich under the trade name CGP74514 (#C3353) | Imbach, P. et al., Bioorg. Med. Chem. Lett., 9, 91-96 (1999); Dreyer, M. K. et al., J. Med. Chem., 44, 524-530 (2001). |
| CGP79807, a purine analog of CGP74514 (supra) where Cl is replaced with CN, OH is removed, and the ortho position of cyclohexane ring is $NH_2$ | Imbach, P. et al., Bioorg. Med. Chem. Lett., 9, 91-96 (1999); Dreyer, M. K. et al., J. Med. Chem., 44, 524-530 (2001). |
| purine analog such as O6-cyclohexylmethyl guanine NU2058 | Arris, C. E. et al., J. Med. Chem., 43, 2797-2804 (2000); Davies et al, Nature Structural Biology, 9: 10, 745-749, 2002 |
| purine analog such as NU6102 | Arris, C. E. et al., J. Med. Chem., 43, 2797-2804 (2000); Davies, T. G. et al., Nat. Struct. Biol., 9, 745-749 (2002). |
| isopentenyl-adenine | Vesely, J., et al., (1994) Eur. J. Biochem., 224, 771-86 |
| Nonpurine based agents | |
| Indirubins such as indirubin-3'-monoxime having a molecular formula of $C_{16}H_{11}N_3O_2$ available from Sigma-Aldrich under the trade name (#I0404), indirubin 5-sulfonate, 5-chloro indirubin | Davies, T. G. et al., Structure, 9, 389-397 (2001); Marko, D. et al., Br. J. Cancer, 84, 283-289 (2001); Hoessel, R., et al., (1999) Nat. Cell Biol., 1, 60-7; PCT/US02/30059 to Hellberg et al., published as WO 03/027275. |

TABLE 2-continued c-MAF inhibitors

| Antagonist | Reference for cdk2 inhibitory activity |
|---|---|
| Oxindole 1 of Fischer as referenced in column 2 of this table, (#IN118, JMAR Chemical, Indenopyrazoles | Porcs-Makkay, M., et al., *Tetrahedron* 2000, 56, 5893; *Org. Process Res. Dev.* 2000, 4, 10 Nugiel, D. A. et al., J. Med. Chem., 44, 1334-1336 (2001); Nugiel, D. A. et al., J. Med. Chem., 45, 5224-5232 (2002); Yue, E. W. et al., J. Med. Chem., 45, 5233-5248 (2002). |
| Pyrido(2,3-d)pyrimidine-7-ones, compound 3 of Fischer | Barvian, M. et al., J. Med. Chem., 43, 4606-4616 (2000); Toogood, P. L., Med. Res. Rev., 21, 487-498 (2001). |
| Quinazolines such as anilinoquinazoline | Sielecki, T. M. et al., Bioorg. Med. Chem. Lett., 11, 1157-1160 (2001); Mettey et al., *J. Med. Chem.* 2003, 46, 222-236. |
| Thiazoles such as fused thiazole, 4-{[(7-Oxo-6,7-dihydro-8H-[1,3]thiazolo[5,4-e]indol-8-ylidene)methyl]amino}-N-(2-pyridyl)benzenesulfonamide having a molecular formula of $C_{21}H_{15}N_5O_3S_2$ available from Sigma-Aldrich under the trade name GW8510 (#G7791) | Davis, S. T. et al., Science, 291, 134-137 (2001); PCT/US02/30059 to Hellberg et al., published as WO 03/027275. |
| Flavopiridols such as flavopiridol (L86 8275; NCS 649890, National Cancer Institute, Bethesda, MD) and a dechloro derivative | Carlson, B. A., et al., (1996) Cancer Res., 56, 2973-8 |
| Alkaloids such as Staurosporine (#S1016, A.G. Scientific, San Diego, CA) or UCN-01 (7-hydroxystaurosporine) National Cancer Institute, Bethesda, MD | Rislet, V., et al., (1991) Anticancer Res., 11, 1581-90; Wang, Q., et al., (1995) Cell Growth Differ., 6, 927-36, Akiyama, T., et al., (1997) Cancer Res., 57, 1495-501, Kawakami, K., et al., (1996) Biochem. Biophys. Res. Commun., 219, 778-83 |
| Paullones such as 9-Bromo-7,12-dihydro-indolo[3,2-d][1]benzazepin-6(5H)-one having a molecular formula of $C_{16}H_{11}BrN_2O$ available from Sigma-Aldrich under the trade name kenpaullone (#K3888), or 9-Nitro-7,12-dihydroindolo-[3,2-d][1]benzazepin-6(5)-one having a molecular formula of $C_{16}H_{11}N_3O_3$ available from Sigma-Aldrich under the trade name alsterpaullone (#A4847) | Zaharevitz, D. W. et al., Cancer Res., 59, 2566-2569 (1999); Schultz, C. et al., J. Med. Chem., 42, 2909-2919 (1999); Zaharevitz, D. W., et al., (1999) Cancer Res., 59, 2566-9; PCT/US02/30059 to Hellberg et al., published as WO 03/027275. |
| CGP 41251, an alkaloid | Begemann, M., et al., (1998) Anticancer Res., 18, 2275-82; Fabbro et al., *Pharmacol Ther.* 1999 May-June; 82(2-3): 293-301 |
| Hymenialdisines such as 10z-hymenialdisine having a molecular formula of $C_{11}H_{10}BrN_5O_2$ available from Biochemicals.net, a division of A.G. Scientific, Inc. (San Diego, CA) (H-1150) | Meijer, L., et al., (1999) Chemistry & Biology, 7, 51-63; PCT/US02/30059 to Hellberg et al., published as WO 03/027275. |
| CGP60474, a phenylaminopyrimidine | 21; WO95/09853, Zimmermann et al., Sep. 21, 1994 |
| Thiazolopyrimidine 2 | Attaby et al., *Z. Naturforsch.* 54b, 788-798 (1999) |
| Diarylurea | Honma, T. et al., J. Med. Chem., 44, 4628-4640 (2001), Honma, T. et al., J. Med. Chem., 44, 4615-4627 (2001). |
| (2R)-2,5-Dihydro-4-hydroxy-2-[(4-hydroxy-3-(3-methyl-2-butenyl)phenyl)methyl]-3-(4-hydroxyphenyl)-5-oxo-2-furancarboxylic acid methyl ester having a molecular formula of $C_{24}H_{24}O_7$ available from Sigma-Aldrich under the trade name Butyrolactone-I (B7930) | Kitagawa, M. et al., Oncogene, 8, 2425-2432 (1993). |
| Aloisine A, Cat. No. 128125 (Calbiochem, San Diego, CA) | Mettey et al., *J. Med. Chem.* 2003, 46, 222-236 |

In a preferred embodiment, the c-MAF inhibitory, agents are used for the treatment and/or prevention of bone metastasis. In a yet more preferred embodiment, the bone metastasis is osteolytic metastasis.

The c-MAF inhibitory agents are typically administered in combination with a pharmaceutically acceptable carrier.

The term "carrier" refers to a diluent or an excipient whereby the active ingredient is administered. Such pharmaceutical carriers can be sterile liquids such as water and oil, including those of a petroleum, animal, plant or synthetic origin such peanut oil, soy oil, mineral oil, sesame oil and the like. Water or aqueous saline solutions and aqueous dextrose and glycerol solutions, particularly for injectable solutions, are preferably used as carriers. Suitable pharmaceutical carriers are described in "Remington's Pharmaceutical Sciences" by E. W. Martin, 1995. Preferably, the carriers of the invention are approved by the state or federal government regulatory agency or are listed in the United States Pharmacopeia or other pharmacopeia generally recognized for use thereof in animals and more particularly in human beings.

The carriers and auxiliary substances necessary for manufacturing the desired pharmaceutical dosage form of the pharmaceutical composition of the invention will depend, among other factors, on the pharmaceutical dosage form chosen. Said pharmaceutical dosage forms of the pharmaceutical composition will be manufactured according to the conventional methods known by the person skilled in the art. A review of the different methods for administering active ingredients, excipients to be used and processes for producing them can be found in "Tratado de Farmacia Galenica", C. Fauli i Trillo, Luzán 5, S. A. 1993 Edition. Examples of pharmaceutical compositions include any solid composition (tablets, pills, capsules, granules, etc.) or liquid composition (solutions, suspensions or emulsions) for oral, topical or parenteral administration. Furthermore, the pharmaceutical composition may contain, as deemed necessary, stabilizers, suspensions, preservatives, surfactants and the like.

For use in medicine, the c-MAF inhibitory agents can be found in the form of a prodrug, salt, solvate or clathrate, either isolated or in combination with additional active agents and can be formulated together with a pharmaceutically acceptable excipient. Excipients preferred for use thereof in the present invention include sugars, starches, celluloses, rubbers and proteins. In a particular embodiment, the pharmaceutical composition of the invention will be formulated in a solid pharmaceutical, dosage form (for example tablets, capsules, pills, granules, suppositories, sterile crystal or amorphous solids that can be reconstituted to provide liquid forms etc.), liquid pharmaceutical dosage form (for example solutions, suspensions, emulsions, elixirs, lotions, ointments, etc.) or semisolid pharmaceutical dosage form (gels, ointments, creams and the like). The pharmaceutical compositions of the invention can be administered by any route, including but not limited to the oral route, intravenous route, intramuscular route, intraarterial route, intramedularry route, intrathecal route, intraventricular router, transdermal route, subcutaneous route, intraperitoneal route, intranasal route, enteric route, topical route, sublingual route or rectal route. A review of the different ways for administering active ingredients of the excipients to be used and of the manufacturing processes thereof can be found in Tratado de Farmacia Galenica, C. Fauli i Trillo, Luzán 5, S. A., 1993 Edition and in Remington's Pharmaceutical Sciences (A. R. Gennaro, Ed.), $20^{th}$ edition, Williams & Wilkins PA, USA (2000). Examples of pharmaceutically acceptable carriers are known in the state of art and include phosphate buffered saline solutions, water, emulsions such as oil/water, emulsions, different types of wetting agents, sterile solutions, etc. The compositions comprising said carriers can be formulated by conventional processes known in the state of the art.

In the event that nucleic acids (siRNA, polynucleotides encoding siRNA or shRNA or polynucleotides encoding negative c-MAF dominants) are administered the invention contemplates pharmaceutical compositions particularly prepared for administering said nucleic acids. The pharmaceutical compositions can comprise said naked nucleic acids, i.e., in the absence of compounds protecting the nucleic acids from degradation by the nucleases of the body, which entails the advantage that the toxicity associated with the reagents used for transaction is eliminated. Administration routes suitable for naked compounds include the intravascular route, intratumor route, intracranial route, intraperitoneal route, intrasplenic route, intramuscular route, subretinal route, subcutaneous route, mucosal route, topical route and oral route (Templeton, 2002, DNA Cell Biol., 21:857-867). Alternatively, the nucleic acids can be administered forming part of liposomes conjugated to cholesterol or conjugated to compounds capable of promoting the translocation through cell membranes such as the Tat peptide derived from the HIV-1 TAT protein, the third helix of the homeodomain of the *D. melanogaster* antennapedia protein, the herpes simplex virus VP22 protein, arginine oligomers and peptides as described in WO07069090 (Lindgren, A. et. al., 2000, Trends Pharmacol. Sci, 21:99-103 Schwarze, S. R. et al., 2000, Trends Pharmacol. Sci., 21:45-48, Lundberg, M et al., 2003, Mol Therapy 8:143-150 and Snyder, E. L. and Dowdy, S. F., 2004, Pharm. Res. 21:389-393). Alternatively, the polynucleotide can be administered forming part of a plasmid vector or viral vector, preferably adenovirus-based vectors, in adeno-associated viruses or in retroviruses such as viruses based on murine leukemia virus (MLV) or on lentivirus (HIV, FIV, EIAV).

The c-MAF inhibitory agents or the pharmaceutical compositions containing them can be administered at a dose of less than 10 mg per kilogram of body weight preferably less than 5, 2, 1, 0.5, 0.1, 0.05, 0.01, 0.005, 0.001, 0.0005, 0.0001, 0.00005 or 0.00001 mg per kg of body weight. The unit-dose can be administered by injection, inhalation or topical administration.

The dose depends on the severity and the response of the condition to be treated and it may vary between several days and months or until the condition subsides. The optimal dosage can be determined by periodically measuring the concentrations of the agent in the body of the patient. The optimal dose can be determined from the EC50 values obtained by means of previous in vitro or in vivo assays in animal models. The unit dose can be administered once a day or less than once a day, preferably less than once every 2, 4, 8 or 30 days. Alternatively, it is possible to administer a starting dose followed by one or several maintenance doses, generally of a lesser, amount than the starting dose. The maintenance regimen may involve treating the patient with a dose ranging between 0.01 μg and 1.4 mg/kg of body weight per day, for example 10, 1, 0.1, 0.01, 0.001, or 0.00001 mg per kg of body weight per day. The maintenance doses are preferably administered at the most once every 5, 10 or 30 days. The treatment must be continued for a time that will vary according to the type of disorder the patient suffers, the severity thereof and the condition of the patient. After treatment, the progress of the patient must be monitored to determine if the dose should be increased in the event that the disease does not respond to the treatment or the dose is reduced if an improvement of the disease is observed or if unwanted side effects are observed.

Treatment or Prevention of the Bone Degradation in Lung Cancer Patients with Bone Metastasis, having Elevated c-MAF Levels The present inventors have determined that the c-MAF levels are elevated in metastasis, and in a preferred embodiment, bone metastasis. Patients suffering lung cancer which has metastasized in bone and in which there are elevated c-MAF levels in said metastasis may benefit particularly from therapies aimed at preventing the bone degradation caused by the increased osteoclastic activity.

Thus, in another aspect, the invention relates to the use of an agent for avoiding or preventing bone degradation in the preparation of a medicinal product for the prevention and/or the treatment of the bone metastasis in a subject buffering lung cancer and having elevated c-MAF levels in a metastatic tumor tissue sample with respect to a control sample.

Alternatively, the invention relates to an agent for avoiding or preventing bone degradation for use in the prevention and/or the treatment of the bone, metastasis in a subject suffering lung cancer and has elevated c-MAF levels in a metastatic tumor tissue sample with respect to a control sample.

Alternatively, the invention relates to a method of prevention and/or treatment of the degradation in a subject suffering lung cancer and has elevated c-MAF levels in a metastatic tumor tissue sample with respect to a control sample, which comprises administering an agent for avoiding or preventing bone degradation to said subject.

In a particular embodiment, the bone metastasis is osteolytic metastasis. In another particular embodiment, the lung cancer is NSCLC.

The terms and expressions, "subject", "lung cancer", "tumor sample", "metastasis", "c-MAF gene", "increased or elevated expression levels" and "control sample" have been described in detail in relation with the first method of the invention and are equally applicable to the agent for avoiding or preventing bone degradation.

Agents capable of avoiding or preventing bone degradation suitable for the therapeutic method described in the present invention have been described in detail above in the context of the customized therapy method.

The reference or control sample is a tumor sample of a subject, with lung cancer who has not suffered metastasis or that correspond to the median value of the c-MAF gene expression levels measured in a tumor tissue collection in biopsy samples, of subjects with lung cancer who have not suffered metastasis.

Methods for determining or quantifying if the c-MAF levels are elevated with respect to a control sample have been described in detail in relation with the first method of the invention and are equally applicable to the agent for avoiding or preventing bone degradation.

Alternatively a combined treatment can be carried out, in which more than one agent for avoiding or preventing bone degradation from those mentioned above are combined to treat and/or prevent the metastasis or said agents can be combined with other supplements, such as calcium or vitamin D or with a hormone.

The agents for avoiding or preventing bone degradation are typically administered in combination with a pharmaceutically acceptable carrier. The term "carrier" and the types of carriers have been defined above for the c-MAF inhibitory agents as well as the form and the dose in which they can be administered and are equally applicable to the agent for avoiding or preventing bone degradation.

Kits of the Invention

In another aspect, the invention relates to a kit for predicting bone metastasis of a lung cancer, in a subject suffering from said cancer, the kit comprising: a) means for quantifying the expression level of c-MAF in a sample of said subject; and b) means for comparing the quantified level of expression of c-MAF in said sample to a reference c-MAF expression level.

In another aspect, the invention relates to a kit for predicting the clinical outcome of a subject suffering from bone metastasis from a lung cancer, the kit comprising: a) means for quantifying the expression level of c-MAF in a sample of said subject; and b) means for comparing the quantified expression level of c-MAF in said sample to a reference c-MAF expression level.

In another aspect the invention relates to a kit for determining a therapy for a subject suffering from lung cancer, the kit comprising: a) means for quantifying the expression level of c-MAF in a sample of said subject; b) means for comparing the quantified expression level of c-MAF in said sample to a reference c-MAF expression level; and c) means for determining a therapy for preventing and/or reducing bone metastasis in said subject based on the comparison of the quantified expression level to the reference expression level; d) means for excluding a therapy for preventing and/or reducing bone metastasis in said subject based on the comparison of the quantified expression level to the reference expression level.

In another aspect the invention relates to a kit comprising: i) a reagent for quantifying the expression level of c-MAF in a sample of a subject suffering from lung cancer, and ii) one or more c-MAF gene expression level indices that have been predetermined to correlate with the risk of bone metastasis.

Means for quantifying the expression level of c-MAF in a sample of said subject have been previously described in detail including 16q23 and 16q22-24 locus amplification and translocation.

In a preferred embodiment, means for quantifying expression comprise a set of probes and/or primers that specifically bind and/or amplify the c-MAF gene.

In particular embodiment the lung cancer is SCLC or NSCLC cancer.

In particular embodiment the kit is applied, but not limited, to a lung cancer biopsy, circulating lung cancer cell, circulating lung tumor DNA.

All the particular embodiments of the methods of the present invention are applicable to the kits of the invention and to their uses.

Method for Typing a Sample of a Subject Suffering Lung Cancer.

In another aspect, the invention relates to an in vitro method for typing a sample of a subject suffering from lung cancer, the method comprising:
a) providing a sample from said subject;
b) quantifying the expression level of c-MAF in said sample;
c) typing said sample by comparing the quantified, expression level of c-MAF to a predetermined reference level of c-MAF expression;
wherein said typing provides prognostic information related to the risk of bone metastasis in said subject.

Means for quantifying the expression level of c-MAF in a sample of said subject have been previously described in detail including 16q23 and 16q22-24 locus amplification and translocation. In particular embodiment the lung cancer is SCLC or NSCLC. In a preferred embodiment the sample is a tumor tissue sample, a circulating tumor cell or a circulating tumor DNA.

Method for Classifying a Subject Suffering from Lung Cancer

In another aspect, the invention relates to a method for classifying a subject suffering from lung cancer into a cohort, comprising: a) determining the expression level of c-MAF in a sample of said subject; b) comparing the expression level of c-MAF in said sample to a predetermined reference level of c-MAF expression; and c) classifying said subject into a cohort based on said expression level of c-MAF in the sample.

Means for quantifying the expression level of c-MAF in a sample of said subject have been: previously described in detail including 16q23 and 16q22-24 locus amplification and translocation.

In particular embodiment the lung cancer is a SCLC or a NSCLC. In a preferred embodiment the sample is a tumor tissue sample, a circulating tumor cell or a circulating DNA. In a preferred embodiment said cohort comprises at least one other individual who has been determined to have a comparable expression level of c-MAF in comparison to said reference expression level In another preferred embodiment said expression level of c-MAF in said sample is increased relative to said predetermined reference level, and wherein the members of the cohort are classified as having increased risk of bone metastasis. In another preferred embodiment said cohort is for conducting a clinical trial. In a preferred embodiment, the sample is a tumor tissue sample.

The following examples illustrate the invention and do not limit the scope thereof.

EXAMPLES

Example 1

Clinical Relevance and Prognostic Value of c-MAF and 16q22-24 to Identify Patents at Risk of Metastasis, in Particular bone Metastasis c-MAF was tested in different lung cancer patient sample cohorts. The first including gene expression profiles and clinical annotations for metastasis, that contain the transcriptome of lung cancer primary, tumors and a second cohort based on lung tumor biopsies in the form of a tissue microarray and the clinical annotations for time to bone metastasis and overall survival. These tumors are representative of all lung cancer subtypes and stages. In the first cohort, the expression of c-MAF gene is correlated with clinical parameters including time to metastasis. Similarly, the second set (n=74) of lung primary tumor biopsies for which the clinical annotation for bone relapse and overall survival post primary tumor diagnosis was used to determine, the levels of c-MAF protein expression and 16q23 genomic gain by immunohistochemistry and fluorescence in situ hybridization using a c-MAF specific antibody and a c-MAF locus specific FISH probe and the association between the levels of c-MAF expression and 16q23 genomic gain and risk of bone relapse is established.
Explanation in Detail:
Patient Cohort I We did the appropriate statistical analysis to see if MAF expression in these tumors correlates with metastasis. We used a cohort of lung primary tumors, including EGFR and KRAS mutants and SCLC and NSCLC. The patients' information was extracted from:

Chitale D, Gong Y, Taylor B S, Broderick S, Brennan C, Somwar R, Golas B, Wang L, Motoi N, Szoke J. Reinersman J M, Major J, Sander C, Seshan, V E, Zakowski M F, Rusch V, Pao W, Gerald W, Ladanyi M. "An integrated genomic analysis of lung cancer reveals loss of DUSP4 in EGFR-mutant tumors." Oncogene. 2009; 28: 2773-83.

All statistical analyses were performed in R using Bioconductor (Gentleman et al. (2004)).
We adjusted Cox Proportional Hazards Models (using the R function coxph from Packaged survival) to see if we could explain metastasis phenotype through MAF expression. C-MAF had a statistically significant effect (Using three independent probes specific for c-MAF in affymetrix arrays). Gene expression of c-MAF in lung primary tumors correlated significantly with metastasis as its observed in kaplan meier plot and is highlighted by the HR and the p-value obtained (FIG. 1) Patient cohort II Similarly, a dataset of (74) lung primary tumors for which the clinical annotation for bone relapse post primary tumor diagnosis is available is secured, the levels of c-MAF are determined by immunohistochemistry using a c-MAF specific antibody and the association between the levels of c-MAF expression and risk of bone relapse is established. The samples from the second paraffin embedded primary tumor tissue from lung cancer patients. These samples were collected by Vall d'Hebron Oncology Institute during its clinical practice together with the relevant clinical data needed and the approval of the clinical committee.

The samples were selected fulfill the following requests:
9 samples belonged to patients with local disease (M0) at diagnosis with a confirmed bone relapse at any time of follow-up.

49 samples belonged to patients at diagnosis that remain metastasis free after at least 5 years.

The remaining 16 tumors are from patients M0 at diagnosis that latter had a relapse in any location other than bone.

Example 2 c-MAF Gene Expression is Associated with Risk of Metastasis, in Particular Bone Metastasis, in Lung Cancer Expression of c-MAF bone metastasis genes was correlated with clinical parameters including metastasis using the above described lung cancer expression data set. As described in FIG. 1, c-MAF expression was associated to high risk of metastasis. Following a standard statistical analysis we showed that MAF expression in these tumors significantly correlates with metastasis. A cohort of lung primary tumors, including EGFR and KRAS mutants and SCLC and NSCLG were used. All statistical analyses were performed using Bioconductor (Gentleman et al. (2004)).

The Cox Proportional Hazards Models were adjusted (using the R function coxph from Packaged survival) to see if we could explain metastasis phenotype through MAF expression. c-MAF had a statistically significant effect (Using three independent probes specific for c-MAF in affymetrix arrays). Gene expression of c-MAF in lung primary tumors correlated significantly with metastasis as its observed in kaplan meier plot and is highlighted by the HR and the p-value obtained (FIG. 1). Tumors (were classified according to three groups of c-MAF expression, high (>+1 standard deviation of the mean), medium (<+1 standard deviation of the mean and >−1 standard deviation of the mean) and low (<−1 standard deviation of the mean).

Example 3 c-MAF Expression is Associated with Risk of Bone Metastasis

Immunohistochemistry Analysis cMAF immunostaining was performed on plus charged glass slides in a Dako Link platform. After deparaffination, antigen retrieval was performed. Endogenous peroxidase is quenched. A anti-c-MAF antibody was used, followed by incubation with a secondary antibody coupled with preoxidase. C-MAF immunostaining is scored by a computerized measurement.

Prognostic and Predictive Value of c-MAF for Metastasis and Bone Metastasis in Lung Cancer The prognostic and predictive value of c-MAF expression for metastasis of lung cancer was evaluated. C-MAF protein levels were determined by immunohistochemistry (IHC). MAF immunostaining was scored by a computerized measurement. Nine representative images from each specimen were acquired at 10-nm wavelength intervals between 420 and 700 nm, using a DM2000 Leica microscope equipped with the Nuance FX Multispectral Imaging System (CRI Inc). Before acquiring a spectral dataset of an image, an autoexposure routine was performed while imaging a blank area of slides to determine, the exposure time necessary to approximately 90% fill the device wells at each wavelength to compensate for variations in source intensity, filter transmission efficiency and camera sensitivity. A library of pure DAB and Hematoxylin dye colors was created and used to unmix the colors using the Nuance 1.6.4 software. A cube (stack of images, taken at the different wavelengths) of reference was then acquired for each new case, followed by spectral imaging of three representative tissue fields using the same exposure times. After deconvolution of the images, the spectral data was flat fielded to compensate for unevenness in illumination and background was filtered. The positive signals were converted from transmission to optical density units by taking the negative log of the ratio of the sample divided by the reference cube using a Beer law conversion. A computer-aided threshold was set, which creates a pseudo-color image that highlights all of the positive signals. Analysis yielded quantitative data of c-MAF from the average intensity of regions of interest. Only the nuclei of epithelial cells (normal and malignant), but not stromal cells or lymphocytes, were automatically detected by setting distinct size threshold and confirmed by a pathologist. Each case was calculated for the mean value of the signal intensity of all regions of interest for statistical analysis. The output of the computerized measurement produced a continuous data ranging from 1160 to 99760 optical density units (O.D.) for c-MAF expression. The cut off (20000 O.D.) for high an low expression was determined based on a receiving operating curve as per standard procedures (AUC 0.802). The results are summarized in Table 3.

TABLE 3

|  |  | Bone metastasis | |
|---|---|---|---|
|  |  | NO | Yes |
| c-MAF | <=20,000 OD | 61 | 2 |
|  | >20,000 OD | 4 | 7 |

Based on this values the odds ratio of risk of suffering bone metastasis in the c-MAF high group versus the low was OR (bone metastasis at any time)=53.37 (95% C.I. 8.24-345.92)

Next the time to bone progression of the overall population of the study was confirmed (FIG. 2a) and next the probability of bone metastasis at any time survival-free of the two groups was evaluated (FIG. 2b). Interestingly, in the cohort of study, the c-MAF high expressing tumors have a smaller overall survival than those expressing low levels.

Based on the second cohort analyzed, diagnostic clinical, features were extracted. C-MAF high level expression predicts bone metastasis with a sensitivity of 0.778, a specificity of 0.938, a positive predictive value of 63.6%, and a negative predictive value of 96.8%.

The c-MAF gene or protein expression in lung tumors correlates significantly with metastasis and bone metastasis at any time.

Example 4

16q22-q24 (Includes c-MAF Gene) Chromosome Amplification Predicts and is a Prognostic Indicator of Risk of Metastasis, in Particular Bone Metastasis, in Lung Cancer Next, we determined whether a gain in chr16q22-q24, which includes c-MAF gene locus, is associated with risk of bone metastasis in lung cancer patients. To this end a 16q23 14q32 dual fluorescence in situ hybridization (FISH) probe that identifies chr16q22-q24 amplifications was used to measure the number of copies of the 16q22-24 region. The 14q32 probe was also used to normalize tumor polyploidy.

The prognostic and predictive value of 16q22-24 CNA gain association with bone metastasis in lung cancer was evaluated. 16q23 and 14q32 copies were determined by FISH. The slides were incubated with 16q23 MAF and 14q32IGH probe mixture. This SpectrumOrange probe flanks the MAF gene region and is composed of two segments that are each approximately 350 kb with an approximately 2.2 Mb gap. The centromeric segment is located at chr16:75729985-76079705 (March 2006 assembly, UCSC Genome Browser) and the telomeric segment is located at chr16:78290003-78635873 (March 2006 assembly, UCSC Genome Browser). This probe flanks five genes VAT1L, CLEC3A, WWOX, 5srRNA and MAF (ordered from centromer to telomer). In parallel, a CEP 16 (centromeric chr. 16) probe (Abbot) was used to determine the CNA. CEP 16 (16q11.2) (Abbot) probe was used to score 16q23 CNA. DAPI counterstain was applied and images were acquired with a fluorescence microscope.

The results are summarized in Tables 4 and 5.

TABLE 4

A tumor will be positive for a 16q22-24 gain based on a cut off >= to 2.5 copies of the 16q23

|  |  | Bone metastasis | |
|---|---|---|---|
|  |  | NO | Yes |
| 16q23 | <=2.5 | 13 | 9 |
| FISH | >2.5 | 44 | 0 |

TABLE 5

A tumor will be positive for a 16q22-24 CAN gain based on a cut off >= to 1.5 copies of the 16q23 normalized by number of the copies of the 14q23.

|  |  | Bone metastasis | |
|---|---|---|---|
|  |  | NO | Yes |
| 16q23 | <=1.5 | 4 | 9 |
| CNA | >1.5 | 53 | 0 |

Based on these values the odds ratio of risk of suffering bone metastasis in the 16q22-24 gain or CNA gain positive group versus the negative was calculated. Since there were no patients with bone metastasis that score negative for the determination and in order to avoid errors on the estimation, as per standard statistical procedures (Glas, A. S. et al., 2003, Journal of Clinical Epidemiology 56, 1129-1135), 0.5 units were added to each value and recalculated the parameter. Based on this estimation, the OR for the 16q22-24 gain positive patients to suffer a bone metastasis was 62.63 (95% CI 3.42-1147.78), and the OR for the 16q22-24 CNA gain normalized using 14q32 positive patients versus the control was 225.89 (95% CI 11.22-4546.99). The small size of the cohort made the estimates imprecise but within a clinically relevant OR of least 3.42 and 11.22 in each case.

Based on the data using FISH in order to measure 16q23 gains, diagnostic clinical features were extracted. 16q22-24 gain (>=2.5 copies per cell) predicts lung cancer patients at high risk of bone metastasis with a sensitivity of 1.00, a specificity of 0.772, a positive predictive value of 40.9%, and a negative predictive value of 100.0%.

TABLE 6

Diagnostic clinical features.

| | | C.I. 95% |
|---|---|---|
| Sensitivity | 100.0% | 70.1%-100.0% |
| Specificity | 77.2% | 64.8%-86.2% |
| PPV | 40.9% | 23.3%-61.3% |
| NPV | 100.0% | 92.0%-100.0% |

Based on the data using FISH in order to measure 16q23 gains normalized to 14q32 copies, diagnostic clinical features were extracted. 16q22-24 CNA gain (>=1.5 16q23 copies per cell normalized to 14q32) predicts lung cancer risk of bone metastasis with a sensitivity of 1.00, a specificity of 0.930, a positive predictive value of 69.2%, and a negative predictive value of 100.0%.

TABLE 7

Diagnostic clinical features

| | | CI 95% |
|---|---|---|
| Sensitivity | 100.0% | 70.1%-100.0% |
| Specificity | 93.0% | 83.3%-97.2% |
| PPV | 69.2% | 42.4%-87.3% |
| NPV | 100.0% | 93.2%-100.0% |

The 16q22-24, and particularly 16q23, amplification/gain or CNA gain in lung tumors strongly predicts and is associated with risk of bone metastasis at any time.

The invention claimed is:

1. An in vitro method for a customized therapy for a subject with lung cancer with bone metastasis comprising,
   (i) quantifying the c-MAF gene expression level, amplification or copy number in a tumor sample of said subject;
   (ii) determining that the subject has an increase in the expression level, copy number or amplification of the c-MAF gene in the tumor sample with respect to the expression level, copy number or amplification of the c-MAF gene in the control sample, and then said subject receives a therapy aiming to prevent and/or treat the bone metastasis and/or prevent and/or treat bone degradation, wherein the therapy aiming to prevent and/or treat the bone metastasis is a c-MAF inhibitor and/or wherein the therapy aiming to prevent and/or treat the bone degradation is selected from the group consisting of a bisphosphonate, a RANKL inhibitor, a PTH or a PTHLH inhibitor, strontium ranelate, calcitonin, and a cathepsin K inhibitor.

2. The method according to claim 1, wherein the bone metastasis is osteolytic bone metastasis.

3. The method according to claim 1, wherein the expression level, copy number or amplification is quantified by means of quantitative polymerase chain reaction (PCR) or a DNA or RNA array, nucleotide hybridization technique, western blot, in situ hybridization, ELISA, immunohistochemistry or a protein array.

4. The method according to claim 1, wherein the RANKL inhibitor is selected from the group consisting of: a RANKL specific antibody, a RANKL specific nanobody, and osteoprotegerin.

5. The method according to claim 1, wherein the RANKL inhibitor is the RANKL specific antibody denosumab, the bisphosphonate is zoledronic acid or clodronate, and the RANKL inhibitor is the RANKL specific nanobody ALX-0141.

6. An in vitro method for a customized therapy for a subject with lung cancer, comprising:
   (i) detecting c-MAF amplification in a tumor sample of said subject relative to a reference gene copy number, wherein the amplification of the c-MAF gene is determined by means of determining the amplification of the locus 16q22-q24, wherein an amplification of the c-MAF gene with respect to said reference gene copy number is indicative of the presence of metastasis or an increased risk of developing metastasis, and then said subject receives a therapy aiming to prevent and/or treat the metastasis and/or prevent and/or treat bone degradation, wherein the therapy aiming to prevent and/or treat the metastasis is a c-MAF inhibitor and/or wherein the therapy aiming to prevent and/or treat the bone degradation is selected from the group consisting of a bisphosphonate, a RANKL inhibitor, a PTH or a PTHLH inhibitor, strontium ranelate, calcitonin, and a cathepsin K inhibitor.

7. The method according to claim 6, wherein the metastasis is bone metastasis.

8. The method according to claim 7, wherein the bone metastasis is osteolytic bone metastasis.

9. The method according to claim 6, wherein the amplification is quantified by means of in situ hybridization or PCR.

10. The method according to claim 6, wherein the RANKL inhibitor is selected from the group consisting of: a RANKL specific antibody, a RANKL specific nanobody, and osteoprotegerin.

11. The method according to claim 6, wherein the RANKL inhibitor is the RANKL specific antibody denosumab, the bisphosphonate is zoledronic acid, and the RANKL inhibitor is the RANKL specific nanobody ALX-0141.

12. The method of claim 1, wherein the therapy aiming to prevent and/or treat the bone degradation is a bisphosphonate.

13. The method of claim 6, wherein the therapy aiming to prevent and/or treat the bone degradation is a bisphosphonate.

14. The method according to claim 12, wherein the bisphosphonate is zoledronic acid or clodronate.

15. The method according to claim 13, wherein the bisphosphonate is zoledronic acid or clodronate.

\* \* \* \* \*

SEQUENCE LISTING

<160> NUMBER OF SEQ ID NOS: 13

<210> SEQ ID NO 1
<211> LENGTH: 6878
<212> TYPE: DNA
<213> ORGANISM: Homo sapiens

<400> SEQUENCE: 1

```
agaggcttta aaatcttttt tcatcttcta gctgtagctc gggctgcttg tcggcttggc    60 ctcccctcc ccctttgct ctctgcctcg tctttcccca ggacttcgct attttgcttt    120
tttaaaaaaa ggcaagaaag aactaaactc cccctcct ctcctccagt cgggctgcac    180
ctctgccttg cactttgcac agaggtagag agcgcgcgag ggagagagag gaaagaaaaa    240
aaataataaa gagagccaag cagaagagga ggcgagaagc atgaagtgtt aactcccccg    300
tgccaaggcc cgcgccgccc ggacagacgc ccgccgcgcc tccagccccg agcggacgcc    360
gcgcgcgccc tgcctgcagc ccgggccggc gaggcgagcc cttccttatg caaagcgcgc    420
agcggagcgg cgagcggggg acgccgcgca ccgggccggg ctcctccagc ttcgccgccg    480
cagccaccac cgccgccacc gcagctcgcg gaggatcttc ccgagcctga agccgccggc    540
tcggcgcgca aggaggcgag cgagcaagga ggggccgggg cgagcgaggg agcacattgg    600
cgtgagcagg ggggagggag ggcgggcgcg ggggcgcgg gcagggcggg ggggtgtgtg    660
tgtgagcgcg ctcggaggtt tcgggccagc caccgccgcg caagctagaa gcgccccagc    720
ccggcaagct ggctcacccg ctggccaccc agcacagccc gctggcccct ctcctgcagc    780
ccatctggcg gagcggcggc ggcggcggcg gcggcggcag gagaatggca tcagaactgg    840
caatgagcaa ctccgacctg cccaccagtc ccctggccat ggaatatgtt aatgacttcg    900
atctgatgaa gtttgaagtg aaaaaggaac cggtggagac cgaccgcatc atcagccagt    960
gcggccgtct catcgccggg ggctcgctgt cctccacccc catgagcacg ccgtgcagct    1020
cggtgccccc ttcccccagc ttctcggcgc ccagcccggg ctcgggcagc gagcagaagg    1080
cgcacctgga agactactac tggatgaccg gctaccgca gcagctgaac cccgaggcgc    1140
tgggcttcag ccccgaggac gcggtcgagg cgctcatcag caacagccac cagctccagg    1200
gcggcttcga tggctacgcg cgcggggcgc agcagctggc cgcggcggcc ggggccggtg    1260
ccggcgcctc cttgggcggc agcggcgagg agatgggccc cgccgccgcc gtggtgtccg    1320
ccgtgatcgc cgcggccgcc gcgcagagcg cgcgggccc gcactaccac caccaccacc    1380
accacgccgc cggccaccac caccacccga ccgccggcgc gcccggcgcc gcgggcagcg    1440
cggccgcctc ggccggtggc gctggggcg cgggcggcgg tggcccggcc agcgctgggg    1500
```

```
gcggcggcgg cggcggcggc ggcggaggcg gcggggcgc ggcggggcg ggggcgccc    1560 tgcacccgca ccacgccgcc ggcggcctgc acttcgacga ccgcttctcc gacgagcagc   1620
tggtgaccat gtctgtgcgc gagctgaacc ggcagctgcg cggggtcagc aaggaggagg   1680
tgatccggct gaagcagaag aggcggaccc tgaaaaaccg cggctatgcc cagtcctgcc   1740
gcttcaagag ggtgcagcag agacacgtcc tggagtcgga agaaccag ctgctgcagc    1800 aagtcgacca cctcaagcag gagatctcca ggctggtgcg cgagagggac gcgtacaagg   1860
agaaatacga gaagttggtg agcagcggct tccgagaaaa cggctcgagc agcgacaacc   1920
cgtcctctcc cgagtttttc atgtgagtct gacacgcgat tccagctagc caccctgata   1980
agtgctccgc gggggtccgg ctcgggtgtg ggcttgctag ttctagagcc atgctcgcca   2040
ccacctcacc accccacccc caccgagtt tggccccctt ggcccctac acacacacaa    2100 acccgcacgc acacaccaca cacacacaca cacacacaca cacacccac acctgctcg    2160 agtttgtggt ggtggtggct gttttaaact ggggagggaa tgggtgtctg gctcatggat   2220
tgccaatctg aaattctcca taacttgcta gcttgttttt tttttttttt tacacccccc   2280
cgccccaccc ccggacttgc acaatgttca atgatctcag cagagttctt catgtgaaac   2340
gttgatcacc tttgaagcct gcatcattca catattttt cttcttcttc cccttcagtt    2400
catgaactgg tgttcatttt ctgtgtgtgt gtgtgtttta ttttgtttgg attttttttt   2460
ttaattttac ttttagagct tgctgtgttg cccacctttt ttccaacctc caccctcact   2520
ccttctcaac ccatctcttc cgagatgaaa gaaaaaaaaa agcaaagttt ttttttcttc   2580
tcctgagttc ttcatgtgag attgagcttg caaaggaaaa aaaaatgtga aatgttatag   2640
acttgcagcg tgccgagttc catcgggttt ttttttttagc attgttatgc taaaatagag   2700
aaaaaaatcc tcatgaacct tccacaatca agcctgcatc aaccttctgg gtgtgacttg   2760
tgagttttgg ccttgtgatg ccaaatctga gagtttagtc tgccattaaa aaaactcatt   2820
ctcatctcat gcattattat gcttgctact tgtcttagc aacaatgaac tataactgtt     2880
tcaaagactt tatggaaaag agacattata ttaataaaaa aaaaaagcct gcatgctgga   2940
catgtatggt ataattattt ttttcctttt ttttcctttt ggcttggaaa tggacgttcg   3000
aagacttata gcatggcatt catactttg ttttattgcc tcatgacttt tttgagttta    3060
gaacaaaaca gtgcaaccgt agagccttct tcccatgaaa ttttgcatct gctccaaaac   3120
tgctttgagt tactcagaac ttcaacctcc caatgcactg aaggcattcc ttgtcaaaga   3180
taccagaatg ggttacacat ttaacctggc aaacattgaa gaactcttaa tgttttcttt   3240
ttaataagaa tgacgcccca ctttggggac taaaattgtg ctattgccga aagcagtct    3300 aaaatttatt ttttaaaaag agaaactgcc ccattatttt tggtttgttt tatttttatt   3360
ttatattttt tggcttttgg tcattgtcaa atgtggaatg ctctgggttt ctagtatata   3420
atttaattct agttttttata atctgttagc ccagttaaaa tgtatgctac agataaagga   3480
atgttataga taaatttgaa agagttaggt ctgtttagct gtagattttt taaacgattg   3540
atgcactaaa ttgtttacta ttgtgatgtt aaggggggta gagtttgcaa ggggactgtt   3600 taaaaaagt agcttataca gcatgtgctt gcaacttaaa tataagttgg gtatgtgtag    3660
tctttgctat accactgact gtattgaaaa ccaaagtatt aagagggaa acgcccctgt    3720 ttatatctgt agggtattt tacattcaaa aatgtatgtt tttttttctt ttcaaaatta    3780
aagtatttgg gactgaattg cactaagata taacctgcaa gcatataata caaaaaaaaa   3840
ttgcaaaact gtttagaacg ctaataaaat ttatgcagtt ataaaaatgg cattactgca   3900
```

```
cagttttaag atgatgcaga ttttttttaca gttgtattgt ggtgcagaac tggatttttct    3960 gtaacttaaa aaaaaatcca cagttttaaa ggcaataatc agtaaatgtt attttcaggg    4020
actgacatcc tgtcttttaaa aagaaatgaa aagtaaatct taccacaata aatataaaaa    4080
aatcttgtca gttactttttc ttttacatat tttgctgtgc aaaattgttt tatatcttga    4140
gttactaact aaccacgcgt gttgttccta tgtgcttttc tttcattttc aattctggtt    4200
atatcaagaa aagaataatc tacaataata aacggcattt tttttttgatt ctgtactcag    4260 tttcttagtg tacagtttaa ctgggcccaa caacctcgtt aaaagtgtaa aatgcatcct    4320
tttctccagt ggaaggattc ctggaggaat agggagacag taattcaggg tgaaattata    4380
ggctgttttt tgaagtgagg aggctggccc catatactga ttagcaatat ttaatataga    4440
tgtaaattat gacctcattt ttttctcccc aaagttttca gttttcaaat gagttgagcc    4500
ataattgccc ttggtaggaa aaacaaaaca aaacagtgga actaggcttc ctgagcatgg    4560
ccctacactt ctgatcagga gcaaagccat ccatagacag aggagccgga caaatatggc    4620
gcatcagagg tggcttgcgc acatatgcat tgaacggtaa agagaaacag cgcttgcctt    4680
ttcactaaag ttgactatttt ttccttcttc tcttacacac cgagatttttc ttgttagcaa    4740 ggcctgacaa gatttaacat aaacatgaca aatcatagtt gtttgttttg ttttgctttt    4800
ctctttaaca ctgaagatca tttgtcttaa ataggaaaaa gaaatccac tccttacttc    4860 catatttcca agtacatatc tggtttaaac tatgttatca aatcatattt caccgtgaat    4920
attcagtgga gaacttctct acctggatga gctagtaatg atttcagatc atgctatccc    4980
cagaaataaa agcaaaaaat aatacctgtg tggaatatag gctgtgctt gatttactgg    5040 tatttacccc aaaataggct gtgtatgggg gctgacttaa agatcccttg gaaagactca    5100
aaactacctt cactagtagg actcctaagc gctgacctat ttttaaatga cacaaattca    5160
tgaaactaat gttacaaatt catgcagttt gcactcttag tcatcttccc ctagcacacc    5220
aatagaatgt tagacaaagc cagcactgtt ttgaaaatac agccaaacac gatgactttt    5280
gttttgtttt ctgccgttct taaaagaaaa aaagataata ttgcaactct gactgaaaga    5340 cttatttttta agaaaacagg ttgtgtttgg tgctgctaag ttctggccag tttatcatct    5400
ggccttcctg cctatttttt acaaaacacg aagacagtgt gtaacctcga cattttgacc    5460
ttcctttatg tgctagttta dacaggctcc tgaatccaca cttaatttttg cttaacaaaa    5520 gtcttaatag taaacctccc ctcatgagct tgaagtcaag tgttcttgac ttcagatatt    5580
tctttccttt tttttttttt ttcctcatca caactaagag atacacaaac tctgaagaag    5640
cagaaatgga gagaatgctt ttaacaaaaa agcatctgat gaaagatttt aggcaaacat    5700
tctcaaaata agagtgatat tctggatgta gttattgcag ttatctcatg acaaatgagg    5760
cctggattgg aaggaaaata tagttgtgta gaattaagca ttttgatagg aatctacaag    5820
gtagttgaat ataataagca ggtttgggcc cccaaacttt agaaaatcaa atgcaaaggt    5880
gctggcaaaa atgaggtttg agtggctggc tgtaagagaa ggttaactcc tagtaaaagg    5940 cattttttaga aataacaatt actgaaaact ttgaagtata gtgggagtag caaacaaata    6000
catgtttttt ttttcttaca aagaactcct aaatcctgag taagtgccat tcattacaat    6060
aagtctctaa atttaaaaaa aaaaaaatca tatgaggaaa tctagctttc cccttttacgc    6120 tgcgtttgat ctttgtctaa atagtgttaa aattcctttc attccaatta cagaactgag    6180
cccactcgca agttggagcc atcagtggga tacgccacat tttggaagcc ccagcatcgt    6240
gtacttacca gtgtgttcac aaaatgaaat ttgtgtgaga gctgtacatt aaaaaaaatc    6300
```

| | | |
|---|---|---|
| atcattatta ttattatttg cagtcatgga gaaccaccta cccctgactt ctgtttagtc | 6360 | |
| tccttttaa ataaaaatta ctgtgttaga gaagaaggct attaaatgta gtagttaact | 6420 | |
| atgcctcttg tctgggggtt tcatagagac cggtaggaaa gcgcactcct gcttttcgat | 6480 | |
| ttatggtgtg tgcaagtaaa caggtgcatt gctttcaacc tgccatacta gttttaaaaa | 6540 | |
| ttcactgaaa ttacaaagat acatatatat gcatatatat aatggaaagt ttcccggaat | 6600 | |
| gcaacaatta gcattttaaa atcatatata ggcatgcaca ttctaaatag tactttttca | 6660 | |
| tgcttcattg tttctctggc agataatttt actaagaaga aaaatagata ttcgactccc | 6720 | |
| cttccctaaa caaatccacg ggcagaggct ccagcggagc cgagccccct ggttttctcg | 6780 | |
| taggccctag acggtgttgc atttatcagt gatgtcaaac gtgctcattt gtcagacata | 6840 | |
| gctgtaaatg aaaacaatgt gtggcaaaat acaaagtt | 6878 | |

<210> SEQ ID NO 2
<211> LENGTH: 2656
<212> TYPE: DNA
<213> ORGANISM: Homo sapiens

<400> SEQUENCE: 2

| | | |
|---|---|---|
| gaggctttaa aatctttttt catcttctag ctgtagctcg ggctgcttgt cggcttggcc | 60 | |
| tcccctccc cccttgtctc tctgcctcgt cttcccag gacttcgcta ttttgctttt | 120 | |
| ttaaaaaaag gcaagaaaga actaaactcc cccctccctc tcctccagtc gggctgcacc | 180 | |
| tctgccttgc actttgcaca gaggtagaga gcgcgcgagg gagagagagg aaagaaaaaa | 240 | |
| aataataaag agagccaagc agaagaggag gcgagaagca tgaagtgtta actccccgt | 300 | |
| gccaaggccc gcgccgcccg gacagacgcc cgccgcgcct ccagccccga gcggacgccg | 360 | |
| cgcgcgccct gcctgcagcc cgggccggcg aggcgagccc ttccttatgc aaagcgcgca | 420 | |
| gcggagcggc gagcggggga cgccgcgcac cgggccgggc tcctccagct tcgccgccgc | 480 | |
| agccaccacc gccgccaccg cagctcgcgg aggatcttcc cgagcctgaa gccgccggct | 540 | |
| cggcgcgcaa ggaggcgagc gagcaaggag gggccggggc gagcgaggga gcacattggc | 600 | |
| gtgagcaggg gggagggagg gcgggcgcgg ggggcgcggg cagggcgggg gggtgtgtgt | 660 | |
| gtgagcgcgc tcggaggttt cgggccagcc accgccgcgc aagctagaag cgccccagcc | 720 | |
| cggcaagctg gctcacccgc tggccaccca gcacagcccg ctggcccctc tcctgcagcc | 780 | |
| catctggcgg agcggcggcg gcggcggcgg cggcggcagg agaatggcat cagaactggc | 840 | |
| aatgagcaac tccgacctgc ccaccagtcc cctggccatg gaatatgtta atgacttcga | 900 | |
| tctgatgaag tttgaagtga aaaggaacc ggtggagacc gaccgcatca tcagccagtg | 960 | |
| cggccgtctc atcgcggggg gctcgctgtc ctccacccc atgagcacgc cgtgcagctc | 1020 | |
| ggtgccccct tcccccagct tctcggcgcc cagcccgggc tcgggcagcg agcagaaggc | 1080 | |
| gcacctggaa gactactact ggatgaccgg ctacccgcag cagctgaacc ccgaggcgct | 1140 | |
| gggcttcagc cccgaggacg cggtcgaggc gctcatcagc aacagccacc agctccaggg | 1200 | |
| cggcttcgat ggctacgcgc gcggggcgca gcagctggcc gcggcggccg gggccggtgc | 1260 | |
| cggcgcctcc ttgggcggca gcgccgagga gatgggcccc gccgccgccg tggtgtccgc | 1320 | |
| cgtgatcgcc gcggccgccg cgcagagcgg cgcgggcccc cactaccacc accaccacca | 1380 | |
| ccacgccgcc ggccaccacc acccccgac ggccggccgcg cccggcgccg cgggcagcgc | 1440 | |
| ggccgcctcg gccggtggcg ctgggggcgc gggcggcggt ggcccggcca gcgctggggg | 1500 | |
| cggcggcggc ggcggcggcg gcggaggcgg cggggggcgcg gcggggggcgg ggggcgccct | 1560 | |

| | |
|---|---|
| gcacccgcac cacgccgccg gcggcctgca cttcgacgac cgcttctccg acgagcagct | 1620 |
| ggtgaccatg tctgtgcgcg agctgaaccg gcagctgcgc ggggtcagca aggaggaggt | 1680 |
| gatccggctg aagcagaaga ggcggaccct gaaaaaccgc ggctatgccc agtcctgccg | 1740 |
| cttcaagagg gtgcagcaga gacacgtcct ggagtcggag aagaaccagc tgctgcagca | 1800 |
| agtcgaccac ctcaagcagg agatctccag gctggtgcgc gagagggacg cgtacaagga | 1860 |
| gaaatacgag aagttggtga gcagcggctt ccgagaaaac ggctcgagca gcgacaaccc | 1920 |
| gtcctctccc gagttttca taactgagcc cactcgcaag ttggagccat cagtgggata | 1980 |
| cgccacattt tggaagcccc agcatcgtgt acttaccagt gtgttcacaa aatgaaattt | 2040 |
| gtgtgagagc tgtacattaa aaaaaatcat cattattatt attatttgca gtcatggaga | 2100 |
| accacctacc cctgacttct gtttagtctc ctttttaaat aaaaattact gtgttagaga | 2160 |
| agaaggctat taaatgtagt agttaactat gcctcttgtc tgggggtttc atagagaccg | 2220 |
| gtaggaaagc gcactcctgc ttttcgattt atggtgtgtg caagtaaaca ggtgcattgc | 2280 |
| tttcaacctg ccatactagt tttaaaaatt cactgaaatt acaaagatac atatatatgc | 2340 |
| atatatataa tggaaagttt cccggaatgc aacaattagc attttaaaat catatatagg | 2400 |
| catgcacatt ctaaatagta ctttttcatg cttcattgtt tctctggcag ataattttac | 2460 |
| taagaagaaa aatagatatt cgactcccct tccctaaaca aatccacggg cagaggctcc | 2520 |
| agcggagcca agcccctgg ttttctcgta ggccctagac ggtgttgcat ttatcagtga | 2580 |
| tgtcaaacgt gctcatttgt cagacatagc tgtaaatgaa acaatgtgt ggcaaaatac | 2640 |
| aaagttaaaa aaaaaa | 2656 |

<210> SEQ ID NO 3
<211> LENGTH: 6887
<212> TYPE: DNA
<213> ORGANISM: Homo sapiens

<400> SEQUENCE: 3

| | |
|---|---|
| gaggctttaa aatcttttt catcttctag ctgtagctcg ggctgcttgt cggcttggcc | 60 |
| tccccctccc cccttgctc tctgcctcgt cttcccag gacttcgcta ttttgctttt | 120 |
| ttaaaaaaag gcaagaaaga actaaactcc cccctccctc tcctccagtc gggctgcacc | 180 |
| tctgccttgc actttgcaca gaggtagaga gcgcgcgagg gagagagagg aaagaaaaaa | 240 |
| aataataaag agagccaagc agaagaggag gcgagaagca tgaagtgtta actcccccgt | 300 |
| gccaaggccc gcgccgcccg gacagacgcc cgccgcgcct ccagccccga gcggacgccg | 360 |
| cgcgcgccct gcctgcagcc cgggccggcg aggcgagccc ttccttatgc aaagcgcgca | 420 |
| gcggagcggc gagcggggga cgccgcgcac cgggccgggc tcctccagct tcgccgccgc | 480 |
| agccaccacc gccgccaccg cagctcgcgg aggatcttcc cgagcctgaa gccgccggct | 540 |
| cggcgcgcaa ggaggcgagc gagcaaggag gggccggggc gagcgaggga gcacattggc | 600 |
| gtgagcaggg gggagggagg gcgggcgcgg ggggcgcggg cagggcgggg gggtgtgtgt | 660 |
| gtgagcgcgc tcggaggttt cgggccagcc accgccgcgc aagctagaag cgccccagcc | 720 |
| cggcaagctg gctcacccgc tggccaccca gcacagcccg ctggcccctc tcctgcagcc | 780 |
| catctggcgg agcggcggcg gcggcggcgg cggcggcagg agaatggcat cagaactggc | 840 |
| aatgagcaac tccgacctgc ccaccagtcc cctggccatg gaatatgtta atgacttcga | 900 |
| tctgatgaag tttgaagtga aaaggaacc ggtggagacc gaccgcatca tcagccagtg | 960 |
| cggccgtctc atcgccgggg gctcgctgtc ctccacccc atgagcacgc cgtgcagctc | 1020 |

```
ggtgcccct  tccccagct  tctcggcgcc  cagcccgggc  tcgggcagcg  agcagaaggc      1080
gcacctggaa  gactactact  ggatgaccgg  ctacccgcag  cagctgaacc  ccgaggcgct      1140
gggcttcagc  cccgaggacg  cggtcgaggc  gctcatcagc  aacagccacc  agctccaggg      1200
cggcttcgat  ggctacgcgc  gcggggcgca  gcagctggcc  gcggcggccg  gggccggtgc      1260
cggcgcctcc  ttgggcggca  gcggcgagga  gatgggcccc  gccgccgccg  tggtgtccgc      1320
cgtgatcgcc  gcggccgccg  cgcagagcgg  cgcgggcccg  cactaccacc  accaccacca      1380
ccacgccgcc  ggccaccacc  accacccgac  ggccggcgcg  cccggcgccg  cgggcagcgc      1440
ggccgcctcg  gccggtggcg  ctgggggcgc  gggcggcggt  ggcccggcca  gcgctggggg      1500
cggcggcggc  ggcggcggcg  gcggaggcgg  cggggcgcg  gcggggcgg  ggggcgccct      1560 gcacccgcac  cacgccgccg  gcggcctgca  cttcgacgac  cgcttctccg  acgagcagct      1620
ggtgaccatg  tctgtgcgcg  agctgaaccg  gcagctgcgc  ggggtcagca  aggaggaggt      1680
gatccggctg  aagcagaaga  ggcggaccct  gaaaaaccgc  ggctatgccc  agtcctgccg      1740
cttcaagagg  gtgcagcaga  gacacgtcct  ggagtcggag  aagaaccagc  tgctgcagca      1800
agtcgaccac  ctcaagcagg  agatctccag  gctggtgcgc  gagagggacg  cgtacaagga      1860
gaaatacgag  aagttggtga  gcagcggctt  ccgagaaaac  ggctcgagca  gcgacaaccc      1920
gtcctctccc  gagttttca  tgtgagtctg  acacgcgatt  ccagctagcc  accctgataa      1980
gtgctccgcg  ggggtccggc  tcgggtgtgg  gcttgctagt  tctagagcca  tgctcgccac      2040
cacctcacca  cccccacccc  caccgagttt  ggcccccttg  gccccctaca  cacacacaaa      2100
cccgcacgca  cacaccacac  acacacacac  acacacacac  acaccccaca  ccctgctcga      2160
gtttgtggtg  gtggtggctg  ttttaaactg  gggagggaat  gggtgtctgg  ctcatggatt      2220
gccaatctga  aattctccat  aacttgctag  cttgttttt  tttttttttt  acacccccc      2280 gccccacccc  cggacttgca  caatgttcaa  tgatctcagc  agagttcttc  atgtgaaacg      2340
ttgatcacct  ttgaagcctg  catcattcac  atatttttc  ttcttcttcc  ccttcagttc      2400
atgaactggt  gttcatttc  tgtgtgtgtg  tgtgttat  tttgtttgga  ttttttttt      2460 taattttact  tttagagctt  gctgtgttgc  ccacctttt  tccaacctcc  accctcactc      2520
cttctcaacc  catctcttcc  gagatgaaag  aaaaaaaaaa  gcaaagttt  ttttcttct      2580 cctgagttct  tcatgtgaga  ttgagcttgc  aaaggaaaaa  aaaatgtgaa  atgttataga      2640
cttgcagcgt  gccgagttcc  atcgggtttt  tttttagca  ttgttatgct  aaaatagaga      2700 aaaaatcct  catgaacctt  ccacaatcaa  gcctgcatca  accttctggg  tgtgacttgt      2760
gagttttggc  cttgtgatgc  caaatctgag  agtttagtct  gccattaaaa  aaactcattc      2820
tcatctcatg  cattattatg  cttgctactt  tgtcttagca  acaatgaact  ataactgttt      2880
caaagacttt  atggaaaaga  gacattatat  taataaaaaa  aaaagcctg  catgctggac      2940 atgtatggta  taattatttt  ttccttttt  tttccttttg  gcttggaaat  ggacgttcga      3000
agacttatag  catggcattc  atactttgt  tttattgcct  catgactttt  ttgagtttag      3060
aacaaaacag  tgcaaccgta  gagccttctt  cccatgaaat  tttgcatctg  ctccaaaact      3120
gctttgagtt  actcagaact  tcaacctccc  aatgcactga  aggcattcct  tgtcaaagat      3180
accagaatgg  gttacacatt  taacctggca  aacattgaag  aactcttaat  gttttctttt      3240
taataagaat  gacgccccac  tttggggact  aaaattgtgc  tattgccgag  aagcagtcta      3300
aaatttattt  tttaaaaaga  gaaactgccc  cattattttt  ggtttgtttt  attttattt      3360 tatatttttt  ggcttttggt  cattgtcaaa  tgtggaatgc  tctgggtttc  tagtatataa      3420
```

```
tttaattcta gttttataa tctgttagcc cagttaaaat gtatgctaca gataaaggaa    3480
tgttatagat aaatttgaaa gagttaggtc tgtttagctg tagatttttt aaacgattga    3540
tgcactaaat tgtttactat tgtgatgtta agggggtag agtttgcaag gggactgttt    3600
aaaaaaagta gcttatacag catgtgcttg caacttaaat ataagttggg tatgtgtagt    3660
ctttgctata ccactgactg tattgaaaac caaagtatta agaggggaaa cgcccctgtt    3720
tatatctgta ggggtatttt acattcaaaa atgtatgttt ttttttcttt tcaaaattaa    3780
agtatttggg actgaattgc actaagatat aacctgcaag catataatac aaaaaaaaat    3840
tgcaaaactg tttagaacgc taataaaatt tatgcagtta taaaaatggc attactgcac    3900
agttttaaga tgatgcagat tttttacag ttgtattgtg gtgcagaact ggattttctg    3960
taacttaaaa aaaatccac agttttaaag gcaataatca gtaaatgtta ttttcaggga    4020
ctgacatcct gtctttaaaa agaaatgaaa agtaaatctt accacaataa atataaaaaa    4080
atcttgtcag ttactttct tttacatatt ttgctgtgca aaattgtttt atatcttgag    4140
ttactaacta accacgcgtg ttgttcctat gtgcttttct ttcattttca attctggtta    4200
tatcaagaaa agaataatct acaataataa acggcatttt ttttttgattc tgtactcagt    4260 ttcttagtgt acagtttaac tgggcccaac aacctcgtta aaagtgtaaa atgcatcctt    4320
ttctccagtg gaaggattcc tggaggaata gggagacagt aattcagggt gaaattatag    4380
gctgtttttt gaagtgagga ggctggcccc atatactgat tagcaatatt taatatagat    4440
gtaaattatg acctcatttt ttctcccca agttttcag ttttcaaatg agttgagcca    4500
taattgccct tggtaggaaa aacaaaacaa aacagtggaa ctaggcttcc tgagcatggc    4560
cctacacttc tgatcaggag caaagccatc catagacaga ggagccggac aaatatggcg    4620
catcagaggt ggcttgcgca catatgcatt gaacggtaaa gagaaacagc gcttgccttt    4680
tcactaaagt tgactatttt tccttcttct cttacacacc gagattttct tgttagcaag    4740
gcctgacaag atttaacata aacatgacaa atcatagttg tttgttttgt tttgcttttc    4800 tcttttaacac tgaagatcat ttgtcttaaa taggaaaaag aaaatccact ccttacttcc    4860
atatttccaa gtacatatct ggtttaaact atgttatcaa atcatatttc accgtgaata    4920
ttcagtggag aacttctcta cctggatgag ctagtaatga tttcagatca tgctatcccc    4980
agaaataaaa gcaaaaaata taccctgtgt ggaatatagg ctgtgctttg atttactggt    5040
atttacccca aaataggctg tgtatggggg ctgacttaaa gatcccttgg aaagactcaa    5100
aactaccttc actagtagga ctcctaagcg ctgacctatt tttaaatgac acaaattcat    5160
gaaactaatg ttacaaattc atgcagtttg cactcttagt catcttcccc tagcacacca    5220
atagaatgtt agacaaagcc agcactgttt tgaaaataca gccaaacacg atgacttttg    5280
ttttgttttc tgccgttctt aaaagaaaaa aagataatat tgcaactctg actgaaagac    5340
ttatttttaa gaaacaggt tgtgtttggt gctgctaagt tctggccagt ttatcatctg    5400
gccttcctgc ctatttttta caaaacacga agacagtgtg taacctcgac attttgacct    5460
tcctttatgt gctagtttag acaggctcct gaatccacac ttaattttgc ttaacaaaag    5520
tcttaatagt aaacctcccc tcatgagctt gaagtcaagt gttcttgact tcagatattt    5580
cttttccttt ttttttttt tcctcatcac aactaagaga tacacaaact ctgaagaagc    5640
agaaatggag agaatgcttt taacaaaaaa gcatctgatg aaagatttta ggcaaacatt    5700
ctcaaaataa gagtgatatt ctggatgtag ttattgcagt tatctcatga caaatgaggc    5760
ctggattgga aggaaaatat agttgtgtag aattaagcat tttgatagga atctacaagg    5820
```

-continued

```
tagttgaata taataagcag gtttgggccc ccaaacttta gaaaatcaaa tgcaaaggtg    5880
ctggcaaaaa tgaggtttga gtggctggct gtaagagaag gttaactcct agtaaaaggc    5940
atttttagaa ataacaatta ctgaaaactt tgaagtatag tgggagtagc aaacaaatac    6000
atgttttttt tttcttacaa agaactccta aatcctgagt aagtgccatt cattacaata    6060
agtctctaaa tttaaaaaaa aaaaaatcat atgaggaaat ctagctttcc cctttacgct    6120
gcgtttgatc tttgtctaaa tagtgttaaa attcctttca ttccaattac agaactgagc    6180
ccactcgcaa gttggagcca tcagtgggat acgccacatt ttggaagccc cagcatcgtg    6240
tacttaccag tgtgttcaca aaatgaaatt tgtgtgagag ctgtacatta aaaaaaatca    6300
tcattattat tattatttgc agtcatggag aaccacctac ccctgacttc tgtttagtct    6360 ccttttttaaa taaaaattac tgtgttagag aagaaggcta ttaaatgtag tagttaacta   6420
tgcctcttgt ctgggggttt catagagacc ggtaggaaag cgcactcctg cttttcgatt    6480
tatggtgtgt gcaagtaaac aggtgcattg ctttcaacct gccatactag ttttaaaaat    6540
tcactgaaat tacaaagata catatatatg catatatata atggaaagtt tcccggaatg    6600
caacaattag cattttaaaa tcatatatag gcatgcacat tctaaatagt acttttttcat   6660 gcttcattgt ttctctggca gataatttta ctaagaagaa aaatagatat tcgactcccc    6720
ttccctaaac aaatccacgg gcagaggctc cagcggagcc gagcccctg gttttctcgt     6780 aggccctaga cggtgttgca tttatcagtg atgtcaaacg tgctcatttg tcagacatag    6840
ctgtaaatga aacaatgtg tggcaaaata caaagttaaa aaaaaa                    6887
```

```
<210> SEQ ID NO 4
<211> LENGTH: 403
<212> TYPE: PRT
<213> ORGANISM: Homo sapiens

<400> SEQUENCE: 4

Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
            20                  25                  30

Lys Lys Glu Pro Val Glu Thr Asp Arg Ile Ile Ser Gln Cys Gly Arg
        35                  40                  45

Leu Ile Ala Gly Gly Ser Leu Ser Ser Thr Pro Met Ser Thr Pro Cys
    50                  55                  60

Ser Ser Val Pro Pro Ser Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
                85                  90                  95

Tyr Pro Gln Gln Leu Asn Pro Glu Ala Leu Gly Phe Ser Pro Glu Asp
            100                 105                 110

Ala Val Glu Ala Leu Ile Ser Asn Ser His Gln Leu Gln Gly Gly Phe
        115                 120                 125

Asp Gly Tyr Ala Arg Gly Ala Gln Gln Leu Ala Ala Ala Gly Ala
    130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Gln Ser Gly
                165                 170                 175

Ala Gly Pro His Tyr His His His His His Ala Ala Gly His His
            180                 185                 190
```

His His Pro Thr Ala Gly Ala Pro Gly Ala Ala Gly Ser Ala Ala Ala
            195                 200                 205

Ser Ala Gly Gly Ala Gly Ala Gly Gly Gly Pro Ala Ser Ala
        210                 215                 220

Gly Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
                245                 250                 255

Phe Asp Asp Arg Phe Ser Asp Glu Gln Leu Val Thr Met Ser Val Arg
                260                 265                 270

Glu Leu Asn Arg Gln Leu Arg Gly Val Ser Lys Glu Glu Val Ile Arg
                275                 280                 285

Leu Lys Gln Lys Arg Arg Thr Leu Lys Asn Arg Gly Tyr Ala Gln Ser
            290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
                325                 330                 335

Leu Val Arg Glu Arg Asp Ala Tyr Lys Glu Lys Tyr Glu Lys Leu Val
                340                 345                 350

Ser Ser Gly Phe Arg Glu Asn Gly Ser Ser Ser Asp Asn Pro Ser Ser
            355                 360                 365

Pro Glu Phe Phe Ile Thr Glu Pro Thr Arg Lys Leu Glu Pro Ser Val
            370                 375                 380

Gly Tyr Ala Thr Phe Trp Lys Pro Gln His Arg Val Leu Thr Ser Val
385                 390                 395                 400

Phe Thr Lys

<210> SEQ ID NO 5
<211> LENGTH: 373
<212> TYPE: PRT
<213> ORGANISM: Homo sapiens

<400> SEQUENCE: 5

Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
                20                  25                  30

Lys Lys Glu Pro Val Glu Thr Asp Arg Ile Ile Ser Gln Cys Gly Arg
            35                  40                  45

Leu Ile Ala Gly Gly Ser Leu Ser Ser Thr Pro Met Ser Thr Pro Cys
        50                  55                  60

Ser Ser Val Pro Pro Ser Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
                85                  90                  95

Tyr Pro Gln Gln Leu Asn Pro Glu Ala Leu Gly Phe Ser Pro Glu Asp
            100                 105                 110

Ala Val Glu Ala Leu Ile Ser Asn Ser His Gln Leu Gln Gly Gly Phe
        115                 120                 125

Asp Gly Tyr Ala Arg Gly Ala Gln Gln Leu Ala Ala Ala Gly Ala
130                 135                 140

Gly Ala Gly Ala Ser Leu Gly Gly Ser Gly Glu Glu Met Gly Pro Ala
145                 150                 155                 160

```
Ala Ala Val Val Ser Ala Val Ile Ala Ala Ala Ala Gln Ser Gly
                165                 170                 175

Ala Gly Pro His Tyr His His His His His Ala Ala Gly His His
            180                 185                 190

His His Pro Thr Ala Gly Ala Pro Gly Ala Ala Gly Ser Ala Ala
        195                 200                 205

Ser Ala Gly Gly Ala Gly Gly Ala Gly Gly Gly Pro Ala Ser Ala
    210                 215                 220

Gly Gly Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
            245                 250                 255

Phe Asp Asp Arg Phe Ser Asp Glu Gln Leu Val Thr Met Ser Val Arg
            260                 265                 270

Glu Leu Asn Arg Gln Leu Arg Gly Val Ser Lys Glu Val Ile Arg
        275                 280                 285

Leu Lys Gln Lys Arg Arg Thr Leu Lys Asn Arg Gly Tyr Ala Gln Ser
        290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
            325                 330                 335

Leu Val Arg Glu Arg Asp Ala Tyr Lys Glu Lys Tyr Glu Lys Leu Val
            340                 345                 350

Ser Ser Gly Phe Arg Glu Asn Gly Ser Ser Ser Asp Asn Pro Ser Ser
            355                 360                 365

Pro Glu Phe Phe Met
    370

<210> SEQ ID NO 6
<211> LENGTH: 19
<212> TYPE: RNA
<213> ORGANISM: Artificial Sequence
<220> FEATURE:
<223> OTHER INFORMATION: c-MAF specific siRNA

<400> SEQUENCE: 6
acggcucgag cagcgacaa                                                       19

<210> SEQ ID NO 7
<211> LENGTH: 19
<212> TYPE: RNA
<213> ORGANISM: Artificial Sequence
<220> FEATURE:
<223> OTHER INFORMATION: c-MAF specific siRNA

<400> SEQUENCE: 7
cuuaccagug uguucacaa                                                       19

<210> SEQ ID NO 8
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 8
uggaagacua cuacuggaug                                                      20
```

```
<210> SEQ ID NO 9
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 9
auuugcaguc auggagaacc                                              20

<210> SEQ ID NO 10
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 10
caaggagaaa uacgagaagu                                              20

<210> SEQ ID NO 11
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 11
acaaggagaa auacgagaag                                              20

<210> SEQ ID NO 12
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 12
accuggaaga cuacuacugg                                              20

<210> SEQ ID NO 13
<211> LENGTH: 13878
<212> TYPE: DNA
<213> ORGANISM: Homo sapiens

<400> SEQUENCE: 13
aactatatat taaacacctc cggtctgaga ggccgtgttg ggtgtctttg tcaggtgaag      60
aaagagaaga aggctggtac accttcccag gaattctcac tgaagaaaac atctggattt    120
tttacatctc ttgtgcaaaa caaacaaaga tttcattaag tgatgtatat tgttttccaa    180
ggaagaaacc tgcagagaca aaaacaaata agcaaataat tgaaacaaaa atatgataaa    240
cccccaaatt cttccagtgc taatttactt gttatcatgg ttctctacaa aggcagagat    300
cactaattac aggttttttcc agaattcaca tttcacgtca agatcatcca atccaaacag   360
tgtacggaaa gcctagggcc ttcttcactt tgcccccctac cccacccctac acacacgccc   420 ccatctaaat gataccccttg gaaagaaacc tacacatctc atttgtctat attttgcttc   480
ctccctcgcc tcccggtaac caaatgtgag ttgttctcta actgcactgg agaatcagaa    540
tttattgtac atatgtttgt gttccactta ataaaaaaac ctatatttta agataaactt    600
tgttagtaat tcatgaggta agtgactatt tatgctaatc aggcagaaat atattctcaa    660
gcataatgca ttacataaat ttgaatgtaa aatgttcaat tatgaagtaa atacaggtaa    720
```

```
tgcaaataat aaattacctc taataaaaat tataaaagat gtgccttgaa agagagagcg    780
gctttaactt acaactgtga attgcttaaa gagaaaagaa ttaataaatg ctgaattact    840
ctgatgatta tttagcacat aattcaccta ttcataacga ctcctagtaa tcagactgtt    900
gtttcacatc ctccaacatg aggcaagact gtttcctcag caattttgcc cttatcagat    960
tatctcgtct gattctatta atttcttcc atgaatctgc taacagtgat tgtgattta    1020
cttaccctgc taactgaaga ctgttaaaag gatttatcta acactggacc taagaacagt   1080
gtacgcctta tcgttcagtt actctgaaga actctttctc aaatcaattt agttggtttc   1140
atagtgaaat ttagtggaca ctggttagtt ctgccccata aaatcagccc ctaaacaaag   1200
agtccagaca ccatacctga tgcatcccat tctattcaga ttatggatgt ctgattccaa   1260
catgatatat ttgagttgct ataactcaca atcggggaaa atatattcct ttaagctttt   1320
aatctttgta atttggacat gaacaggggt tttgttttc attttttgcat gaagtcatta   1380
tgtatgtact gacgtgaaac tataattgtg tttctgatgt tactgtgtca caatattcta   1440
tgcgatgtaa cccatgtcct cctcccctc acaaatctcc tataaatatt cattgctttc    1500
aaaaactta atactactgg tccgaattgg tcaataatga caaatgcatg gtttctaaat    1560
tactgtatat tgttctacag agattactag agtatatata gcaaggggat gttaagcagt   1620
aagaaaacac agttcacatt gtatttggat tagattggct tggatagaag tgaaacaaac   1680
aatgttagca aagaagtcta aagacatgtg gcccactgta attgtacaga atcaaaaacc   1740
tgaatagtac tcattaaaat gagagagctc aattgttata aagaaatgc tgctaacaga    1800
gaactgtaaa tgtttagaca ccctgtgaa tcactaaata ataatgtaaa aaggataaaa     1860
atgagaatta agttataagc ctgagagcat tactgctaca catctaaaaa aataattctg   1920
atcctctctt ttttttttcc aagagaaaat gggcgactat aaaagacctt gcaataagag   1980
aaataaaaat accatgtctt cacagcagtg tacataaata aaccataaaa atgtgcagat   2040
aataatatat ttagctgccc aaacatgggc atttaatttc tagaaatgat atataacaat   2100
gtaacaatta gatactcagc catgaatgtg tatggcacag tcttcatcat tagcaaactt   2160
tgtgtataaa atattattta ttatttatta taatactgct ttcagaggca atgatcatac   2220
cttacagctt ttaacacaaa tatgatgcaa aaggattaaa agtatatcat aaacaaacaa   2280
taaattcttt ctaaatacac ttaaattcat attttacatg aaaaatataa acttcctaca   2340
tttgtgacta ctgactttta aaaagaccta gaaaactatt gttacgggca atgttaaatg   2400
acataatgct tatgtaatgg aaagtgtgga ttttcctcta aataaactat aatcccttaa   2460
cttcattact agggaaaata ttgttaaaga gaaggaaagc aagggaattc tgctaggttg   2520
cataaatatt gacataatct tcactctttc ttccccaaac tggtaataga catagtttat   2580
tccacccaac aaaatgctct tataagacca aaactaccct tattaacaac ttctctgcag   2640
tcacgatgaa aagaaacact acttgtctga aaaataccga cagcgctgcc cttttcagat   2700
tagggtgtgc ctacgaatct tttgggaagt cttccattaa ggattcctgg gtttgctgaa   2760
actgaagtct actaggatca gagaaattaa cacaggtcta atatggtgca aggaacgagt   2820
gagagacacc tgaggttata aatagcaaag catgctgcgg ggtggggaag accattctga   2880
agtgcaatgt tcaagacgct ggcttaatat atgactaagt gtcagaagtc aggttttctg   2940
agaattactt tccagataaa caactttata gcactgcact taatcttact tactagagac   3000
atctcattta tcactgaatt acaagtaact ttaatcctat tgatattgcc ataaagcccg   3060
ttgaaaatcc atcctggcac ttttaagggg tttggggccc tgttacatgg ggatcctctt   3120
```

```
gcaaaggtct cagccagaaa ttacaccccg agggtgtctg tatcccctgg cctctttgtc    3180
aacaatcaag gagaagagga ggggcaaaaa tgatctctgc atctgccagc actttcttcg    3240 gccccttttcc tatagggtcg ggttctccca cttcagtcaa actaactttg tgtgtctctt   3300
tcctcctccc acactgggta accagctgct tttcacttca tcgacaaaac tggacacgga    3360
tcaatttcaa ctgacctttg ccgaaaggtg gcgctgttga ggtaaaaacc aactcgctcc    3420
aacaatagtt tccactcttc gatccttttg caggcttttc agaattttttt ttttttttta   3480 atgcaccctc ctagcgtctc cccctcctca taaagtaaaa taaatacgat taaaaacacc    3540
aaatgcattt cattaattga aggaatcaac agtcccaact tctaagcaga cgggctggtc    3600
ttccaaaggc tgggtcggtt tcaggagctt tctctccaaa taaatctctg cttcttcgac    3660
ttgcctatcg ctttaaaatc ttagaaacag agttagttgt tggtttcctt ctttttttctt   3720 tttcttttttt atttcttttt tgcataaact tttagagaat caatctagaa atttgaacta   3780
cttattagca tttgcaactg ggggtggggg gagcagcctc ccccaccccca cccccactc    3840 tgcgtttccg gactagttcc agaaaccgcg gtttaaaatt taacccttcg agggtagctg    3900
gtgagggctg gggtattgtt tttcccccctt gctccctgcc acgatcaagt ccgaaataat   3960
taaaggaaac gtaaagtgc aaagggcgcg cctgaccctg ataaacagag gtcagatttc     4020
gtaaggggac gggtgagtgt gagtgtgtgt gtgtttgtgt gtgtgtgtgt aagagagaga    4080
gagagcgagc gcgcaatatg agtctcaaag gccaaactcc ggccagtcag gagccggaag    4140
gctgagcccg gctgacctga ctttgagctt ccccggagtt atctcgcata ggcgctcgct    4200
ctgtccaagg gcacgcgacg ccagcgggca gccggtctcc gtgaagaatg gcctctaaac    4260
aacttatttt acctcgttgt aaagagaggg ataaaatggg cttttccctct ccacggatgc    4320 ccagccttct gggcaggcgc atggccgggc ggcgcccagc ccgcagcccc gatccggaca    4380
ccccactgca tccctccctt cccggtccct tccccgcacg ggcgcccgag agacggacaa    4440
agagttgggg ccaagtttga gcgccgggca cggccaggct cagggaagga aggtccccgg    4500
cagacacctg ggtaccagag ttggtgcgag gaggaaaagc tgggaggcga attcacaatc    4560
ctgggggtgg agggcaggca ggggagggga atcaggccaa tcccagccga gtgagccccc    4620
agcgagctgg ggctccggat gggaggcctg tctcgcgctc caaagaaaag caaaccgccc    4680
tcccaggtcc gcccggattg ccgaagcccc tctggaaaaa ctccttcccc tcttacacca    4740
aactttgcgc cgggcctcgt tccctcccgg gtaggcagcg gcgcaggaag ggttaagcca    4800
gcccgtccca gctgacagtc agctgattgg gccctgattg acagtccga aaagtttcct     4860 tgtttctata ctattatgct aatcgcggcc gctctcgccg cctcccattg gcccggagtg    4920
ccagtcaatt tctcatttgg acctgacgtc acgagtgcta taaaactcag caattgcttt    4980
aaactcttct tgctggatca gaggctttaa aatctttttt catcttctag ctgtagctcg    5040
ggctgcttgt cggcttggcc tccccctccc cctttgctc tctgcctcgt ctttccccag     5100
gacttcgcta ttttgctttt ttaaaaaaag gcaagaaaga actaaactcc ccctcccctc    5160
tcctccagtc gggctgcacc tctgccttgc actttgcaca gaggtagaga gcgcgcgagg    5220
gagagagagg aaagaaaaaa aataataaag agagccaagc agaagaggag gcgagaagca    5280
tgaagtgtta actccccgt gccaaggccc gcgccgcccg gacagacgcc cgccgcgcct     5340
ccagccccga gcggacgccg cgcgcgccct gcctgcagcc cgggccggcg aggcgagccc    5400
ttccttatgc aaagcgcgca gcggagcggc gagcggggga cgccgcgcac cgggccgggc    5460
tcctccagct tcgccgccgc agccaccacc gccgccaccg cagctcgcgg aggatcttcc    5520
```

```
cgagcctgaa gccgccggct cggcgcgcaa ggaggcgagc gagcaaggag gggccggggc    5580
gagcgaggga gcacattggc gtgagcaggg gggagggagg gcgggcgcgg ggggcgcggg    5640
cagggcgggg gggtgtgtgt gtgagcgcgc tcggaggttt cgggccagcc accgccgcgc    5700
aagctagaag cgccccagcc cggcaagctg gctcacccgc tggccaccca gcacagcccg    5760
ctggcccctc tcctgcagcc catctggcgg agcggcggcg gcggcggcgg cggcggcagg    5820
agaatggcat cagaactggc aatgagcaac tccgacctgc ccaccagtcc cctgccatg     5880 gaatatgtta atgacttcga tctgatgaag tttgaagtga aaaggaacc ggtggagacc     5940 gaccgcatca tcagccagtg cggccgtctc atcgccgggg gctcgctgtc ctccacccc     6000 atgagcacgc cgtgcagctc ggtgccccct tcccccagct tctcggcgcc cagcccgggc    6060
tcgggcagcg agcagaaggc gcacctggaa gactactact ggatgaccgg ctacccgcag    6120
cagctgaacc ccgaggcgct gggcttcagc cccgaggacg cggtcgaggc gctcatcagc    6180
aacagccacc agctccaggg cggcttcgat ggctacgcgc gcggggcgca gcagctggcc    6240
gcggcggccg gggccggtgc cggcgcctcc ttgggcggca gcggcgagga gatgggcccc    6300
gccgccgccg tggtgtccgc cgtgatcgcc gcggccgccg cgcagagcgg cgcgggcccg    6360
cactaccacc accaccacca ccacgccgcc ggccaccacc accacccgac ggccggcgcg    6420
cccggcgccg cgggcagcgc ggccgcctcg gccggtggcg ctgggggcgc gggcggcggt    6480
ggcccggcca gcgctggggg cggccggcgg ggcggcggcg gcggaggcgg cggggcgcg     6540 gcggggggcgg ggggcgccct gcacccgcac cacgccgccg gcggcctgca cttcgacgac    6600
cgcttctccg acgagcagct ggtgaccatg tctgtgcgcg agctgaaccg gcagctgcgc    6660 gggtcagca aggaggaggt gatccggctg aagcagaaga ggcggaccct gaaaaaccgc    6720
ggctatgccc agtcctgccg cttcaagagg gtgcagcaga cacgtcct ggagtcggag     6780 aagaaccagc tgctgcagca agtcgaccac ctcaagcagg agatctccag gctggtgcgc    6840
gagagggacg cgtacaagga gaaatacgag aagttggtga gcagcggctt ccgagaaaac    6900
ggctcgagca gcgacaaccc gtcctctccc gagttttttca tgtgagtctg acacgcgatt    6960
ccagctagcc accctgataa gtgctccgcg ggggtccggc tcgggtgtgg gcttgctagt    7020
tctagagcca tgctcgccac cacctcacca ccccccacccc caccgagttt ggccccctg    7080 gcccctaca cacacacaaa cccgcacgca cacaccacac acacacacac acacacacac    7140 acacccaca ccctgctcga gttttgtggtg gtggtggctg ttttaaactg gggagggaat    7200
gggtgtctgg ctcatggatt gccaatctga aattctccat aacttgctag cttgttttt     7260 tttttttttt acaccccccc gccccacccc cggacttgca caatgttcaa tgatctcagc    7320
agagttcttc atgtgaaacg ttgatcacct ttgaagcctg catcattcac atatttttc     7380 ttcttcttcc ccttcagttc atgaactggt gttcattttc tgtgtgtgtg tgtgttttat    7440
tttgtttgga ttttttttt taattttact tttagagctt gctgtgttgc ccactttt      7500 tccaacctcc accctcactc cttctcaacc catctcttcc gagatgaaag aaaaaaaaaa    7560
gcaaagtttt tttttcttct cctgagttct tcatgtgaga ttgagcttgc aaaggaaaaa    7620
aaaatgtgaa atgttataga cttgcagcgt gccgagttcc atcgggtttt ttttttagca    7680
ttgttatgct aaaatagaga aaaaaatcct catgaacctt ccacaatcaa gcctgcatca    7740
accttctggg tgtgacttgt gagttttggc cttgtgatgc caaatctgag agtttagtct    7800
gccattaaaa aaactcattc tcatctcatg cattattatg cttgctactt tgtcttagca    7860
acaatgaact ataactgttt caaagacttt atggaaaaga gacattatat taataaaaaa    7920
```

```
aaaaagcctg catgctggac atgtatggta taattatttt ttcctttttt tttccttttg     7980
gcttggaaat ggacgttcga agacttatag catggcattc atactttgt tttattgcct      8040 catgactttt ttgagtttag aacaaaacag tgcaaccgta gagccttctt cccatgaaat     8100
tttgcatctg ctccaaaact gctttgagtt actcagaact tcaacctccc aatgcactga    8160
aggcattcct tgtcaaagat accagaatgg gttacacatt taacctggca aacattgaag    8220
aactcttaat gttttctttt taataagaat gacgccccac tttggggact aaaattgtgc    8280
tattgccgag aagcagtcta aaatttattt tttaaaaaga gaaactgccc cattattttt    8340
ggtttgtttt atttttattt tatattttt ggcttttggt cattgtcaaa tgtggaatgc      8400
tctgggtttc tagtatataa tttaattcta gttttttataa tctgttagcc cagttaaaat   8460
gtatgctaca gataaaggaa tgttatagat aaatttgaaa gagttaggtc tgtttagctg    8520
tagatttttt aaacgattga tgcactaaat tgtttactat tgtgatgtta agggggtag     8580 agtttgcaag gggactgttt aaaaaaagta gcttatacag catgtgcttg caacttaaat    8640
ataagttggg tatgtgtagt ctttgctata ccactgactg tattgaaaac caaagtatta    8700 agagggaaa cgcccctgtt tatatctgta ggggtatttt acattcaaaa atgtatgttt     8760
ttttttcttt tcaaaattaa agtatttggg actgaattgc actaagatat aacctgcaag   8820
catataatac aaaaaaaaat tgcaaactg tttagaacgc taataaaatt tatgcagtta     8880
taaaaatggc attactgcac agttttaaga tgatgcagat tttttttacag ttgtattgtg  8940 gtgcagaact ggatttttctg taacttaaaa aaaaatccac agttttaaag gcaataatca   9000
gtaaatgtta tttcaggga ctgacatcct gtctttaaaa agaaatgaaa agtaaatctt     9060
accacaataa atataaaaaa atcttgtcag ttactttct tttacatatt ttgctgtgca     9120
aaattgtttt atatcttgag ttactaacta accacgcgtg ttgttcctat gtgcttttct   9180 ttcatttca attctggtta tatcaagaaa agaataatct acaataataa acggcatttt    9240
tttttgattc tgtactcagt ttcttagtgt acagtttaac tgggcccaac aacctcgtta   9300
aaagtgtaaa atgcatcctt ttctccagtg gaaggattcc tggaggaata gggagacagt   9360
aattcagggt gaaattatag gctgttttt gaagtgagga ggctggcccc atatactgat    9420
tagcaatatt taatatagat gtaaattatg acctcatttt ttttctcccca agttttcag   9480 ttttcaaatg agttgagcca taattgccct tggtaggaaa aacaaaacaa aacagtggaa   9540
ctaggcttcc tgagcatggc cctacacttc tgatcaggag caaagccatc catagacaga   9600
ggagccggac aaatatggcg catcagaggt ggcttgcgca catatgcatt gaacggtaaa   9660
gagaaacagc gcttgccttt tcactaaagt tgactatttt tccttcttct cttacacacc    9720
gagattttct tgttagcaag gcctgacaag atttaacata aacatgacaa atcatagttg   9780
tttgttttgt tttgcttttc tctttaacac tgaagatcat ttgtcttaaa taggaaaaag   9840
aaaatccact ccttacttcc atatttccaa gtacatatct ggtttaaact atgttatcaa    9900
atcatatttc accgtgaata ttcagtggag aacttctcta cctggatgag ctagtaatga   9960
tttcagatca tgctatcccc agaaataaaa gcaaaaaata ataccctgtgt ggaatatagg   10020 ctgtgctttg atttactggt atttaccca aataggctg tgtatggggg ctgacttaaa    10080
gatcccttgg aaagactcaa aactaccttc actagtagga ctcctaagcg ctgacctatt   10140
tttaaatgac acaaattcat gaactaatg ttacaaattc atgcagtttg cactcttagt    10200
catcttcccc tagcacacca atagaatgtt agacaaagcc agcactgttt tgaaaataca   10260
gccaaacacg atgactttg ttttgttttc tgccgttctt aaaagaaaaa aagataatat    10320
```

```
tgcaactctg actgaaagac ttatttttaa gaaaacaggt tgtgtttggt gctgctaagt    10380
tctggccagt ttatcatctg gccttcctgc ctatttttta caaaacacga agacagtgtg    10440
taacctcgac attttgacct tcctttatgt gctagtttag acaggctcct gaatccacac    10500
ttaattttgc ttaacaaaag tcttaatagt aaacctcccc tcatgagctt gaagtcaagt    10560
gttcttgact tcagatattt cttttcttttt tttttttttt tcctcatcac aactaagaga    10620
tacacaaact ctgaagaagc agaaatggag agaatgcttt taacaaaaaa gcatctgatg    10680
aaagatttta ggcaaacatt ctcaaaataa gagtgatatt ctggatgtag ttattgcagt    10740
tatctcatga caaatgaggc ctggattgga aggaaaatat agttgtgtag aattaagcat    10800
tttgatagga atctacaagg tagttgaata taataagcag gtttgggccc ccaaacttta    10860
gaaaatcaaa tgcaaggtg ctggcaaaaa tgaggtttga gtggctggct gtaagagaag    10920
gttaactcct agtaaaaggc attttagaa ataacaatta ctgaaaactt tgaagtatag    10980
tgggagtagc aaacaaatac atgttttttt tttcttacaa agaactccta aatcctgagt    11040
aagtgccatt cattacaata agtctctaaa tttaaaaaaa aaaaaatcat atgaggaaat    11100 ctagcttttcc cctttacgct gcgtttgatc tttgtctaaa tagtgttaaa attccttttca    11160 ttccaattac agaactgagc ccactcgcaa gttggagcca tcagtgggat acgccacatt    11220
ttggaagccc cagcatcgtg tacttaccag tgtgttcaca aaatgaaatt tgtgtgagag    11280
ctgtacatta aaaaaaatca tcattattat tattatttgc agtcatggag aaccacctac    11340
ccctgacttc tgtttagtct cctttttaaa taaaaattac tgtgttagag aagaaggcta    11400
ttaaatgtag tagttaacta tgcctcttgt ctgggggttt catagagacc ggtaggaaag    11460
cgcactcctg cttttcgatt tatggtgtgt gcaagtaaac aggtgcattg ctttcaacct    11520
gccatactag ttttaaaaat tcactgaaat tacaagata catatatatg catatatata    11580
atggaaagtt tcccggaatg caacaattag cattttaaaa tcatatatag gcatgcacat    11640
tctaaatagt acttttttcat gcttcattgt ttctctggca gataattta ctaagaagaa    11700 aaatagatat tcgactcccc ttccctaaac aaatccacgg gcagaggctc cagcggagcc    11760 gagcccctg gttttctcgt aggccctaga cggtgttgca tttatcagtg atgtcaaacg    11820
tgctcatttg tcagacatag ctgtaaatga aaacaatgtg tggcaaaata caagttagt    11880 taaatacaca ccctctgtgt gattttttgc tcccttttct tttttgctcc tactcaaaaa    11940
aaaaaaaatc acctccttta catttccctg gcttcttgca tgtttccctt tcaaaaacc    12000 atgtaataat ttttttacaat gtatctgaca cattaatata ttgacatcaa ataggcagac    12060
attctacttt tgcctggcaa ataaatctgc tacggagaca tcatttcctc actgtctcaa    12120
agccataact acctgggagt cttttcaacac agacccctcc gatgggaaat gctgtttatt    12180
actgaatgca ggatgctcac gctctgatct tttctccctt gtgcctttac cccagtcatt    12240
tttacttagc aacaccaatt ctagatactt ctgttctgaa gtagaaccac ccccttgcca    12300
cactgccagt tttcctgcta aaagcagtgg acagaagaca gatcatggtc accctcacaa    12360
acatggcaca cagctgtctc ggtagctgca ttcccagcat gtcctggtct aaatatctag    12420
agttgcctat gacacgttca aaggttccca agcacagtac attgggaggc ttttgctgct    12480
gtggccgttg ttttcgttta ggccaactta cttccgtatt cacatactct tggctttacg    12540
aaatacactc ctccagtcta ctaggccaat caatatattt aaaagtctga ttgccacata    12600
agtctctctc tctctctttt tgtttttgt ttgtttgtt ttttctgttt tggctgccgg    12660
tagttaaaga ctgagatagg ttggaagact aaaatacagg agtacatgag tgacaacctt    12720
```

-continued

```
cagccgtctg atttccatgc cggtaaaaca cacaaccaag ctcttcttag cgctgctaat  12780
ataaacattc actaagaggg aataggaagt gagatttacc agcttcactt tgctgatttg  12840
caaggttccc cactacgatt cactgtcatt tgatttttga aaaataattt tgtccgtctc  12900
tttgaagaaa tgtcttagtt cttttatttt gtttgtttgg ttttttttag agaagtttta  12960
tctgcagtga taggctacaa tttttatctc cgctgattat ttgtcaggat gctgaatgaa  13020
taatttggtc ctgtgccttc cttgttgttc tgaggaaaat aagagaaact tggaagtttg  13080
tttcactctt agcccatcct aaatctaaaa gaagatgtcc caggtccagg caggccatgt  13140
agtagttata aaggaggtgg tccaggtcca gccacctcaa tcaggatttg tttgttttga  13200
agcatttgct taaaagcgga gcaagagtct taacccaact tgccataaca ctgcttttct  13260
cgcttttgat gtaaatcttc aaaattcaga catcaaacag ccccagaaaa ggggaattct  13320
ctccaggcat tgctccgccc cagctcctga acaaacccag ctctgtctag cattttttc   13380 cctagcgggg gtaggggaca gggtgagaga atttcagtct cccaggctgt ctcatgattg  13440
ttagggcata aagaaacaca gtcctgccac aaattgggag catctttacc ctttagagag  13500
aaacaaaaca aaactaaaca aacaaatcaa attgctttgc atgaaggcgt agcaaataaa  13560
atctcgggct ccctgttccc tgcaccattt gtaggaggtg agaaatgagg gaaacaagag  13620 aaagggaac tttaaaagcg ggaggcccag aaataatccc tgttaccagt ctgaatttca   13680
cttgctccgt ggctaacgtc agacctagtg tgcatgtatg ccagaagtaa actaggctcg  13740
gctgtccatt tctttaaaat atgttcacat gtttcctttt tgaaaacaat tttggggact  13800
aaacccaaat ggagagattt gaggaaatcg ttaatgtctt aacatttgag tatatttata  13860
aatgtatcag tctgtgat                                                 13878
```